US012807670B2

(12) United States Patent
Wang et al.

(10) Patent No.: US 12,807,670 B2
(45) Date of Patent: Nov. 24, 2026

(54) INSULIN-Fc FUSION PROTEIN AND APPLICATION THEREOF

(71) Applicant: JIANGSU GENSCIENCES INC., Jiangsu (CN)

(72) Inventors: Yali Wang, Jiangsu (CN); Xian Chen, Beijing (CN); Luyan Zhu, Beijing (CN); Tingting Zhou, Beijing (CN); Weichuan Mo, Beijing (CN); Chengliang Liu, Beijing (CN); Weiwei Hao, Beijing (CN); Shuya Wang, Henan (CN); Zhaoju Jiang, Beijing (CN); Zijia Ren, Henan (CN); Hongsheng Su, Beijing (CN)

(73) Assignee: JIANGSU GENSCIENCES INC., Nantong (CN)

( * ) Notice: Subject to any disclaimer, the term of this patent is extended or adjusted under 35 U.S.C. 154(b) by 887 days.

(21) Appl. No.: 18/016,714

(22) PCT Filed: Jul. 19, 2021

(86) PCT No.: PCT/CN2021/107040
§ 371 (c)(1),
(2) Date: Jan. 18, 2023

(87) PCT Pub. No.: WO2022/017309
PCT Pub. Date: Jan. 27, 2022

(65) Prior Publication Data

US 2023/0272030 A1 Aug. 31, 2023

(30) Foreign Application Priority Data

Jul. 24, 2020 (CN) ........................ 202010723972.9

(51) Int. Cl.
*C07K 14/62* (2006.01)
*A61P 3/10* (2006.01)

(52) U.S. Cl.
CPC ................ *C07K 14/62* (2013.01); *A61P 3/10* (2018.01); *C07K 2319/30* (2013.01)

(58) Field of Classification Search
CPC ........ C07K 14/62; C07K 2319/30; A61P 3/10
See application file for complete search history.

(56) References Cited

U.S. PATENT DOCUMENTS

| | | | | |
|---|---|---|---|---|
| 1,087,068 | A * | 2/1914 | Lancaster | A47L 13/02 15/93.1 |
| 7,576,190 | B2 | 8/2009 | Glaesner et al. | |
| 8,518,668 | B2 | 8/2013 | Nøergaard et al. | |
| 2015/0299285 | A1 | 10/2015 | Dimarchi et al. | |
| 2016/0008483 | A1 | 1/2016 | Hwang et al. | |
| 2016/0024169 | A1 | 1/2016 | Dimarchi et al. | |
| 2016/0215037 | A1 | 7/2016 | Madsen et al. | |
| 2018/0177851 | A1 | 6/2018 | Baldwin et al. | |
| 2018/0256731 | A1 | 9/2018 | Hwang et al. | |
| 2018/0355043 | A1 | 12/2018 | Martinez et al. | |
| 2019/0315828 | A1 | 10/2019 | Lancaster et al. | |
| 2020/0231646 | A1 * | 7/2020 | Lancaster | A61P 3/10 |
| 2020/0254108 | A1 | 8/2020 | Heo et al. | |

FOREIGN PATENT DOCUMENTS

| | | | |
|---|---|---|---|
| CN | 1798767 | B | 2/2011 |
| CN | 103509118 | A | 1/2014 |
| CN | 104995206 | A | 10/2015 |
| CN | 201480006998 | A | 10/2015 |
| CN | 105636979 | A | 6/2016 |
| CN | 110612112 | A | 12/2019 |
| CN | 111386130 | A | 7/2020 |
| JP | 2008-506635 | A | 3/2008 |
| JP | 2010-504742 | A | 2/2010 |
| JP | 2016-510003 | A | 4/2016 |
| JP | 2016-512255 | A | 4/2016 |
| JP | 2019-502698 | A | 1/2019 |
| JP | 2020-503889 | A | 2/2020 |
| WO | 9632478 | A1 | 10/1996 |
| WO | 9734631 | A1 | 9/1997 |
| WO | 2008/037735 | A1 | 4/2008 |
| WO | 2018/185131 | A2 | 10/2018 |
| WO | 2019/066570 | A1 | 4/2019 |
| WO | 2019/219048 | A1 | 11/2019 |
| WO | 2020006529 | A1 | 1/2020 |

OTHER PUBLICATIONS

Office Action (Notice of Reasons for Refusal) issued Jan. 9, 2024, by the Japan Patent Office in corresponding Japanese Patent Application No. 2023-503514 and an English translation of the Office Action. (8 pages).

Church et al, "Pharmacological characterization of an ultra-long acting once-weekly Insulin-Fc fusion with continuous glucose monitoring," European Association for the Study of Diabetes, Oct. 3, 2018, Abstract, 1 page.

Glaesner et al, "Engineering and characterization of the long-acting glucagon-like peptide-1 analogue LY2189265, an Fc fusion protein," Diabetes/Metabolism Research and Reviews, vol. 26, Apr. 30, 2010, pp. 287-296.

Yang et al, "Expression and Characterization of a Potent Long-acting GLP-1 Receptor Agonist, GLP-1-IgG2o-Fc," PLOS ONE, vol. 11, No. 5, May 27, 2016, pp. 1-14.

Wang et al, "Novel GLP-1 Fusion Chimera as Potent Long Acting GLP-1 Receptor Agonist," PLOS ONE, vol. 5, No. 9, Sep. 15, 2020, pp. 1-9.

He et al, "Secretory Expression of Recombinant Human Insulin in the Pichia Pastoris," Chinese Journal of Pharmaceutical Biotechnology, vol. 16, No. 2, Dec. 31, 2009, pp. 108-112 (English Abstract).

(Continued)

*Primary Examiner* — Gyan Chandra
(74) *Attorney, Agent, or Firm* — Buchanan Ingersoll & Rooney PC

(57) ABSTRACT

Provided is a fusion protein of insulin and an immunoglobulin Fc region. Specifically, the present invention relates to an insulin fusion protein having a prolonged in vivo half-life and stability, a preparation that contains the fusion protein, a preparation method therefor and an application thereof.

7 Claims, 11 Drawing Sheets

Specification includes a Sequence Listing.

(56) References Cited

OTHER PUBLICATIONS

Sreenivas et al, "Enhancement in production of recombinant two-chain Insulin Glargine by over-expression of Kex2 protease in Pichia pastoris," Applied Microbiology Biotechnology, Sep. 20, 2014, 10 pages.
International Search Report and Written Opinion issued in PCT/CN2021/107040, mailed Sep. 28, 2021, 19 pages. (English translation of ISR).
Pechenov et al., "Improving Drug-Like Properties of Insulin and GLP-1 via Molecule Design and Formulation and Improving Diabetes Management with Device & Drug Delivery", Advance Drug Delivery Reviews, (Jan. 30, 2017), vol. 112, pp. 106-122.
Extended European Search Report issued Jan. 22, 2025, by the European Patent Office in corresponding European Patent Application No. 21845572.3-1111. (19 pages).
Office Action (Communication pursuant to Rule 164(1) EPC) issued Sep. 24, 2024, by the European Patent Office in corresponding European Patent Application No. 21845572.3-1111. (16 pages).

* cited by examiner

A

B

SS302-005

SS302-008

SS302-014

A

B

A

B

A

B

SEQUENCE LISTING

<160> NUMBER OF SEQ ID NOS: 132

<210> SEQ ID NO 1
<211> LENGTH: 21
<212> TYPE: PRT
<213> ORGANISM: Homo sapiens

<400> SEQUENCE: 1

```
Gly Ile Val Glu Gln Cys Cys Thr Ser Ile Cys Ser Leu Tyr Gln Leu
1               5                   10                  15

Glu Asn Tyr Cys Asn
            20
```

<210> SEQ ID NO 2
<211> LENGTH: 30
<212> TYPE: PRT
<213> ORGANISM: Homo sapiens

<400> SEQUENCE: 2

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

<210> SEQ ID NO 3
<211> LENGTH: 31
<212> TYPE: PRT
<213> ORGANISM: Homo sapiens

<400> SEQUENCE: 3

```
Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30
```

<210> SEQ ID NO 4
<211> LENGTH: 30
<212> TYPE: PRT
<213> ORGANISM: Artificial Sequence
<220> FEATURE:
<223> OTHER INFORMATION: Linker

<400> SEQUENCE: 4

```
Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu
            20                  25                  30
```

<210> SEQ ID NO 5
<211> LENGTH: 20
<212> TYPE: PRT
<213> ORGANISM: Artificial Sequence
<220> FEATURE:
<223> OTHER INFORMATION: Linker

<400> SEQUENCE: 5

```
Glu Ala Glu Asp Leu Gln Val Gly Gln Val Glu Leu Gly Gly Gly Pro
```

```
1               5                   10                  15

Gly Ala Gly Ser
            20


<210> SEQ ID NO 6
<211> LENGTH: 15
<212> TYPE: PRT
<213> ORGANISM: Artificial Sequence
<220> FEATURE:
<223> OTHER INFORMATION: Linker

<400> SEQUENCE: 6

Glu Ala Glu Asp Leu Gln Val Gly Gln Val Glu Leu Gly Gly Gly
1               5                   10                  15


<210> SEQ ID NO 7
<211> LENGTH: 19
<212> TYPE: PRT
<213> ORGANISM: Artificial Sequence
<220> FEATURE:
<223> OTHER INFORMATION: Linker

<400> SEQUENCE: 7

Glu Ala Glu Asp Leu Gln Val Gly Gln Val Glu Leu Ser Leu Gln Pro
1               5                   10                  15

Leu Ala Leu


<210> SEQ ID NO 8
<211> LENGTH: 4
<212> TYPE: PRT
<213> ORGANISM: Artificial Sequence
<220> FEATURE:
<223> OTHER INFORMATION: Linker

<400> SEQUENCE: 8

Glu Ala Glu Asp
1


<210> SEQ ID NO 9
<211> LENGTH: 5
<212> TYPE: PRT
<213> ORGANISM: Artificial Sequence
<220> FEATURE:
<223> OTHER INFORMATION: Linker

<400> SEQUENCE: 9

Tyr Pro Gly Asp Val
1               5


<210> SEQ ID NO 10
<211> LENGTH: 2
<212> TYPE: PRT
<213> ORGANISM: Artificial Sequence
<220> FEATURE:
<223> OTHER INFORMATION: Linker

<400> SEQUENCE: 10

Ala Ala
1


<210> SEQ ID NO 11
<211> LENGTH: 2
<212> TYPE: PRT
<213> ORGANISM: Artificial Sequence
<220> FEATURE:
<223> OTHER INFORMATION: Linker
```

<400> SEQUENCE: 11

Glu Trp
1

<210> SEQ ID NO 12
<211> LENGTH: 24
<212> TYPE: PRT
<213> ORGANISM: Artificial Sequence
<220> FEATURE:
<223> OTHER INFORMATION: Signal peptide NS

<400> SEQUENCE: 12

Met Ala Leu Trp Met Arg Leu Leu Pro Leu Leu Ala Leu Leu Ala Leu
1 5 10 15

Trp Gly Pro Asp Pro Ala Ala Ala
20

<210> SEQ ID NO 13
<211> LENGTH: 19
<212> TYPE: PRT
<213> ORGANISM: Artificial Sequence
<220> FEATURE:
<223> OTHER INFORMATION: Signal peptide LS

<400> SEQUENCE: 13

Met Arg Ser Leu Gly Ala Leu Leu Leu Leu Leu Ser Ala Cys Leu Ala
1 5 10 15

Val Ser Ala

<210> SEQ ID NO 14
<211> LENGTH: 21
<212> TYPE: PRT
<213> ORGANISM: Artificial Sequence
<220> FEATURE:
<223> OTHER INFORMATION: Signal peptide HMM+38

<400> SEQUENCE: 14

Met Trp Trp Arg Leu Trp Trp Leu Leu Leu Leu Leu Leu Leu Leu Trp
1 5 10 15

Pro Met Val Trp Ala
20

<210> SEQ ID NO 15
<211> LENGTH: 23
<212> TYPE: PRT
<213> ORGANISM: Artificial Sequence
<220> FEATURE:
<223> OTHER INFORMATION: Signal peptide Exendin-4

<400> SEQUENCE: 15

Met Lys Ile Ile Leu Trp Leu Cys Val Phe Gly Leu Phe Leu Ala Thr
1 5 10 15

Leu Phe Pro Ile Ser Trp Gln
20

<210> SEQ ID NO 16
<211> LENGTH: 86
<212> TYPE: PRT
<213> ORGANISM: Artificial Sequence
<220> FEATURE:
<223> OTHER INFORMATION: Insulin precursor

<400> SEQUENCE: 16

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85


<210> SEQ ID NO 17
<211> LENGTH: 86
<212> TYPE: PRT
<213> ORGANISM: Artificial Sequence
<220> FEATURE:
<223> OTHER INFORMATION: Insulin precursor

<400> SEQUENCE: 17

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Glu Gln
65                  70                  75                  80

Leu Glu Asn Tyr Cys Asn
                85


<210> SEQ ID NO 18
<211> LENGTH: 92
<212> TYPE: PRT
<213> ORGANISM: Artificial Sequence
<220> FEATURE:
<223> OTHER INFORMATION: Insulin precursor

<400> SEQUENCE: 18

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Arg
            20                  25                  30

Ile Lys Arg Glu Ala Glu Asp Leu Gln Val Gly Gln Val Glu Leu Gly
        35                  40                  45

Gly Gly Pro Gly Ala Gly Ser Leu Gln Pro Leu Ala Leu Glu Gly Ser
    50                  55                  60

Leu Gln Lys Arg Ile Lys Arg Gly Ile Val Glu Gln Cys Cys Thr Ser
65                  70                  75                  80

Ile Cys Ser Leu Tyr Gln Leu Glu Asn Tyr Cys Asn
                85                  90


<210> SEQ ID NO 19
<211> LENGTH: 94
<212> TYPE: PRT
<213> ORGANISM: Artificial Sequence
```

<220> FEATURE:
<223> OTHER INFORMATION: Insulin precursor

<400> SEQUENCE: 19

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Asp Asp
            20                  25                  30

Asp Asp Lys Glu Ala Glu Asp Leu Gln Val Gly Gln Val Glu Leu Gly
        35                  40                  45

Gly Gly Pro Gly Ala Gly Ser Leu Gln Pro Leu Ala Leu Glu Gly Ser
    50                  55                  60

Leu Gln Lys Arg Asp Asp Asp Asp Lys Gly Ile Val Glu Gln Cys Cys
65                  70                  75                  80

Thr Ser Ile Cys Ser Leu Tyr Gln Leu Glu Asn Tyr Cys Asn
                85                  90

<210> SEQ ID NO 20
<211> LENGTH: 84
<212> TYPE: PRT
<213> ORGANISM: Artificial Sequence
<220> FEATURE:
<223> OTHER INFORMATION: Insulin precursor

<400> SEQUENCE: 20

Phe Val Asn Gln His Leu Cys Gly Ser His Leu Val Glu Ala Leu His
1               5                   10                  15

Leu Val Cys Gly Glu Arg Gly Phe His Tyr Thr Pro Lys Arg Glu Ala
            20                  25                  30

Glu Asp Leu Gln Val Gly Gln Val Glu Leu Gly Gly Gly Pro Gly Ala
        35                  40                  45

Gly Ser Leu Gln Pro Leu Ala Leu Glu Gly Ser Leu Gln Lys Arg Gly
    50                  55                  60

Ile Val Glu Gln Cys Cys Thr Ser Ile Cys Ser Leu Glu Gln Leu Glu
65                  70                  75                  80

Asn Tyr Cys Asn

<210> SEQ ID NO 21
<211> LENGTH: 83
<212> TYPE: PRT
<213> ORGANISM: Artificial Sequence
<220> FEATURE:
<223> OTHER INFORMATION: Insulin precursor

<400> SEQUENCE: 21

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys Arg Glu Ala
            20                  25                  30

Glu Asp Leu Gln Val Gly Gln Val Glu Leu Gly Gly Gly Pro Gly Ala
        35                  40                  45

Gly Ser Leu Gln Pro Leu Ala Leu Glu Gly Ser Leu Lys Arg Gly Ile
    50                  55                  60

Val Glu Gln Cys Cys Thr Ser Ile Cys Ser Leu Glu Gln Leu Glu Asn
65                  70                  75                  80

Tyr Cys Asn

<210> SEQ ID NO 22

<211> LENGTH: 84
<212> TYPE: PRT
<213> ORGANISM: Artificial Sequence
<220> FEATURE:
<223> OTHER INFORMATION: Insulin precursor

<400> SEQUENCE: 22

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Arg Glu Ala
            20                  25                  30

Glu Asp Leu Gln Val Gly Gln Val Glu Leu Gly Gly Gly Pro Gly Ala
        35                  40                  45

Gly Ser Leu Gln Pro Leu Ala Leu Glu Gly Ser Leu Gln Lys Arg Gly
    50                  55                  60

Ile Val Glu Gln Cys Cys Thr Ser Ile Cys Ser Leu Glu Gln Leu Glu
65                  70                  75                  80

Asn Tyr Cys Asn
```

<210> SEQ ID NO 23
<211> LENGTH: 27
<212> TYPE: PRT
<213> ORGANISM: Artificial Sequence
<220> FEATURE:
<223> OTHER INFORMATION: Linker GS-(G4S)5

<400> SEQUENCE: 23

```
Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser
            20                  25
```

<210> SEQ ID NO 24
<211> LENGTH: 25
<212> TYPE: PRT
<213> ORGANISM: Artificial Sequence
<220> FEATURE:
<223> OTHER INFORMATION: Linker (G4S)5

<400> SEQUENCE: 24

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 25
<211> LENGTH: 15
<212> TYPE: PRT
<213> ORGANISM: Artificial Sequence
<220> FEATURE:
<223> OTHER INFORMATION: Linker (G4S)3

<400> SEQUENCE: 25

```
Gly Gly Gly Gly Ser Gly Gly Gly Gly Ser Gly Gly Gly Gly Ser
1               5                   10                  15
```

<210> SEQ ID NO 26
<211> LENGTH: 55
<212> TYPE: PRT
<213> ORGANISM: Artificial Sequence
<220> FEATURE:
<223> OTHER INFORMATION: Linker GS-CTP

<400> SEQUENCE: 26

Gly Ser Gly Gly Gly Gly Ser Gly Gly Gly Gly Ser Gly Gly Gly Gly
1 5 10 15

Ser Gly Gly Gly Gly Ser Gly Gly Gly Gly Ser Ser Ser Ser Ser Lys
20 25 30

Ala Pro Pro Pro Ser Leu Pro Ser Pro Ser Arg Leu Pro Gly Pro Ser
35 40 45

Asp Thr Pro Ile Leu Pro Gln
50 55

<210> SEQ ID NO 27
<211> LENGTH: 28
<212> TYPE: PRT
<213> ORGANISM: Artificial Sequence
<220> FEATURE:
<223> OTHER INFORMATION: Linker CA

<400> SEQUENCE: 27

Ser Ala Ser Ser Lys Ala Pro Pro Pro Ser Leu Pro Ser Pro Ser Arg
1 5 10 15

Leu Pro Gly Pro Ser Asp Thr Pro Ile Leu Pro Gln
20 25

<210> SEQ ID NO 28
<211> LENGTH: 28
<212> TYPE: PRT
<213> ORGANISM: Artificial Sequence
<220> FEATURE:
<223> OTHER INFORMATION: Linker CTP

<400> SEQUENCE: 28

Ser Ser Ser Ser Lys Ala Pro Pro Pro Ser Leu Pro Ser Pro Ser Arg
1 5 10 15

Leu Pro Gly Pro Ser Asp Thr Pro Ile Leu Pro Gln
20 25

<210> SEQ ID NO 29
<211> LENGTH: 56
<212> TYPE: PRT
<213> ORGANISM: Artificial Sequence
<220> FEATURE:
<223> OTHER INFORMATION: Linker 2CTP

<400> SEQUENCE: 29

Ser Ala Ser Ser Lys Ala Pro Pro Pro Ser Leu Pro Ser Pro Ser Arg
1 5 10 15

Leu Pro Gly Pro Ser Asp Thr Pro Ile Leu Pro Gln Ser Ser Ser Ser
20 25 30

Lys Ala Pro Pro Pro Ser Leu Pro Ser Pro Ser Arg Leu Pro Gly Pro
35 40 45

Ser Asp Thr Pro Ile Leu Pro Gln
50 55

<210> SEQ ID NO 30
<211> LENGTH: 17
<212> TYPE: PRT
<213> ORGANISM: Artificial Sequence
<220> FEATURE:
<223> OTHER INFORMATION: Linker C1

<400> SEQUENCE: 30

Val Ala Pro Pro Pro Ala Leu Pro Ala Pro Val Arg Leu Pro Gly Pro
1 5 10 15

Ala

<210> SEQ ID NO 31
<211> LENGTH: 49
<212> TYPE: PRT
<213> ORGANISM: Artificial Sequence
<220> FEATURE:
<223> OTHER INFORMATION: Linker C1C

<400> SEQUENCE: 31

Gly Gly Gly Ser Val Ala Pro Pro Pro Ala Leu Pro Ala Pro Val Arg
1               5                   10                  15

Leu Pro Gly Pro Ala Ser Ser Ser Ser Lys Ala Pro Pro Pro Ser Leu
            20                  25                  30

Pro Ser Pro Ser Arg Leu Pro Gly Pro Ser Asp Thr Pro Ile Leu Pro
        35                  40                  45

Gln

<210> SEQ ID NO 32
<211> LENGTH: 38
<212> TYPE: PRT
<213> ORGANISM: Artificial Sequence
<220> FEATURE:
<223> OTHER INFORMATION: Linker 2C1

<400> SEQUENCE: 32

Gly Gly Gly Ser Val Ala Pro Pro Pro Ala Leu Pro Ala Pro Val Arg
1               5                   10                  15

Leu Pro Gly Pro Ala Val Ala Pro Pro Pro Ala Leu Pro Ala Pro Val
            20                  25                  30

Arg Leu Pro Gly Pro Ala
        35

<210> SEQ ID NO 33
<211> LENGTH: 50
<212> TYPE: PRT
<213> ORGANISM: Artificial Sequence
<220> FEATURE:
<223> OTHER INFORMATION: Linker C2C

<400> SEQUENCE: 33

Gly Gly Gly Ser Val Ala Pro Pro Pro Ala Leu Pro Ala Val Ala Pro
1               5                   10                  15

Pro Pro Ala Leu Pro Ala Ser Ser Ser Ser Lys Ala Pro Pro Pro Ser
            20                  25                  30

Leu Pro Ser Pro Ser Arg Leu Pro Gly Pro Ser Asp Thr Pro Ile Leu
        35                  40                  45

Pro Gln
    50

<210> SEQ ID NO 34
<211> LENGTH: 55
<212> TYPE: PRT
<213> ORGANISM: Artificial Sequence
<220> FEATURE:
<223> OTHER INFORMATION: Linker 3C1

<400> SEQUENCE: 34

Gly Gly Ala Ala Val Ala Pro Pro Pro Ala Leu Pro Ala Pro Val Arg
1               5                   10                  15

Leu Pro Gly Pro Ala Val Ala Pro Pro Pro Ala Leu Pro Ala Pro Val

```
            20                  25                  30

Arg Leu Pro Gly Pro Ala Val Ala Pro Pro Pro Ala Leu Pro Ala Pro
        35                  40                  45

Val Arg Leu Pro Gly Pro Ala
    50                  55


<210> SEQ ID NO 35
<211> LENGTH: 38
<212> TYPE: PRT
<213> ORGANISM: Artificial Sequence
<220> FEATURE:
<223> OTHER INFORMATION: Linker 2C1A

<400> SEQUENCE: 35

Gly Gly Ala Ala Val Ala Pro Pro Pro Ala Leu Pro Ala Pro Val Arg
1               5                   10                  15

Leu Pro Gly Pro Ala Val Ala Pro Pro Pro Ala Leu Pro Ala Pro Val
            20                  25                  30

Arg Leu Pro Gly Pro Ala
        35


<210> SEQ ID NO 36
<211> LENGTH: 231
<212> TYPE: PRT
<213> ORGANISM: Artificial Sequence
<220> FEATURE:
<223> OTHER INFORMATION: Fc1

<400> SEQUENCE: 36

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

```
Ser Leu Ser Leu Ser Pro Gly
225                 230


<210> SEQ ID NO 37
<211> LENGTH: 223
<212> TYPE: PRT
<213> ORGANISM: Artificial Sequence
<220> FEATURE:
<223> OTHER INFORMATION: Fc2

<400> SEQUENCE: 37

Val Glu Cys Pro Pro Cys Pro Ala Pro Pro Val Ala Gly Pro Ser Val
1               5                   10                  15

Phe Leu Phe Pro Pro Lys Pro Lys Asp Gln Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Leu His Glu Ala Leu
        195                 200                 205

His Asn His Tyr Thr Gln Lys Ser Leu Ser Leu Ser Pro Gly Lys
    210                 215                 220


<210> SEQ ID NO 38
<211> LENGTH: 228
<212> TYPE: PRT
<213> ORGANISM: Artificial Sequence
<220> FEATURE:
<223> OTHER INFORMATION: Fc3

<400> SEQUENCE: 38

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80
```

```
Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225


<210> SEQ ID NO 39
<211> LENGTH: 223
<212> TYPE: PRT
<213> ORGANISM: Artificial Sequence
<220> FEATURE:
<223> OTHER INFORMATION: Fc4

<400> SEQUENCE: 39

Val Glu Cys Pro Pro Cys Pro Ala Pro Pro Val Ala Gly Pro Ser Val
1               5                   10                  15

Phe Leu Phe Pro Pro Lys Pro Lys Asp Gln Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Ala Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Leu His Glu Ala Leu
        195                 200                 205
```

His Asn His Tyr Thr Gln Lys Ser Leu Ser Leu Ser Pro Gly Lys
210 215 220

<210> SEQ ID NO 40
<211> LENGTH: 223
<212> TYPE: PRT
<213> ORGANISM: Artificial Sequence
<220> FEATURE:
<223> OTHER INFORMATION: Fc5

<400> SEQUENCE: 40

Val Glu Cys Pro Pro Cys Pro Ala Pro Pro Val Ala Gly Pro Ser Val
1 5 10 15

Phe Leu Phe Pro Pro Lys Pro Lys Asp Thr Leu Tyr Ile Thr Arg Glu
20 25 30

Pro Glu Val Thr Cys Val Val Val Asp Val Ser His Glu Asp Pro Glu
35 40 45

Val Gln Phe Asn Trp Tyr Val Asp Gly Val Glu Val His Asn Ala Lys
50 55 60

Thr Lys Pro Arg Glu Glu Gln Phe Ala Ser Thr Phe Arg Val Val Ser
65 70 75 80

Val Leu Thr Val Val His Gln Asp Trp Leu Asn Gly Lys Glu Tyr Lys
85 90 95

Cys Lys Val Ser Asn Lys Gly Leu Pro Ala Pro Ile Glu Lys Thr Ile
100 105 110

Ser Lys Thr Lys Gly Gln Pro Arg Glu Pro Gln Val Tyr Thr Leu Pro
115 120 125

Pro Ser Arg Glu Glu Met Thr Lys Asn Gln Val Ser Leu Thr Cys Leu
130 135 140

Val Lys Gly Phe Tyr Pro Ser Asp Ile Ala Val Glu Trp Glu Ser Asn
145 150 155 160

Gly Gln Pro Glu Asn Asn Tyr Lys Thr Thr Pro Pro Met Leu Asp Ser
165 170 175

Asp Gly Ser Phe Phe Leu Tyr Ser Lys Leu Thr Val Asp Lys Ser Arg
180 185 190

Trp Gln Gln Gly Asn Val Phe Ser Cys Ser Val Met His Glu Ala Leu
195 200 205

His Asn His Tyr Thr Gln Lys Ser Leu Ser Leu Ser Pro Gly Lys
210 215 220

<210> SEQ ID NO 41
<211> LENGTH: 223
<212> TYPE: PRT
<213> ORGANISM: Artificial Sequence
<220> FEATURE:
<223> OTHER INFORMATION: Fc6

<400> SEQUENCE: 41

Val Glu Cys Pro Pro Cys Pro Ala Pro Pro Val Ala Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Gln Phe Asn Trp Tyr Val Asp Gly Val Glu Val His Asn Ala Lys
50 55 60

Thr Lys Pro Arg Glu Glu Gln Phe Ala Ser Thr Phe Arg Val Val Ser 65 70 75 80

Val Leu Thr Val Val His Gln Asp Trp Leu Asn Gly Lys Glu Tyr Lys
85 90 95

Cys Lys Val Ser Asn Lys Gly Leu Pro Ala Pro Ile Glu Lys Thr Ile
100 105 110

Ser Lys Thr Lys Gly Gln Pro Arg Glu Pro Gln Val Tyr Thr Leu Pro
115 120 125

Pro Ser Arg Glu Glu Met Thr Lys Asn Gln Val Ser Leu Thr Cys Leu
130 135 140

Val Lys Gly Phe Tyr Pro Ser Asp Ile Ala Val Glu Trp Glu Ser Asn
145 150 155 160

Gly Gln Pro Glu Asn Asn Tyr Lys Thr Thr Pro Pro Met Leu Asp Ser
165 170 175

Asp Gly Ser Phe Phe Leu Tyr Ser Lys Leu Thr Val Asp Lys Ser Arg
180 185 190

Trp Gln Gln Gly Asn Val Phe Ser Cys Ser Val Leu His Glu Ala Leu
195 200 205

His Ser His Tyr Thr Gln Lys Ser Leu Ser Leu Ser Pro Gly Lys
210 215 220

<210> SEQ ID NO 42
<211> LENGTH: 223
<212> TYPE: PRT
<213> ORGANISM: Artificial Sequence
<220> FEATURE:
<223> OTHER INFORMATION: Fc7

<400> SEQUENCE: 42

Val Glu Cys Pro Pro Cys Pro Ala Pro Pro Val Ala Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Gln Phe Asn Trp Tyr Val Asp Gly Val Glu Val His Asn Ala Lys
50 55 60

Thr Lys Pro Arg Glu Glu Gln Phe Ala Ser Thr Phe Arg Val Val Ser
65 70 75 80

Val Leu Thr Val Val His Gln Asp Trp Leu Asn Gly Lys Glu Tyr Lys
85 90 95

Cys Lys Val Ser Asn Lys Gly Leu Pro Ala Pro Ile Glu Lys Thr Ile
100 105 110

Ser Lys Thr Lys Gly Gln Pro Arg Glu Pro Gln Val Tyr Thr Leu Pro
115 120 125

Pro Ser Arg Glu Glu Met Thr Lys Asn Gln Val Ser Leu Thr Cys Leu
130 135 140

Val Lys Gly Phe Tyr Pro Ser Asp Ile Ala Val Glu Trp Glu Ser Asn
145 150 155 160

Gly Gln Pro Glu Asn Asn Tyr Lys Thr Thr Pro Pro Met Leu Asp Ser
165 170 175

Asp Gly Ser Phe Phe Leu Tyr Ser Lys Leu Thr Val Asp Lys Ser Arg
180 185 190

Trp Gln Gln Gly Asn Val Phe Ser Cys Ser Val Leu His Glu Ala Leu
195 200 205

His Ser His Tyr Thr Gln Lys Ser Leu Ser Leu Ser Pro Gly Lys 210 215 220

<210> SEQ ID NO 43
<211> LENGTH: 228
<212> TYPE: PRT
<213> ORGANISM: Artificial Sequence
<220> FEATURE:
<223> OTHER INFORMATION: Fc8

<400> SEQUENCE: 43

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Tyr Ile Thr Arg Glu Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Ala Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225
```

<210> SEQ ID NO 44
<211> LENGTH: 228
<212> TYPE: PRT
<213> ORGANISM: Artificial Sequence
<220> FEATURE:
<223> OTHER INFORMATION: Fc9

<400> SEQUENCE: 44

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

```
Glu Val His Asn Ala Lys Thr Lys Pro Arg Glu Glu Gln Phe Ala Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Leu His Glu Ala Leu His Ser His Tyr Thr Gln Lys Ser Leu Ser
    210                 215                 220

Leu Ser Leu Gly
225


<210> SEQ ID NO 45
<211> LENGTH: 228
<212> TYPE: PRT
<213> ORGANISM: Artificial Sequence
<220> FEATURE:
<223> OTHER INFORMATION: Fc15

<400> SEQUENCE: 45

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190
```

```
Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225


<210> SEQ ID NO 46
<211> LENGTH: 223
<212> TYPE: PRT
<213> ORGANISM: Artificial Sequence
<220> FEATURE:
<223> OTHER INFORMATION: Fc16

<400> SEQUENCE: 46

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220


<210> SEQ ID NO 47
<211> LENGTH: 372
<212> TYPE: PRT
<213> ORGANISM: Artificial Sequence
<220> FEATURE:
<223> OTHER INFORMATION: Fusion protein SS302-001

<400> SEQUENCE: 47

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45
```

```
Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Ser Gly Gly Gly Gly Ser Gly Gly Gly
                85                  90                  95

Gly Ser Gly Gly Gly Gly Ser Gly Gly Gly Gly Ser Gly Gly Gly Gly
            100                 105                 110

Ser Ser Ser Ser Ser Lys Ala Pro Pro Pro Ser Leu Pro Ser Pro Ser
        115                 120                 125

Arg Leu Pro Gly Pro Ser Asp Thr Pro Ile Leu Pro Gln Glu Pro Lys
    130                 135                 140

Ser Cys Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Asp Glu Leu Thr Lys Asn Gln
        275                 280                 285

Val Ser Leu Thr Cys Leu Val Lys Gly Phe Tyr Pro Ser Asp Ile Ala
    290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser
        355                 360                 365

Leu Ser Pro Gly
    370


<210> SEQ ID NO 48
<211> LENGTH: 364
<212> TYPE: PRT
<213> ORGANISM: Artificial Sequence
<220> FEATURE:
<223> OTHER INFORMATION: Fusion protein SS302-002

<400> SEQUENCE: 48

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```

```
Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Ser Gly Gly Gly Gly Ser Gly Gly Gly
                85                  90                  95

Gly Ser Gly Gly Gly Gly Ser Gly Gly Gly Gly Ser Gly Gly Gly Gly
            100                 105                 110

Ser Ser Ser Ser Ser Lys Ala Pro Pro Pro Ser Leu Pro Ser Pro Ser
        115                 120                 125

Arg Leu Pro Gly Pro Ser Asp Thr Pro Ile Leu Pro Gln Val Glu Cys
    130                 135                 140

Pro Pro Cys Pro Ala Pro Pro Val Ala Gly Pro Ser Val Phe Leu Phe
145                 150                 155                 160

Pro Pro Lys Pro Lys Asp Gln Leu Met Ile Ser Arg Thr Pro Glu Val
                165                 170                 175

Thr Cys Val Val Val Asp Val Ser His Glu Asp Pro Glu Val Gln Phe
            180                 185                 190

Asn Trp Tyr Val Asp Gly Val Glu Val His Asn Ala Lys Thr Lys Pro
        195                 200                 205

Arg Glu Glu Gln Phe Asn Ser Thr Phe Arg Val Val Ser Val Leu Thr
    210                 215                 220

Val Val His Gln Asp Trp Leu Asn Gly Lys Glu Tyr Lys Cys Lys Val
225                 230                 235                 240

Ser Asn Lys Gly Leu Pro Ala Ser Ile Glu Lys Thr Ile Ser Lys Thr
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Met Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Leu His Glu Ala Leu His Asn His
            340                 345                 350

Tyr Thr Gln Lys Ser Leu Ser Leu Ser Pro Gly Lys
        355                 360
```

<210> SEQ ID NO 49
<211> LENGTH: 369
<212> TYPE: PRT
<213> ORGANISM: Artificial Sequence
<220> FEATURE:
<223> OTHER INFORMATION: Fusion protein SS302-003

<400> SEQUENCE: 49

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```

```
Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Ser Gly Gly Gly Gly Ser Gly Gly Gly
                85                  90                  95

Gly Ser Gly Gly Gly Gly Ser Gly Gly Gly Gly Ser Gly Gly Gly Gly
            100                 105                 110

Ser Ser Ser Ser Ser Lys Ala Pro Pro Pro Ser Leu Pro Ser Pro Ser
        115                 120                 125

Arg Leu Pro Gly Pro Ser Asp Thr Pro Ile Leu Pro Gln Glu Ser Lys
    130                 135                 140

Tyr Gly Pro Pro Cys Pro Pro Cys Pro Ala Pro Glu Phe Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser Gln Glu
            180                 185                 190

Asp Pro Glu Val Gln Phe Asn Trp Tyr Val Asp Gly Val Glu Val His
        195                 200                 205

Asn Ala Lys Thr Lys Pro Arg Glu Glu Gln Phe Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Gly Leu Pro Ser Ser Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Gln Glu Glu Met Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Arg Leu Thr Val Asp
                325                 330                 335

Lys Ser Arg Trp Gln Glu Gly Asn Val Phe Ser Cys Ser Val Met His
            340                 345                 350

Glu Ala Leu His Asn His Tyr Thr Gln Lys Ser Leu Ser Leu Ser Leu
        355                 360                 365

Gly


<210> SEQ ID NO 50
<211> LENGTH: 336
<212> TYPE: PRT
<213> ORGANISM: Artificial Sequence
<220> FEATURE:
<223> OTHER INFORMATION: Fusion protein SS302-004

<400> SEQUENCE: 50

Phe Val Asn Gln His Leu Cys Gly Ser His Leu Val Glu Ala Leu Tyr
1               5                   10                  15
```

```
Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Ser Gly Gly Gly Gly Ser Gly Gly Gly
                85                  90                  95

Gly Ser Gly Gly Gly Gly Ser Gly Gly Gly Gly Ser Gly Gly Gly Gly
            100                 105                 110

Ser Val Glu Cys Pro Pro Cys Pro Ala Pro Pro Val Ala Gly Pro Ser
        115                 120                 125

Val Phe Leu Phe Pro Pro Lys Pro Lys Asp Gln Leu Met Ile Ser Arg
    130                 135                 140

Thr Pro Glu Val Thr Cys Val Val Val Asp Val Ser His Glu Asp Pro
145                 150                 155                 160

Glu Val Gln Phe Asn Trp Tyr Val Asp Gly Val Glu Val His Asn Ala
                165                 170                 175

Lys Thr Lys Pro Arg Glu Glu Gln Phe Asn Ser Thr Phe Arg Val Val
            180                 185                 190

Ser Val Leu Thr Val Val His Gln Asp Trp Leu Asn Gly Lys Glu Tyr
        195                 200                 205

Lys Cys Lys Val Ser Asn Lys Gly Leu Pro Ala Ser Ile Glu Lys Thr
    210                 215                 220

Ile Ser Lys Thr Lys Gly Gln Pro Arg Glu Pro Gln Val Tyr Thr Leu
225                 230                 235                 240

Pro Pro Ser Arg Glu Glu Met Thr Lys Asn Gln Val Ser Leu Thr Cys
                245                 250                 255

Leu Val Lys Gly Phe Tyr Pro Ser Asp Ile Ala Val Glu Trp Glu Ser
            260                 265                 270

Asn Gly Gln Pro Glu Asn Asn Tyr Lys Thr Thr Pro Pro Met Leu Asp
        275                 280                 285

Ser Asp Gly Ser Phe Phe Leu Tyr Ser Lys Leu Thr Val Asp Lys Ser
    290                 295                 300

Arg Trp Gln Gln Gly Asn Val Phe Ser Cys Ser Val Leu His Glu Ala
305                 310                 315                 320

Leu His Asn His Tyr Thr Gln Lys Ser Leu Ser Leu Ser Pro Gly Lys
                325                 330                 335


<210> SEQ ID NO 51
<211> LENGTH: 334
<212> TYPE: PRT
<213> ORGANISM: Artificial Sequence
<220> FEATURE:
<223> OTHER INFORMATION: Fusion protein SS302-005

<400> SEQUENCE: 51

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45
```

Gly Ala Gly Ser Leu Gln Pro Leu Ala Leu Glu Gly Ser Leu Gln Lys
50 55 60

Arg Gly Ile Val Glu Gln Cys Cys Thr Ser Ile Cys Ser Leu Tyr Gln
65 70 75 80

Leu Glu Asn Tyr Cys Asn Gly Gly Gly Gly Ser Gly Gly Gly Gly Ser
85 90 95

Gly Gly Gly Gly Ser Gly Gly Gly Gly Ser Gly Gly Gly Gly Ser Val
100 105 110

Glu Cys Pro Pro Cys Pro Ala Pro Pro Val Ala Gly Pro Ser Val Phe
115 120 125

Leu Phe Pro Pro Lys Pro Lys Asp Gln Leu Met Ile Ser Arg Thr Pro
130 135 140

Glu Val Thr Cys Val Val Val Asp Val Ser His Glu Asp Pro Glu Val
145 150 155 160

Gln Phe Asn Trp Tyr Val Asp Gly Val Glu Val His Asn Ala Lys Thr
165 170 175

Lys Pro Arg Glu Glu Gln Phe Ala Ser Thr Phe Arg Val Val Ser Val
180 185 190

Leu Thr Val Val His Gln Asp Trp Leu Asn Gly Lys Glu Tyr Lys Cys
195 200 205

Lys Val Ser Asn Lys Gly Leu Pro Ala Ser Ile Glu Lys Thr Ile Ser
210 215 220

Lys Thr Lys Gly Gln Pro Arg Glu Pro Gln Val Tyr Thr Leu Pro Pro
225 230 235 240

Ser Arg Glu Glu Met Thr Lys Asn Gln Val Ser Leu Thr Cys Leu Val
245 250 255

Lys Gly Phe Tyr Pro Ser Asp Ile Ala Val Glu Trp Glu Ser Asn Gly
260 265 270

Gln Pro Glu Asn Asn Tyr Lys Thr Thr Pro Pro Met Leu Asp Ser Asp
275 280 285

Gly Ser Phe Phe Leu Tyr Ser Lys Leu Thr Val Asp Lys Ser Arg Trp
290 295 300

Gln Gln Gly Asn Val Phe Ser Cys Ser Val Leu His Glu Ala Leu His
305 310 315 320

Asn His Tyr Thr Gln Lys Ser Leu Ser Leu Ser Pro Gly Lys
325 330

<210> SEQ ID NO 52
<211> LENGTH: 337
<212> TYPE: PRT
<213> ORGANISM: Artificial Sequence
<220> FEATURE:
<223> OTHER INFORMATION: Fusion protein SS302-006

<400> SEQUENCE: 52

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr Arg Arg
20 25 30

Glu Ala Glu Asp Leu Gln Val Gly Gln Val Glu Leu Gly Gly Gly Pro
35 40 45

Gly Ala Gly Ser Leu Gln Pro Leu Ala Leu Glu Gly Ser Leu Gln Lys
50 55 60

Arg Gly Ile Val Glu Gln Cys Cys Thr Ser Ile Cys Ser Leu Tyr Gln
65 70 75 80

```
Leu Glu Asn Tyr Cys Asn Ser Ala Ser Ser Lys Ala Pro Pro Pro Ser
                85                  90                  95

Leu Pro Ser Pro Ser Arg Leu Pro Gly Pro Ser Asp Thr Pro Ile Leu
            100                 105                 110

Pro Gln Val Glu Cys Pro Pro Cys Pro Ala Pro Pro Val Ala Gly Pro
        115                 120                 125

Ser Val Phe Leu Phe Pro Pro Lys Pro Lys Asp Thr Leu Met Ile Ser
    130                 135                 140

Arg Thr Pro Glu Val Thr Cys Val Val Val Asp Val Ser His Glu Asp
145                 150                 155                 160

Pro Glu Val Gln Phe Asn Trp Tyr Val Asp Gly Val Glu Val His Asn
                165                 170                 175

Ala Lys Thr Lys Pro Arg Glu Glu Gln Phe Asn Ser Thr Phe Arg Val
            180                 185                 190

Val Ser Val Leu Thr Val Val His Gln Asp Trp Leu Asn Gly Lys Glu
        195                 200                 205

Tyr Lys Cys Lys Val Ser Asn Lys Gly Leu Pro Ala Pro Ile Glu Lys
    210                 215                 220

Thr Ile Ser Lys Thr Lys Gly Gln Pro Arg Glu Pro Gln Val Tyr Thr
225                 230                 235                 240

Leu Pro Pro Ser Arg Glu Glu Met Thr Lys Asn Gln Val Ser Leu Thr
                245                 250                 255

Cys Leu Val Lys Gly Phe Tyr Pro Ser Asp Ile Ala Val Glu Trp Glu
            260                 265                 270

Ser Asn Gly Gln Pro Glu Asn Asn Tyr Lys Thr Thr Pro Pro Met Leu
        275                 280                 285

Asp Ser Asp Gly Ser Phe Phe Leu Tyr Ser Lys Leu Thr Val Asp Lys
    290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

Lys


<210> SEQ ID NO 53
<211> LENGTH: 337
<212> TYPE: PRT
<213> ORGANISM: Artificial Sequence
<220> FEATURE:
<223> OTHER INFORMATION: Fusion protein SS302-007

<400> SEQUENCE: 53

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Ser Ser Ser Ser Lys Ala Pro Pro Pro Ser
                85                  90                  95

Leu Pro Ser Pro Ser Arg Leu Pro Gly Pro Ser Asp Thr Pro Ile Leu
```

```
            100                 105                 110

Pro Gln Val Glu Cys Pro Pro Cys Pro Ala Pro Pro Val Ala Gly Pro
        115                 120                 125

Ser Val Phe Leu Phe Pro Pro Lys Pro Lys Asp Thr Leu Met Ile Ser
    130                 135                 140

Arg Thr Pro Glu Val Thr Cys Val Val Val Asp Val Ser His Glu Asp
145                 150                 155                 160

Pro Glu Val Gln Phe Asn Trp Tyr Val Asp Gly Val Glu Val His Asn
                165                 170                 175

Ala Lys Thr Lys Pro Arg Glu Glu Gln Phe Asn Ser Thr Phe Arg Val
            180                 185                 190

Val Ser Val Leu Thr Val Val His Gln Asp Trp Leu Asn Gly Lys Glu
        195                 200                 205

Tyr Lys Cys Lys Val Ser Asn Lys Gly Leu Pro Ala Pro Ile Glu Lys
    210                 215                 220

Thr Ile Ser Lys Thr Lys Gly Gln Pro Arg Glu Pro Gln Val Tyr Thr
225                 230                 235                 240

Leu Pro Pro Ser Arg Glu Glu Met Thr Lys Asn Gln Val Ser Leu Thr
                245                 250                 255

Cys Leu Val Lys Gly Phe Tyr Pro Ser Asp Ile Ala Val Glu Trp Glu
            260                 265                 270

Ser Asn Gly Gln Pro Glu Asn Asn Tyr Lys Thr Thr Pro Pro Met Leu
        275                 280                 285

Asp Ser Asp Gly Ser Phe Phe Leu Tyr Ser Lys Leu Thr Val Asp Lys
    290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

Lys


<210> SEQ ID NO 54
<211> LENGTH: 365
<212> TYPE: PRT
<213> ORGANISM: Artificial Sequence
<220> FEATURE:
<223> OTHER INFORMATION: Fusion protein SS302-008

<400> SEQUENCE: 54

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Ser Ala Ser Ser Lys Ala Pro Pro Pro Ser
                85                  90                  95

Leu Pro Ser Pro Ser Arg Leu Pro Gly Pro Ser Asp Thr Pro Ile Leu
            100                 105                 110

Pro Gln Ser Ser Ser Ser Lys Ala Pro Pro Pro Ser Leu Pro Ser Pro
        115                 120                 125
```

```
Ser Arg Leu Pro Gly Pro Ser Asp Thr Pro Ile Leu Pro Gln Val Glu
    130                 135                 140

Cys Pro Pro Cys Pro Ala Pro Pro Val Ala Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Gln
            180                 185                 190

Phe Asn Trp Tyr Val Asp Gly Val Glu Val His Asn Ala Lys Thr Lys
        195                 200                 205

Pro Arg Glu Glu Gln Phe Asn Ser Thr Phe Arg Val Val Ser Val Leu
    210                 215                 220

Thr Val Val His Gln Asp Trp Leu Asn Gly Lys Glu Tyr Lys Cys Lys
225                 230                 235                 240

Val Ser Asn Lys Gly Leu Pro Ala Pro Ile Glu Lys Thr Ile Ser Lys
                245                 250                 255

Thr Lys Gly Gln Pro Arg Glu Pro Gln Val Tyr Thr Leu Pro Pro Ser
            260                 265                 270

Arg Glu Glu Met Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
    290                 295                 300

Pro Glu Asn Asn Tyr Lys Thr Thr Pro Pro Met Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Lys
        355                 360                 365


<210> SEQ ID NO 55
<211> LENGTH: 358
<212> TYPE: PRT
<213> ORGANISM: Artificial Sequence
<220> FEATURE:
<223> OTHER INFORMATION: Fusion protein SS302-009

<400> SEQUENCE: 55

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Gly Gly Ser Val Ala Pro Pro Pro Ala
                85                  90                  95

Leu Pro Ala Pro Val Arg Leu Pro Gly Pro Ala Ser Ser Ser Ser Lys
            100                 105                 110

Ala Pro Pro Pro Ser Leu Pro Ser Pro Ser Arg Leu Pro Gly Pro Ser
        115                 120                 125
```

```
Asp Thr Pro Ile Leu Pro Gln Val Glu Cys Pro Pro Cys Pro Ala Pro
    130                 135                 140

Pro Val Ala Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Gln Phe Asn Trp Tyr Val Asp Gly
            180                 185                 190

Val Glu Val His Asn Ala Lys Thr Lys Pro Arg Glu Glu Gln Phe Asn
        195                 200                 205

Ser Thr Phe Arg Val Val Ser Val Leu Thr Val Val His Gln Asp Trp
    210                 215                 220

Leu Asn Gly Lys Glu Tyr Lys Cys Lys Val Ser Asn Lys Gly Leu Pro
225                 230                 235                 240

Ala Pro Ile Glu Lys Thr Ile Ser Lys Thr Lys Gly Gln Pro Arg Glu
                245                 250                 255

Pro Gln Val Tyr Thr Leu Pro Pro Ser Arg Glu Glu Met Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Met Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355
```

<210> SEQ ID NO 56
<211> LENGTH: 359
<212> TYPE: PRT
<213> ORGANISM: Artificial Sequence
<220> FEATURE:
<223> OTHER INFORMATION: Fusion protein SS302-011

<400> SEQUENCE: 56

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Gly Gly Ser Val Ala Pro Pro Pro Ala
                85                  90                  95

Leu Pro Ala Val Ala Pro Pro Pro Ala Leu Pro Ala Ser Ser Ser Ser
            100                 105                 110

Lys Ala Pro Pro Pro Ser Leu Pro Ser Pro Ser Arg Leu Pro Gly Pro
        115                 120                 125
```

```
Ser Asp Thr Pro Ile Leu Pro Gln Val Glu Cys Pro Pro Cys Pro Ala
    130                 135                 140

Pro Pro Val Ala Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Gln Phe Asn Trp Tyr Val Asp
            180                 185                 190

Gly Val Glu Val His Asn Ala Lys Thr Lys Pro Arg Glu Glu Gln Phe
        195                 200                 205

Asn Ser Thr Phe Arg Val Val Ser Val Leu Thr Val Val His Gln Asp
    210                 215                 220

Trp Leu Asn Gly Lys Glu Tyr Lys Cys Lys Val Ser Asn Lys Gly Leu
225                 230                 235                 240

Pro Ala Pro Ile Glu Lys Thr Ile Ser Lys Thr Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Met Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355


<210> SEQ ID NO 57
<211> LENGTH: 347
<212> TYPE: PRT
<213> ORGANISM: Artificial Sequence
<220> FEATURE:
<223> OTHER INFORMATION: Fusion protein SS302-012

<400> SEQUENCE: 57

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Gly Gly Ser Val Ala Pro Pro Pro Ala
                85                  90                  95

Leu Pro Ala Pro Val Arg Leu Pro Gly Pro Ala Val Ala Pro Pro Pro
            100                 105                 110

Ala Leu Pro Ala Pro Val Arg Leu Pro Gly Pro Ala Val Glu Cys Pro
        115                 120                 125
```

```
Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ala Pro Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345
```

```
<210> SEQ ID NO 58
<211> LENGTH: 364
<212> TYPE: PRT
<213> ORGANISM: Artificial Sequence
<220> FEATURE:
<223> OTHER INFORMATION: Fusion protein SS302-013

<400> SEQUENCE: 58

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Gly Ala Ala Val Ala Pro Pro Pro Ala
                85                  90                  95

Leu Pro Ala Pro Val Arg Leu Pro Gly Pro Ala Val Ala Pro Pro Pro
            100                 105                 110

Ala Leu Pro Ala Pro Val Arg Leu Pro Gly Pro Ala Val Ala Pro Pro
        115                 120                 125

Pro Ala Leu Pro Ala Pro Val Arg Leu Pro Gly Pro Ala Val Glu Cys
    130                 135                 140
```

```
Pro Pro Cys Pro Ala Pro Pro Val Ala Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Gln Phe
            180                 185                 190

Asn Trp Tyr Val Asp Gly Val Glu Val His Asn Ala Lys Thr Lys Pro
        195                 200                 205

Arg Glu Glu Gln Phe Asn Ser Thr Phe Arg Val Val Ser Val Leu Thr
    210                 215                 220

Val Val His Gln Asp Trp Leu Asn Gly Lys Glu Tyr Lys Cys Lys Val
225                 230                 235                 240

Ser Asn Lys Gly Leu Pro Ala Pro Ile Glu Lys Thr Ile Ser Lys Thr
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Met Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360


<210> SEQ ID NO 59
<211> LENGTH: 364
<212> TYPE: PRT
<213> ORGANISM: Artificial Sequence
<220> FEATURE:
<223> OTHER INFORMATION: Fusion protein SS302-014

<400> SEQUENCE: 59

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Gly Ala Ala Val Ala Pro Pro Pro Ala
                85                  90                  95

Leu Pro Ala Pro Val Arg Leu Pro Gly Pro Ala Val Ala Pro Pro Pro
            100                 105                 110

Ala Leu Pro Ala Pro Val Arg Leu Pro Gly Pro Ala Val Ala Pro Pro
        115                 120                 125

Pro Ala Leu Pro Ala Pro Val Arg Leu Pro Gly Pro Ala Val Glu Cys
    130                 135                 140
```

```
Pro Pro Cys Pro Ala Pro Pro Val Ala Gly Pro Ser Val Phe Leu Phe
145                 150                 155                 160

Pro Pro Lys Pro Lys Asp Thr Leu Tyr Ile Thr Arg Glu Pro Glu Val
                165                 170                 175

Thr Cys Val Val Val Asp Val Ser His Glu Asp Pro Glu Val Gln Phe
            180                 185                 190

Asn Trp Tyr Val Asp Gly Val Glu Val His Asn Ala Lys Thr Lys Pro
        195                 200                 205

Arg Glu Glu Gln Phe Ala Ser Thr Phe Arg Val Val Ser Val Leu Thr
    210                 215                 220

Val Val His Gln Asp Trp Leu Asn Gly Lys Glu Tyr Lys Cys Lys Val
225                 230                 235                 240

Ser Asn Lys Gly Leu Pro Ala Pro Ile Glu Lys Thr Ile Ser Lys Thr
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Met Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360


<210> SEQ ID NO 60
<211> LENGTH: 364
<212> TYPE: PRT
<213> ORGANISM: Artificial Sequence
<220> FEATURE:
<223> OTHER INFORMATION: Fusion protein SS302-015

<400> SEQUENCE: 60

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Gly Ala Ala Val Ala Pro Pro Pro Ala
                85                  90                  95

Leu Pro Ala Pro Val Arg Leu Pro Gly Pro Ala Val Ala Pro Pro Pro
            100                 105                 110

Ala Leu Pro Ala Pro Val Arg Leu Pro Gly Pro Ala Val Ala Pro Pro
        115                 120                 125

Pro Ala Leu Pro Ala Pro Val Arg Leu Pro Gly Pro Ala Val Glu Cys
    130                 135                 140
```

```
Pro Pro Cys Pro Ala Pro Pro Val Ala Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Gln Phe
            180                 185                 190

Asn Trp Tyr Val Asp Gly Val Glu Val His Asn Ala Lys Thr Lys Pro
        195                 200                 205

Arg Glu Glu Gln Phe Ala Ser Thr Phe Arg Val Val Ser Val Leu Thr
    210                 215                 220

Val Val His Gln Asp Trp Leu Asn Gly Lys Glu Tyr Lys Cys Lys Val
225                 230                 235                 240

Ser Asn Lys Gly Leu Pro Ala Pro Ile Glu Lys Thr Ile Ser Lys Thr
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Met Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Leu His Glu Ala Leu His Ser His
            340                 345                 350

Tyr Thr Gln Lys Ser Leu Ser Leu Ser Pro Gly Lys
        355                 360


<210> SEQ ID NO 61
<211> LENGTH: 369
<212> TYPE: PRT
<213> ORGANISM: Artificial Sequence
<220> FEATURE:
<223> OTHER INFORMATION: Fusion protein SS302-016

<400> SEQUENCE: 61

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Gly Ala Ala Val Ala Pro Pro Pro Ala
                85                  90                  95

Leu Pro Ala Pro Val Arg Leu Pro Gly Pro Ala Val Ala Pro Pro Pro
            100                 105                 110

Ala Leu Pro Ala Pro Val Arg Leu Pro Gly Pro Ala Val Ala Pro Pro
        115                 120                 125

Pro Ala Leu Pro Ala Pro Val Arg Leu Pro Gly Pro Ala Glu Ser Lys
    130                 135                 140
```

Tyr Gly Pro Pro Cys Pro Pro Cys Pro Ala Pro Glu Ala Ala Gly Gly
145 150 155 160

Pro Ser Val Phe Leu Phe Pro Pro Lys Pro Lys Asp Thr Leu Met Ile
165 170 175

Ser Arg Thr Pro Glu Val Thr Cys Val Val Val Asp Val Ser Gln Glu
180 185 190

Asp Pro Glu Val Gln Phe Asn Trp Tyr Val Asp Gly Val Glu Val His
195 200 205

Asn Ala Lys Thr Lys Pro Arg Glu Glu Gln Phe Asn Ser Thr Tyr Arg
210 215 220

Val Val Ser Val Leu Thr Val Leu His Gln Asp Trp Leu Asn Gly Lys
225 230 235 240

Glu Tyr Lys Cys Lys Val Ser Asn Lys Gly Leu Pro Ser Ser Ile Glu
245 250 255

Lys Thr Ile Ser Lys Ala Lys Gly Gln Pro Arg Glu Pro Gln Val Tyr
260 265 270

Thr Leu Pro Pro Ser Gln Glu Glu Met Thr Lys Asn Gln Val Ser Leu
275 280 285

Thr Cys Leu Val Lys Gly Phe Tyr Pro Ser Asp Ile Ala Val Glu Trp
290 295 300

Glu Ser Asn Gly Gln Pro Glu Asn Asn Tyr Lys Thr Thr Pro Pro Val
305 310 315 320

Leu Asp Ser Asp Gly Ser Phe Phe Leu Tyr Ser Arg Leu Thr Val Asp
325 330 335

Lys Ser Arg Trp Gln Glu Gly Asn Val Phe Ser Cys Ser Val Met His
340 345 350

Glu Ala Leu His Asn His Tyr Thr Gln Lys Ser Leu Ser Leu Ser Leu
355 360 365

Gly

<210> SEQ ID NO 62
<211> LENGTH: 369
<212> TYPE: PRT
<213> ORGANISM: Artificial Sequence
<220> FEATURE:
<223> OTHER INFORMATION: Fusion protein SS302-017

<400> SEQUENCE: 62

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr Arg Arg
20 25 30

Glu Ala Glu Asp Leu Gln Val Gly Gln Val Glu Leu Gly Gly Gly Pro
35 40 45

Gly Ala Gly Ser Leu Gln Pro Leu Ala Leu Glu Gly Ser Leu Gln Lys
50 55 60

Arg Gly Ile Val Glu Gln Cys Cys Thr Ser Ile Cys Ser Leu Tyr Gln
65 70 75 80

Leu Glu Asn Tyr Cys Asn Gly Gly Ala Ala Val Ala Pro Pro Pro Ala
85 90 95

Leu Pro Ala Pro Val Arg Leu Pro Gly Pro Ala Val Ala Pro Pro Pro
100 105 110

Ala Leu Pro Ala Pro Val Arg Leu Pro Gly Pro Ala Val Ala Pro Pro
115 120 125

```
Pro Ala Leu Pro Ala Pro Val Arg Leu Pro Gly Pro Ala Glu Ser Lys
    130                 135                 140

Tyr Gly Pro Pro Cys Pro Pro Cys Pro Ala Pro Glu Phe Leu Gly Gly
145                 150                 155                 160

Pro Ser Val Phe Leu Phe Pro Pro Lys Pro Lys Asp Thr Leu Tyr Ile
                165                 170                 175

Thr Arg Glu Pro Glu Val Thr Cys Val Val Val Asp Val Ser Gln Glu
            180                 185                 190

Asp Pro Glu Val Gln Phe Asn Trp Tyr Val Asp Gly Val Glu Val His
        195                 200                 205

Asn Ala Lys Thr Lys Pro Arg Glu Glu Gln Phe Ala Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Gly Leu Pro Ser Ser Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Gln Glu Glu Met Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Arg Leu Thr Val Asp
                325                 330                 335

Lys Ser Arg Trp Gln Glu Gly Asn Val Phe Ser Cys Ser Val Met His
            340                 345                 350

Glu Ala Leu His Asn His Tyr Thr Gln Lys Ser Leu Ser Leu Ser Leu
        355                 360                 365

Gly


<210> SEQ ID NO 63
<211> LENGTH: 369
<212> TYPE: PRT
<213> ORGANISM: Artificial Sequence
<220> FEATURE:
<223> OTHER INFORMATION: Fusion protein SS302-018

<400> SEQUENCE: 63

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Gly Ala Ala Val Ala Pro Pro Pro Ala
                85                  90                  95

Leu Pro Ala Pro Val Arg Leu Pro Gly Pro Ala Val Ala Pro Pro Pro
            100                 105                 110

Ala Leu Pro Ala Pro Val Arg Leu Pro Gly Pro Ala Val Ala Pro Pro
```

```
        115                 120                 125

Pro Ala Leu Pro Ala Pro Val Arg Leu Pro Gly Pro Ala Glu Ser Lys
    130                 135                 140

Tyr Gly Pro Pro Cys Pro Pro Cys Pro Ala Pro Glu Phe Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser Gln Glu
            180                 185                 190

Asp Pro Glu Val Gln Phe Asn Trp Tyr Val Asp Gly Val Glu Val His
        195                 200                 205

Asn Ala Lys Thr Lys Pro Arg Glu Glu Gln Phe Ala Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Gly Leu Pro Ser Ser Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Gln Glu Glu Met Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Arg Leu Thr Val Asp
                325                 330                 335

Lys Ser Arg Trp Gln Glu Gly Asn Val Phe Ser Cys Ser Val Leu His
            340                 345                 350

Glu Ala Leu His Ser His Tyr Thr Gln Lys Ser Leu Ser Leu Ser Leu
        355                 360                 365

Gly


<210> SEQ ID NO 64
<211> LENGTH: 369
<212> TYPE: PRT
<213> ORGANISM: Artificial Sequence
<220> FEATURE:
<223> OTHER INFORMATION: Fusion protein SS302-019

<400> SEQUENCE: 64

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Glu Gln
65                  70                  75                  80

Leu Glu Asn Tyr Cys Asn Gly Gly Ala Ala Val Ala Pro Pro Pro Ala
                85                  90                  95

Leu Pro Ala Pro Val Arg Leu Pro Gly Pro Ala Val Ala Pro Pro Pro
            100                 105                 110
```

Ala Leu Pro Ala Pro Val Arg Leu Pro Gly Pro Ala Val Ala Pro Pro
115 120 125

Pro Ala Leu Pro Ala Pro Val Arg Leu Pro Gly Pro Ala Glu Ser Lys
130 135 140

Tyr Gly Pro Pro Cys Pro Pro Cys Pro Ala Pro Glu Ala Ala Gly Gly
145 150 155 160

Pro Ser Val Phe Leu Phe Pro Pro Lys Pro Lys Asp Thr Leu Met Ile
165 170 175

Ser Arg Thr Pro Glu Val Thr Cys Val Val Val Asp Val Ser Gln Glu
180 185 190

Asp Pro Glu Val Gln Phe Asn Trp Tyr Val Asp Gly Val Glu Val His
195 200 205

Asn Ala Lys Thr Lys Pro Arg Glu Glu Gln Phe Asn Ser Thr Tyr Arg
210 215 220

Val Val Ser Val Leu Thr Val Leu His Gln Asp Trp Leu Asn Gly Lys
225 230 235 240

Glu Tyr Lys Cys Lys Val Ser Asn Lys Gly Leu Pro Ser Ser Ile Glu
245 250 255

Lys Thr Ile Ser Lys Ala Lys Gly Gln Pro Arg Glu Pro Gln Val Tyr
260 265 270

Thr Leu Pro Pro Ser Gln Glu Glu Met Thr Lys Asn Gln Val Ser Leu
275 280 285

Thr Cys Leu Val Lys Gly Phe Tyr Pro Ser Asp Ile Ala Val Glu Trp
290 295 300

Glu Ser Asn Gly Gln Pro Glu Asn Asn Tyr Lys Thr Thr Pro Pro Val
305 310 315 320

Leu Asp Ser Asp Gly Ser Phe Phe Leu Tyr Ser Arg Leu Thr Val Asp
325 330 335

Lys Ser Arg Trp Gln Glu Gly Asn Val Phe Ser Cys Ser Val Met His
340 345 350

Glu Ala Leu His Asn His Tyr Thr Gln Lys Ser Leu Ser Leu Ser Leu
355 360 365

Gly

<210> SEQ ID NO 65
<211> LENGTH: 353
<212> TYPE: PRT
<213> ORGANISM: Artificial Sequence
<220> FEATURE:
<223> OTHER INFORMATION: Fusion protein SS302-022

<400> SEQUENCE: 65

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr Lys Arg
20 25 30

Ile Lys Arg Glu Ala Glu Asp Leu Gln Val Gly Gln Val Glu Leu Gly
35 40 45

Gly Gly Pro Gly Ala Gly Ser Leu Gln Pro Leu Ala Leu Glu Gly Ser
50 55 60

Leu Gln Lys Arg Ile Lys Arg Gly Ile Val Glu Gln Cys Cys Thr Ser
65 70 75 80

Ile Cys Ser Leu Tyr Gln Leu Glu Asn Tyr Cys Asn Gly Gly Gly Ser
85 90 95

```
Val Ala Pro Pro Pro Ala Leu Pro Ala Pro Val Arg Leu Pro Gly Pro
            100                 105                 110

Ala Val Ala Pro Pro Pro Ala Leu Pro Ala Pro Val Arg Leu Pro Gly
        115                 120                 125

Pro Ala Val Glu Cys Pro Pro Cys Pro Ala Pro Pro Val Ala Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Phe Arg Val
        195                 200                 205

Val Ser Val Leu Thr Val Val His Gln Asp Trp Leu Asn Gly Lys Glu
    210                 215                 220

Tyr Lys Cys Lys Val Ser Asn Lys Gly Leu Pro Ala Pro Ile Glu Lys
225                 230                 235                 240

Thr Ile Ser Lys Thr Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Met Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys


<210> SEQ ID NO 66
<211> LENGTH: 355
<212> TYPE: PRT
<213> ORGANISM: Artificial Sequence
<220> FEATURE:
<223> OTHER INFORMATION: Fusion protein SS302-023

<400> SEQUENCE: 66

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Asp Asp
            20                  25                  30

Asp Asp Lys Glu Ala Glu Asp Leu Gln Val Gly Gln Val Glu Leu Gly
        35                  40                  45

Gly Gly Pro Gly Ala Gly Ser Leu Gln Pro Leu Ala Leu Glu Gly Ser
    50                  55                  60

Leu Gln Lys Arg Asp Asp Asp Asp Lys Gly Ile Val Glu Gln Cys Cys
65                  70                  75                  80

Thr Ser Ile Cys Ser Leu Tyr Gln Leu Glu Asn Tyr Cys Asn Gly Gly
                85                  90                  95

Gly Ser Val Ala Pro Pro Pro Ala Leu Pro Ala Pro Val Arg Leu Pro
```

```
            100                 105                 110

Gly Pro Ala Val Ala Pro Pro Pro Ala Leu Pro Ala Pro Val Arg Leu
        115                 120                 125

Pro Gly Pro Ala Val Glu Cys Pro Pro Cys Pro Ala Pro Pro Val Ala
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Gln Phe Asn Trp Tyr Val Asp Gly Val Glu Val
            180                 185                 190

His Asn Ala Lys Thr Lys Pro Arg Glu Glu Gln Phe Asn Ser Thr Phe
        195                 200                 205

Arg Val Val Ser Val Leu Thr Val Val His Gln Asp Trp Leu Asn Gly
    210                 215                 220

Lys Glu Tyr Lys Cys Lys Val Ser Asn Lys Gly Leu Pro Ala Pro Ile
225                 230                 235                 240

Glu Lys Thr Ile Ser Lys Thr Lys Gly Gln Pro Arg Glu Pro Gln Val
                245                 250                 255

Tyr Thr Leu Pro Pro Ser Arg Glu Glu Met Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Met Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
            340                 345                 350

Pro Gly Lys
        355


<210> SEQ ID NO 67
<211> LENGTH: 369
<212> TYPE: PRT
<213> ORGANISM: Artificial Sequence
<220> FEATURE:
<223> OTHER INFORMATION: Fusion protein SS302-029

<400> SEQUENCE: 67

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Glu Gln
65                  70                  75                  80

Leu Glu Asn Tyr Cys Asn Gly Gly Ala Ala Val Ala Pro Pro Pro Ala
                85                  90                  95

Leu Pro Ala Pro Val Arg Leu Pro Gly Pro Ala Val Ala Pro Pro Pro
```

```
            100                 105                 110

Ala Leu Pro Ala Pro Val Arg Leu Pro Gly Pro Ala Val Ala Pro Pro
        115                 120                 125

Pro Ala Leu Pro Ala Pro Val Arg Leu Pro Gly Pro Ala Glu Ser Lys
    130                 135                 140

Tyr Gly Pro Pro Cys Pro Pro Cys Pro Ala Pro Glu Phe Leu Gly Gly
145                 150                 155                 160

Pro Ser Val Phe Leu Phe Pro Pro Lys Pro Lys Asp Thr Leu Tyr Ile
                165                 170                 175

Thr Arg Glu Pro Glu Val Thr Cys Val Val Val Asp Val Ser Gln Glu
            180                 185                 190

Asp Pro Glu Val Gln Phe Asn Trp Tyr Val Asp Gly Val Glu Val His
        195                 200                 205

Asn Ala Lys Thr Lys Pro Arg Glu Glu Gln Phe Ala Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Gly Leu Pro Ser Ser Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Gln Glu Glu Met Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Arg Leu Thr Val Asp
                325                 330                 335

Lys Ser Arg Trp Gln Glu Gly Asn Val Phe Ser Cys Ser Val Met His
            340                 345                 350

Glu Ala Leu His Asn His Tyr Thr Gln Lys Ser Leu Ser Leu Ser Leu
        355                 360                 365

Gly


<210> SEQ ID NO 68
<211> LENGTH: 369
<212> TYPE: PRT
<213> ORGANISM: Artificial Sequence
<220> FEATURE:
<223> OTHER INFORMATION: Fusion protein SS302-030

<400> SEQUENCE: 68

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Glu Gln
65                  70                  75                  80

Leu Glu Asn Tyr Cys Asn Gly Gly Ala Ala Val Ala Pro Pro Pro Ala
                85                  90                  95
```

```
Leu Pro Ala Pro Val Arg Leu Pro Gly Pro Ala Val Ala Pro Pro Pro
            100                 105                 110

Ala Leu Pro Ala Pro Val Arg Leu Pro Gly Pro Ala Val Ala Pro Pro
        115                 120                 125

Pro Ala Leu Pro Ala Pro Val Arg Leu Pro Gly Pro Ala Glu Ser Lys
    130                 135                 140

Tyr Gly Pro Pro Cys Pro Pro Cys Pro Ala Pro Glu Phe Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser Gln Glu
            180                 185                 190

Asp Pro Glu Val Gln Phe Asn Trp Tyr Val Asp Gly Val Glu Val His
        195                 200                 205

Asn Ala Lys Thr Lys Pro Arg Glu Glu Gln Phe Ala Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Gly Leu Pro Ser Ser Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Gln Glu Glu Met Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Arg Leu Thr Val Asp
                325                 330                 335

Lys Ser Arg Trp Gln Glu Gly Asn Val Phe Ser Cys Ser Val Leu His
            340                 345                 350

Glu Ala Leu His Ser His Tyr Thr Gln Lys Ser Leu Ser Leu Ser Leu
        355                 360                 365

Gly


<210> SEQ ID NO 69
<211> LENGTH: 350
<212> TYPE: PRT
<213> ORGANISM: Artificial Sequence
<220> FEATURE:
<223> OTHER INFORMATION: Fusion protein SS302-035

<400> SEQUENCE: 69

Phe Val Asn Gln His Leu Cys Gly Ser His Leu Val Glu Ala Leu His
1               5                   10                  15

Leu Val Cys Gly Glu Arg Gly Phe His Tyr Thr Pro Lys Arg Glu Ala
            20                  25                  30

Glu Asp Leu Gln Val Gly Gln Val Glu Leu Gly Gly Gly Pro Gly Ala
        35                  40                  45

Gly Ser Leu Gln Pro Leu Ala Leu Glu Gly Ser Leu Gln Lys Arg Gly
    50                  55                  60

Ile Val Glu Gln Cys Cys Thr Ser Ile Cys Ser Leu Glu Gln Leu Glu
65                  70                  75                  80
```

```
Asn Tyr Cys Asn Gly Gly Ala Ala Val Ala Pro Pro Pro Ala Leu Pro
                85                  90                  95

Ala Pro Val Arg Leu Pro Gly Pro Ala Val Ala Pro Pro Pro Ala Leu
            100                 105                 110

Pro Ala Pro Val Arg Leu Pro Gly Pro Ala Glu Ser Lys Tyr Gly Pro
        115                 120                 125

Pro Cys Pro Pro Cys Pro Ala Pro Glu Ala Ala Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly
            340                 345                 350


<210> SEQ ID NO 70
<211> LENGTH: 349
<212> TYPE: PRT
<213> ORGANISM: Artificial Sequence
<220> FEATURE:
<223> OTHER INFORMATION: Fusion protein SS302-036

<400> SEQUENCE: 70

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys Arg Glu Ala
            20                  25                  30

Glu Asp Leu Gln Val Gly Gln Val Glu Leu Gly Gly Gly Pro Gly Ala
        35                  40                  45

Gly Ser Leu Gln Pro Leu Ala Leu Glu Gly Ser Leu Lys Arg Gly Ile
    50                  55                  60

Val Glu Gln Cys Cys Thr Ser Ile Cys Ser Leu Glu Gln Leu Glu Asn
65                  70                  75                  80

Tyr Cys Asn Gly Gly Ala Ala Val Ala Pro Pro Pro Ala Leu Pro Ala
                85                  90                  95
```

```
Pro Val Arg Leu Pro Gly Pro Ala Val Ala Pro Pro Pro Ala Leu Pro
            100                 105                 110

Ala Pro Val Arg Leu Pro Gly Pro Ala Glu Ser Lys Tyr Gly Pro Pro
        115                 120                 125

Cys Pro Pro Cys Pro Ala Pro Glu Ala Ala Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
                165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Gln Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Arg Leu Thr Val Asp Lys Ser Arg Trp
305                 310                 315                 320

Gln Glu Gly Asn Val Phe Ser Cys Ser Val Met His Glu Ala Leu His
                325                 330                 335

Asn His Tyr Thr Gln Lys Ser Leu Ser Leu Ser Leu Gly
            340                 345


<210> SEQ ID NO 71
<211> LENGTH: 350
<212> TYPE: PRT
<213> ORGANISM: Artificial Sequence
<220> FEATURE:
<223> OTHER INFORMATION: Fusion protein SS302-037

<400> SEQUENCE: 71

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Arg Glu Ala
            20                  25                  30

Glu Asp Leu Gln Val Gly Gln Val Glu Leu Gly Gly Gly Pro Gly Ala
        35                  40                  45

Gly Ser Leu Gln Pro Leu Ala Leu Glu Gly Ser Leu Gln Lys Arg Gly
    50                  55                  60

Ile Val Glu Gln Cys Cys Thr Ser Ile Cys Ser Leu Glu Gln Leu Glu
65                  70                  75                  80

Asn Tyr Cys Asn Gly Gly Ala Ala Val Ala Pro Pro Pro Ala Leu Pro
                85                  90                  95

Ala Pro Val Arg Leu Pro Gly Pro Ala Val Ala Pro Pro Pro Ala Leu
            100                 105                 110
```

```
Pro Ala Pro Val Arg Leu Pro Gly Pro Ala Glu Ser Lys Tyr Gly Pro
        115                 120                 125

Pro Cys Pro Pro Cys Pro Ala Pro Glu Ala Ala Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly
            340                 345                 350


<210> SEQ ID NO 72
<211> LENGTH: 352
<212> TYPE: PRT
<213> ORGANISM: Artificial Sequence
<220> FEATURE:
<223> OTHER INFORMATION: Fusion protein SS302-038

<400> SEQUENCE: 72

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Gly Gly Ala Ala Val Ala Pro Pro Pro Ala
                85                  90                  95

Leu Pro Ala Pro Val Arg Leu Pro Gly Pro Ala Val Ala Pro Pro Pro
            100                 105                 110

Ala Leu Pro Ala Pro Val Arg Leu Pro Gly Pro Ala Glu Ser Lys Tyr
        115                 120                 125
```

```
Gly Pro Pro Cys Pro Pro Cys Pro Ala Pro Glu Ala Ala Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350


<210> SEQ ID NO 73
<211> LENGTH: 32
<212> TYPE: PRT
<213> ORGANISM: Artificial Sequence
<220> FEATURE:
<223> OTHER INFORMATION: SS302-001M B chain

<400> SEQUENCE: 73

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 74
<211> LENGTH: 307
<212> TYPE: PRT
<213> ORGANISM: Artificial Sequence
<220> FEATURE:
<223> OTHER INFORMATION: SS302-001M A chain-L-Fc1

<400> SEQUENCE: 74

Gly Ile Val Glu Gln Cys Cys Thr Ser Ile Cys Ser Leu Tyr Gln Leu
1               5                   10                  15

Glu Asn Tyr Cys Asn Gly Ser Gly Gly Gly Gly Ser Gly Gly Gly Gly
            20                  25                  30

Ser Gly Gly Gly Gly Ser Gly Gly Gly Gly Ser Gly Gly Gly Gly Ser
        35                  40                  45

Ser Ser Ser Ser Lys Ala Pro Pro Pro Ser Leu Pro Ser Pro Ser Arg
    50                  55                  60
```

```
Leu Pro Gly Pro Ser Asp Thr Pro Ile Leu Pro Gln Glu Pro Lys Ser
65                  70                  75                  80

Cys Asp Lys Thr His Thr Cys Pro Pro Cys Pro Ala Pro Glu Leu Leu
                85                  90                  95

Gly Gly Pro Ser Val Phe Leu Phe Pro Pro Lys Pro Lys Asp Thr Leu
            100                 105                 110

Met Ile Ser Arg Thr Pro Glu Val Thr Cys Val Val Val Asp Val Ser
        115                 120                 125

His Glu Asp Pro Glu Val Lys Phe Asn Trp Tyr Val Asp Gly Val Glu
    130                 135                 140

Val His Asn Ala Lys Thr Lys Pro Arg Glu Glu Gln Tyr Asn Ser Thr
145                 150                 155                 160

Tyr Arg Val Val Ser Val Leu Thr Val Leu His Gln Asp Trp Leu Asn
                165                 170                 175

Gly Lys Glu Tyr Lys Cys Lys Val Ser Asn Lys Ala Leu Pro Ala Pro
            180                 185                 190

Ile Glu Lys Thr Ile Ser Lys Ala Lys Gly Gln Pro Arg Glu Pro Gln
        195                 200                 205

Val Tyr Thr Leu Pro Pro Ser Arg Asp Glu Leu Thr Lys Asn Gln Val
    210                 215                 220

Ser Leu Thr Cys Leu Val Lys Gly Phe Tyr Pro Ser Asp Ile Ala Val
225                 230                 235                 240

Glu Trp Glu Ser Asn Gly Gln Pro Glu Asn Asn Tyr Lys Thr Thr Pro
                245                 250                 255

Pro Val Leu Asp Ser Asp Gly Ser Phe Phe Leu Tyr Ser Lys Leu Thr
            260                 265                 270

Val Asp Lys Ser Arg Trp Gln Gln Gly Asn Val Phe Ser Cys Ser Val
        275                 280                 285

Met His Glu Ala Leu His Asn His Tyr Thr Gln Lys Ser Leu Ser Leu
    290                 295                 300

Ser Pro Gly
305


<210> SEQ ID NO 75
<211> LENGTH: 32
<212> TYPE: PRT
<213> ORGANISM: Artificial Sequence
<220> FEATURE:
<223> OTHER INFORMATION: SS302-002M B chain

<400> SEQUENCE: 75

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 76
<211> LENGTH: 299
<212> TYPE: PRT
<213> ORGANISM: Artificial Sequence
<220> FEATURE:
<223> OTHER INFORMATION: SS302-002M A chain-L-Fc2

<400> SEQUENCE: 76

Gly Ile Val Glu Gln Cys Cys Thr Ser Ile Cys Ser Leu Tyr Gln Leu
1               5                   10                  15

Glu Asn Tyr Cys Asn Gly Ser Gly Gly Gly Gly Ser Gly Gly Gly Gly
```

```
            20                  25                  30

Ser Gly Gly Gly Gly Ser Gly Gly Gly Gly Ser Gly Gly Gly Gly Ser
        35                  40                  45

Ser Ser Ser Ser Lys Ala Pro Pro Pro Ser Leu Pro Ser Pro Ser Arg
    50                  55                  60

Leu Pro Gly Pro Ser Asp Thr Pro Ile Leu Pro Gln Val Glu Cys Pro
65                  70                  75                  80

Pro Cys Pro Ala Pro Pro Val Ala Gly Pro Ser Val Phe Leu Phe Pro
                85                  90                  95

Pro Lys Pro Lys Asp Gln Leu Met Ile Ser Arg Thr Pro Glu Val Thr
            100                 105                 110

Cys Val Val Val Asp Val Ser His Glu Asp Pro Glu Val Gln Phe Asn
        115                 120                 125

Trp Tyr Val Asp Gly Val Glu Val His Asn Ala Lys Thr Lys Pro Arg
    130                 135                 140

Glu Glu Gln Phe Asn Ser Thr Phe Arg Val Val Ser Val Leu Thr Val
145                 150                 155                 160

Val His Gln Asp Trp Leu Asn Gly Lys Glu Tyr Lys Cys Lys Val Ser
                165                 170                 175

Asn Lys Gly Leu Pro Ala Ser Ile Glu Lys Thr Ile Ser Lys Thr Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Met Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Leu His Glu Ala Leu His Asn His Tyr
        275                 280                 285

Thr Gln Lys Ser Leu Ser Leu Ser Pro Gly Lys
    290                 295


<210> SEQ ID NO 77
<211> LENGTH: 32
<212> TYPE: PRT
<213> ORGANISM: Artificial Sequence
<220> FEATURE:
<223> OTHER INFORMATION: SS302-003M B chain

<400> SEQUENCE: 77

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 78
<211> LENGTH: 304
<212> TYPE: PRT
<213> ORGANISM: Artificial Sequence
<220> FEATURE:
<223> OTHER INFORMATION: SS302-003M A chain-L-Fc3

<400> SEQUENCE: 78
```

```
Gly Ile Val Glu Gln Cys Cys Thr Ser Ile Cys Ser Leu Tyr Gln Leu
1               5                   10                  15

Glu Asn Tyr Cys Asn Gly Ser Gly Gly Gly Gly Ser Gly Gly Gly Gly
            20                  25                  30

Ser Gly Gly Gly Gly Ser Gly Gly Gly Gly Ser Gly Gly Gly Gly Ser
        35                  40                  45

Ser Ser Ser Ser Lys Ala Pro Pro Pro Ser Leu Pro Ser Pro Ser Arg
    50                  55                  60

Leu Pro Gly Pro Ser Asp Thr Pro Ile Leu Pro Gln Glu Ser Lys Tyr
65                  70                  75                  80

Gly Pro Pro Cys Pro Pro Cys Pro Ala Pro Glu Phe Leu Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser Gln Glu Asp
        115                 120                 125

Pro Glu Val Gln Phe Asn Trp Tyr Val Asp Gly Val Glu Val His Asn
    130                 135                 140

Ala Lys Thr Lys Pro Arg Glu Glu Gln Phe Asn Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Gly Leu Pro Ser Ser Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Gln Glu Glu Met Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Arg Leu Thr Val Asp Lys
            260                 265                 270

Ser Arg Trp Gln Glu Gly Asn Val Phe Ser Cys Ser Val Met His Glu
        275                 280                 285

Ala Leu His Asn His Tyr Thr Gln Lys Ser Leu Ser Leu Ser Leu Gly
    290                 295                 300


<210> SEQ ID NO 79
<211> LENGTH: 32
<212> TYPE: PRT
<213> ORGANISM: Artificial Sequence
<220> FEATURE:
<223> OTHER INFORMATION: SS302-004M B chain

<400> SEQUENCE: 79

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 80
<211> LENGTH: 271
<212> TYPE: PRT
<213> ORGANISM: Artificial Sequence
<220> FEATURE:
```

<223> OTHER INFORMATION: SS302-004M A chain-L-Fc2

<400> SEQUENCE: 80

Gly Ile Val Glu Gln Cys Cys Thr Ser Ile Cys Ser Leu Tyr Gln Leu
1 5 10 15

Glu Asn Tyr Cys Asn Gly Ser Gly Gly Gly Ser Gly Gly Gly Gly
20 25 30

Ser Gly Gly Gly Gly Ser Gly Gly Gly Gly Ser Gly Gly Gly Gly Ser
35 40 45

Val Glu Cys Pro Pro Cys Pro Ala Pro Pro Val Ala Gly Pro Ser Val
50 55 60

Phe Leu Phe Pro Pro Lys Pro Lys Asp Gln Leu Met Ile Ser Arg Thr
65 70 75 80

Pro Glu Val Thr Cys Val Val Val Asp Val Ser His Glu Asp Pro Glu
85 90 95

Val Gln Phe Asn Trp Tyr Val Asp Gly Val Glu Val His Asn Ala Lys
100 105 110

Thr Lys Pro Arg Glu Glu Gln Phe Asn Ser Thr Phe Arg Val Val Ser
115 120 125

Val Leu Thr Val Val His Gln Asp Trp Leu Asn Gly Lys Glu Tyr Lys
130 135 140

Cys Lys Val Ser Asn Lys Gly Leu Pro Ala Ser Ile Glu Lys Thr Ile
145 150 155 160

Ser Lys Thr Lys Gly Gln Pro Arg Glu Pro Gln Val Tyr Thr Leu Pro
165 170 175

Pro Ser Arg Glu Glu Met Thr Lys Asn Gln Val Ser Leu Thr Cys Leu
180 185 190

Val Lys Gly Phe Tyr Pro Ser Asp Ile Ala Val Glu Trp Glu Ser Asn
195 200 205

Gly Gln Pro Glu Asn Asn Tyr Lys Thr Thr Pro Pro Met Leu Asp Ser
210 215 220

Asp Gly Ser Phe Phe Leu Tyr Ser Lys Leu Thr Val Asp Lys Ser Arg
225 230 235 240

Trp Gln Gln Gly Asn Val Phe Ser Cys Ser Val Leu His Glu Ala Leu
245 250 255

His Asn His Tyr Thr Gln Lys Ser Leu Ser Leu Ser Pro Gly Lys
260 265 270

<210> SEQ ID NO 81
<211> LENGTH: 32
<212> TYPE: PRT
<213> ORGANISM: Artificial Sequence
<220> FEATURE:
<223> OTHER INFORMATION: SS302-005M B chain

<400> SEQUENCE: 81

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr Arg Arg
20 25 30

<210> SEQ ID NO 82
<211> LENGTH: 269
<212> TYPE: PRT
<213> ORGANISM: Artificial Sequence
<220> FEATURE:
<223> OTHER INFORMATION: SS302-005M A chain-L-Fc4

<400> SEQUENCE: 82

```
Gly Ile Val Glu Gln Cys Cys Thr Ser Ile Cys Ser Leu Tyr Gln Leu
1               5                   10                  15

Glu Asn Tyr Cys Asn Gly Gly Gly Gly Ser Gly Gly Gly Gly Ser Gly
            20                  25                  30

Gly Gly Gly Ser Gly Gly Gly Gly Ser Gly Gly Gly Gly Ser Val Glu
        35                  40                  45

Cys Pro Pro Cys Pro Ala Pro Pro Val Ala Gly Pro Ser Val Phe Leu
    50                  55                  60

Phe Pro Pro Lys Pro Lys Asp Gln Leu Met Ile Ser Arg Thr Pro Glu
65                  70                  75                  80

Val Thr Cys Val Val Val Asp Val Ser His Glu Asp Pro Glu Val Gln
                85                  90                  95

Phe Asn Trp Tyr Val Asp Gly Val Glu Val His Asn Ala Lys Thr Lys
            100                 105                 110

Pro Arg Glu Glu Gln Phe Ala Ser Thr Phe Arg Val Val Ser Val Leu
        115                 120                 125

Thr Val Val His Gln Asp Trp Leu Asn Gly Lys Glu Tyr Lys Cys Lys
    130                 135                 140

Val Ser Asn Lys Gly Leu Pro Ala Ser Ile Glu Lys Thr Ile Ser Lys
145                 150                 155                 160

Thr Lys Gly Gln Pro Arg Glu Pro Gln Val Tyr Thr Leu Pro Pro Ser
                165                 170                 175

Arg Glu Glu Met Thr Lys Asn Gln Val Ser Leu Thr Cys Leu Val Lys
            180                 185                 190

Gly Phe Tyr Pro Ser Asp Ile Ala Val Glu Trp Glu Ser Asn Gly Gln
        195                 200                 205

Pro Glu Asn Asn Tyr Lys Thr Thr Pro Pro Met Leu Asp Ser Asp Gly
    210                 215                 220

Ser Phe Phe Leu Tyr Ser Lys Leu Thr Val Asp Lys Ser Arg Trp Gln
225                 230                 235                 240

Gln Gly Asn Val Phe Ser Cys Ser Val Leu His Glu Ala Leu His Asn
                245                 250                 255

His Tyr Thr Gln Lys Ser Leu Ser Leu Ser Pro Gly Lys
            260                 265
```

<210> SEQ ID NO 83
<211> LENGTH: 32
<212> TYPE: PRT
<213> ORGANISM: Artificial Sequence
<220> FEATURE:
<223> OTHER INFORMATION: SS302-006M B chain

<400> SEQUENCE: 83

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```

<210> SEQ ID NO 84
<211> LENGTH: 272
<212> TYPE: PRT
<213> ORGANISM: Artificial Sequence
<220> FEATURE:
<223> OTHER INFORMATION: SS302-006M A chain-L-Fc16

<400> SEQUENCE: 84

```
Gly Ile Val Glu Gln Cys Cys Thr Ser Ile Cys Ser Leu Tyr Gln Leu
1               5                   10                  15

Glu Asn Tyr Cys Asn Ser Ala Ser Ser Lys Ala Pro Pro Pro Ser Leu
            20                  25                  30

Pro Ser Pro Ser Arg Leu Pro Gly Pro Ser Asp Thr Pro Ile Leu Pro
        35                  40                  45

Gln Val Glu Cys Pro Pro Cys Pro Ala Pro Pro Val Ala Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Gln Phe Asn Trp Tyr Val Asp Gly Val Glu Val His Asn Ala
            100                 105                 110

Lys Thr Lys Pro Arg Glu Glu Gln Phe Asn Ser Thr Phe Arg Val Val
        115                 120                 125

Ser Val Leu Thr Val Val His Gln Asp Trp Leu Asn Gly Lys Glu Tyr
    130                 135                 140

Lys Cys Lys Val Ser Asn Lys Gly Leu Pro Ala Pro Ile Glu Lys Thr
145                 150                 155                 160

Ile Ser Lys Thr Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Met Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270
```

<210> SEQ ID NO 85
<211> LENGTH: 32
<212> TYPE: PRT
<213> ORGANISM: Artificial Sequence
<220> FEATURE:
<223> OTHER INFORMATION: SS302-007M B chain

<400> SEQUENCE: 85

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```

<210> SEQ ID NO 86
<211> LENGTH: 272
<212> TYPE: PRT
<213> ORGANISM: Artificial Sequence
<220> FEATURE:
<223> OTHER INFORMATION: SS302-007M A chain-L-Fc16

<400> SEQUENCE: 86

```
Gly Ile Val Glu Gln Cys Cys Thr Ser Ile Cys Ser Leu Tyr Gln Leu
1               5                   10                  15
```

```
Glu Asn Tyr Cys Asn Ser Ser Ser Ser Lys Ala Pro Pro Pro Ser Leu
            20                  25                  30

Pro Ser Pro Ser Arg Leu Pro Gly Pro Ser Asp Thr Pro Ile Leu Pro
        35                  40                  45

Gln Val Glu Cys Pro Pro Cys Pro Ala Pro Pro Val Ala Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Gln Phe Asn Trp Tyr Val Asp Gly Val Glu Val His Asn Ala
            100                 105                 110

Lys Thr Lys Pro Arg Glu Glu Gln Phe Asn Ser Thr Phe Arg Val Val
        115                 120                 125

Ser Val Leu Thr Val Val His Gln Asp Trp Leu Asn Gly Lys Glu Tyr
    130                 135                 140

Lys Cys Lys Val Ser Asn Lys Gly Leu Pro Ala Pro Ile Glu Lys Thr
145                 150                 155                 160

Ile Ser Lys Thr Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Met Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270


<210> SEQ ID NO 87
<211> LENGTH: 32
<212> TYPE: PRT
<213> ORGANISM: Artificial Sequence
<220> FEATURE:
<223> OTHER INFORMATION: SS302-008M B chain

<400> SEQUENCE: 87

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 88
<211> LENGTH: 300
<212> TYPE: PRT
<213> ORGANISM: Artificial Sequence
<220> FEATURE:
<223> OTHER INFORMATION: SS302-008M A chain-L-Fc16

<400> SEQUENCE: 88

Gly Ile Val Glu Gln Cys Cys Thr Ser Ile Cys Ser Leu Tyr Gln Leu
1               5                   10                  15

Glu Asn Tyr Cys Asn Ser Ala Ser Ser Lys Ala Pro Pro Pro Ser Leu
```

```
            20                  25                  30

Pro Ser Pro Ser Arg Leu Pro Gly Pro Ser Asp Thr Pro Ile Leu Pro
        35                  40                  45

Gln Ser Ser Ser Ser Lys Ala Pro Pro Pro Ser Leu Pro Ser Pro Ser
    50                  55                  60

Arg Leu Pro Gly Pro Ser Asp Thr Pro Ile Leu Pro Gln Val Glu Cys
65                  70                  75                  80

Pro Pro Cys Pro Ala Pro Pro Val Ala Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Gln Phe
        115                 120                 125

Asn Trp Tyr Val Asp Gly Val Glu Val His Asn Ala Lys Thr Lys Pro
    130                 135                 140

Arg Glu Glu Gln Phe Asn Ser Thr Phe Arg Val Val Ser Val Leu Thr
145                 150                 155                 160

Val Val His Gln Asp Trp Leu Asn Gly Lys Glu Tyr Lys Cys Lys Val
                165                 170                 175

Ser Asn Lys Gly Leu Pro Ala Pro Ile Glu Lys Thr Ile Ser Lys Thr
            180                 185                 190

Lys Gly Gln Pro Arg Glu Pro Gln Val Tyr Thr Leu Pro Pro Ser Arg
        195                 200                 205

Glu Glu Met Thr Lys Asn Gln Val Ser Leu Thr Cys Leu Val Lys Gly
    210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Met Leu Asp Ser Asp Gly Ser
                245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
        275                 280                 285

Tyr Thr Gln Lys Ser Leu Ser Leu Ser Pro Gly Lys
    290                 295                 300


<210> SEQ ID NO 89
<211> LENGTH: 32
<212> TYPE: PRT
<213> ORGANISM: Artificial Sequence
<220> FEATURE:
<223> OTHER INFORMATION: SS302-009M B chain

<400> SEQUENCE: 89

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 90
<211> LENGTH: 293
<212> TYPE: PRT
<213> ORGANISM: Artificial Sequence
<220> FEATURE:
<223> OTHER INFORMATION: SS302-009M A chain-L-Fc16

<400> SEQUENCE: 90
```

```
Gly Ile Val Glu Gln Cys Cys Thr Ser Ile Cys Ser Leu Tyr Gln Leu
1               5                   10                  15

Glu Asn Tyr Cys Asn Gly Gly Gly Ser Val Ala Pro Pro Pro Ala Leu
            20                  25                  30

Pro Ala Pro Val Arg Leu Pro Gly Pro Ala Ser Ser Ser Ser Lys Ala
        35                  40                  45

Pro Pro Pro Ser Leu Pro Ser Pro Ser Arg Leu Pro Gly Pro Ser Asp
    50                  55                  60

Thr Pro Ile Leu Pro Gln Val Glu Cys Pro Pro Cys Pro Ala Pro Pro
65                  70                  75                  80

Val Ala Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
            100                 105                 110

Ser His Glu Asp Pro Glu Val Gln Phe Asn Trp Tyr Val Asp Gly Val
        115                 120                 125

Glu Val His Asn Ala Lys Thr Lys Pro Arg Glu Glu Gln Phe Asn Ser
    130                 135                 140

Thr Phe Arg Val Val Ser Val Leu Thr Val Val His Gln Asp Trp Leu
145                 150                 155                 160

Asn Gly Lys Glu Tyr Lys Cys Lys Val Ser Asn Lys Gly Leu Pro Ala
                165                 170                 175

Pro Ile Glu Lys Thr Ile Ser Lys Thr Lys Gly Gln Pro Arg Glu Pro
            180                 185                 190

Gln Val Tyr Thr Leu Pro Pro Ser Arg Glu Glu Met Thr Lys Asn Gln
        195                 200                 205

Val Ser Leu Thr Cys Leu Val Lys Gly Phe Tyr Pro Ser Asp Ile Ala
    210                 215                 220

Val Glu Trp Glu Ser Asn Gly Gln Pro Glu Asn Asn Tyr Lys Thr Thr
225                 230                 235                 240

Pro Pro Met Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly Lys
    290
```

<210> SEQ ID NO 91
<211> LENGTH: 32
<212> TYPE: PRT
<213> ORGANISM: Artificial Sequence
<220> FEATURE:
<223> OTHER INFORMATION: SS302-011M B chain

<400> SEQUENCE: 91

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```

<210> SEQ ID NO 92
<211> LENGTH: 294
<212> TYPE: PRT
<213> ORGANISM: Artificial Sequence
<220> FEATURE:

<223> OTHER INFORMATION: SS302-011M A chain-L-Fc16

<400> SEQUENCE: 92

Gly Ile Val Glu Gln Cys Cys Thr Ser Ile Cys Ser Leu Tyr Gln Leu
1 5 10 15

Glu Asn Tyr Cys Asn Gly Gly Gly Ser Val Ala Pro Pro Pro Ala Leu
20 25 30

Pro Ala Val Ala Pro Pro Pro Ala Leu Pro Ala Ser Ser Ser Ser Lys
35 40 45

Ala Pro Pro Pro Ser Leu Pro Ser Pro Ser Arg Leu Pro Gly Pro Ser
50 55 60

Asp Thr Pro Ile Leu Pro Gln Val Glu Cys Pro Pro Cys Pro Ala Pro
65 70 75 80

Pro Val Ala Gly Pro Ser Val Phe Leu Phe Pro Pro Lys Pro Lys Asp
85 90 95

Thr Leu Met Ile Ser Arg Thr Pro Glu Val Thr Cys Val Val Val Asp
100 105 110

Val Ser His Glu Asp Pro Glu Val Gln Phe Asn Trp Tyr Val Asp Gly
115 120 125

Val Glu Val His Asn Ala Lys Thr Lys Pro Arg Glu Glu Gln Phe Asn
130 135 140

Ser Thr Phe Arg Val Val Ser Val Leu Thr Val Val His Gln Asp Trp
145 150 155 160

Leu Asn Gly Lys Glu Tyr Lys Cys Lys Val Ser Asn Lys Gly Leu Pro
165 170 175

Ala Pro Ile Glu Lys Thr Ile Ser Lys Thr Lys Gly Gln Pro Arg Glu
180 185 190

Pro Gln Val Tyr Thr Leu Pro Pro Ser Arg Glu Glu Met Thr Lys Asn
195 200 205

Gln Val Ser Leu Thr Cys Leu Val Lys Gly Phe Tyr Pro Ser Asp Ile
210 215 220

Ala Val Glu Trp Glu Ser Asn Gly Gln Pro Glu Asn Asn Tyr Lys Thr
225 230 235 240

Thr Pro Pro Met Leu Asp Ser Asp Gly Ser Phe Phe Leu Tyr Ser Lys
245 250 255

Leu Thr Val Asp Lys Ser Arg Trp Gln Gln Gly Asn Val Phe Ser Cys
260 265 270

Ser Val Met His Glu Ala Leu His Asn His Tyr Thr Gln Lys Ser Leu
275 280 285

Ser Leu Ser Pro Gly Lys
290

<210> SEQ ID NO 93
<211> LENGTH: 32
<212> TYPE: PRT
<213> ORGANISM: Artificial Sequence
<220> FEATURE:
<223> OTHER INFORMATION: SS302-012M B chain

<400> SEQUENCE: 93

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr Arg Arg
20 25 30

<210> SEQ ID NO 94

<211> LENGTH: 282
<212> TYPE: PRT
<213> ORGANISM: Artificial Sequence
<220> FEATURE:
<223> OTHER INFORMATION: SS302-012M A chain-L-Fc1

<400> SEQUENCE: 94

```
Gly Ile Val Glu Gln Cys Cys Thr Ser Ile Cys Ser Leu Tyr Gln Leu
1               5                   10                  15

Glu Asn Tyr Cys Asn Gly Gly Gly Ser Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Val Glu Cys Pro Pro
    50                  55                  60

Cys Pro Ala Pro Pro Val Ala Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Gln Phe Asn Trp
            100                 105                 110

Tyr Val Asp Gly Val Glu Val His Asn Ala Lys Thr Lys Pro Arg Glu
        115                 120                 125

Glu Gln Phe Asn Ser Thr Phe Arg Val Val Ser Val Leu Thr Val Val
    130                 135                 140

His Gln Asp Trp Leu Asn Gly Lys Glu Tyr Lys Cys Lys Val Ser Asn
145                 150                 155                 160

Lys Gly Leu Pro Ala Pro Ile Glu Lys Thr Ile Ser Lys Thr Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Met Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280
```

<210> SEQ ID NO 95
<211> LENGTH: 32
<212> TYPE: PRT
<213> ORGANISM: Artificial Sequence
<220> FEATURE:
<223> OTHER INFORMATION: SS302-013M B chain

<400> SEQUENCE: 95

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```

<210> SEQ ID NO 96
<211> LENGTH: 299
<212> TYPE: PRT
<213> ORGANISM: Artificial Sequence
<220> FEATURE:
<223> OTHER INFORMATION: SS302-013M A chain-L-Fc16

<400> SEQUENCE: 96

```
Gly Ile Val Glu Gln Cys Cys Thr Ser Ile Cys Ser Leu Tyr Gln Leu
1               5                   10                  15

Glu Asn Tyr Cys Asn Gly Gly Ala Ala Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Val Ala Pro Pro Pro
    50                  55                  60

Ala Leu Pro Ala Pro Val Arg Leu Pro Gly Pro Ala Val Glu Cys Pro
65                  70                  75                  80

Pro Cys Pro Ala Pro Pro Val Ala Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Gln Phe Asn
        115                 120                 125

Trp Tyr Val Asp Gly Val Glu Val His Asn Ala Lys Thr Lys Pro Arg
    130                 135                 140

Glu Glu Gln Phe Asn Ser Thr Phe Arg Val Val Ser Val Leu Thr Val
145                 150                 155                 160

Val His Gln Asp Trp Leu Asn Gly Lys Glu Tyr Lys Cys Lys Val Ser
                165                 170                 175

Asn Lys Gly Leu Pro Ala Pro Ile Glu Lys Thr Ile Ser Lys Thr Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Met Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
        275                 280                 285

Thr Gln Lys Ser Leu Ser Leu Ser Pro Gly Lys
    290                 295
```

<210> SEQ ID NO 97
<211> LENGTH: 32
<212> TYPE: PRT
<213> ORGANISM: Artificial Sequence
<220> FEATURE:
<223> OTHER INFORMATION: SS302-014M B chain

<400> SEQUENCE: 97

```
Phe Val Asn Gln His Leu Cys Gly Ser His Leu Val Glu Ala Leu Tyr
1               5                   10                  15
```

```
Leu Val Cys Gly Glu Arg Gly Phe Phe Tyr Thr Pro Lys Thr Arg Arg
            20                  25                  30


<210> SEQ ID NO 98
<211> LENGTH: 299
<212> TYPE: PRT
<213> ORGANISM: Artificial Sequence
<220> FEATURE:
<223> OTHER INFORMATION: SS302-014M A chain-L-Fc5

<400> SEQUENCE: 98

Gly Ile Val Glu Gln Cys Cys Thr Ser Ile Cys Ser Leu Tyr Gln Leu
1               5                   10                  15

Glu Asn Tyr Cys Asn Gly Gly Ala Ala Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Val Ala Pro Pro Pro
    50                  55                  60

Ala Leu Pro Ala Pro Val Arg Leu Pro Gly Pro Ala Val Glu Cys Pro
65                  70                  75                  80

Pro Cys Pro Ala Pro Pro Val Ala Gly Pro Ser Val Phe Leu Phe Pro
                85                  90                  95

Pro Lys Pro Lys Asp Thr Leu Tyr Ile Thr Arg Glu Pro Glu Val Thr
            100                 105                 110

Cys Val Val Val Asp Val Ser His Glu Asp Pro Glu Val Gln Phe Asn
        115                 120                 125

Trp Tyr Val Asp Gly Val Glu Val His Asn Ala Lys Thr Lys Pro Arg
    130                 135                 140

Glu Glu Gln Phe Ala Ser Thr Phe Arg Val Val Ser Val Leu Thr Val
145                 150                 155                 160

Val His Gln Asp Trp Leu Asn Gly Lys Glu Tyr Lys Cys Lys Val Ser
                165                 170                 175

Asn Lys Gly Leu Pro Ala Pro Ile Glu Lys Thr Ile Ser Lys Thr Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Met Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
        275                 280                 285

Thr Gln Lys Ser Leu Ser Leu Ser Pro Gly Lys
    290                 295


<210> SEQ ID NO 99
<211> LENGTH: 32
<212> TYPE: PRT
<213> ORGANISM: Artificial Sequence
<220> FEATURE:
<223> OTHER INFORMATION: SS302-015M B chain

<400> SEQUENCE: 99
```

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 100
<211> LENGTH: 299
<212> TYPE: PRT
<213> ORGANISM: Artificial Sequence
<220> FEATURE:
<223> OTHER INFORMATION: SS302-015M A chain-L-Fc6

<400> SEQUENCE: 100

Gly Ile Val Glu Gln Cys Cys Thr Ser Ile Cys Ser Leu Tyr Gln Leu
1               5                   10                  15

Glu Asn Tyr Cys Asn Gly Gly Ala Ala Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Val Ala Pro Pro Pro
    50                  55                  60

Ala Leu Pro Ala Pro Val Arg Leu Pro Gly Pro Ala Val Glu Cys Pro
65                  70                  75                  80

Pro Cys Pro Ala Pro Pro Val Ala Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Gln Phe Asn
        115                 120                 125

Trp Tyr Val Asp Gly Val Glu Val His Asn Ala Lys Thr Lys Pro Arg
    130                 135                 140

Glu Glu Gln Phe Ala Ser Thr Phe Arg Val Val Ser Val Leu Thr Val
145                 150                 155                 160

Val His Gln Asp Trp Leu Asn Gly Lys Glu Tyr Lys Cys Lys Val Ser
                165                 170                 175

Asn Lys Gly Leu Pro Ala Pro Ile Glu Lys Thr Ile Ser Lys Thr Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Met Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Leu His Glu Ala Leu His Ser His Tyr
        275                 280                 285

Thr Gln Lys Ser Leu Ser Leu Ser Pro Gly Lys
    290                 295


<210> SEQ ID NO 101
<211> LENGTH: 32
<212> TYPE: PRT
<213> ORGANISM: Artificial Sequence
```

```
<220> FEATURE:
<223> OTHER INFORMATION: SS302-016M B chain

<400> SEQUENCE: 101

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 102
<211> LENGTH: 304
<212> TYPE: PRT
<213> ORGANISM: Artificial Sequence
<220> FEATURE:
<223> OTHER INFORMATION: SS302-016M A chain-L-Fc7

<400> SEQUENCE: 102

Gly Ile Val Glu Gln Cys Cys Thr Ser Ile Cys Ser Leu Tyr Gln Leu
1               5                   10                  15

Glu Asn Tyr Cys Asn Gly Gly Ala Ala Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Val Ala Pro Pro Pro
    50                  55                  60

Ala Leu Pro Ala Pro Val Arg Leu Pro Gly Pro Ala Glu Ser Lys Tyr
65                  70                  75                  80

Gly Pro Pro Cys Pro Pro Cys Pro Ala Pro Glu Ala Ala Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser Gln Glu Asp
        115                 120                 125

Pro Glu Val Gln Phe Asn Trp Tyr Val Asp Gly Val Glu Val His Asn
    130                 135                 140

Ala Lys Thr Lys Pro Arg Glu Glu Gln Phe Asn Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Gly Leu Pro Ser Ser Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Gln Glu Glu Met Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Arg Leu Thr Val Asp Lys
            260                 265                 270

Ser Arg Trp Gln Glu Gly Asn Val Phe Ser Cys Ser Val Met His Glu
        275                 280                 285

Ala Leu His Asn His Tyr Thr Gln Lys Ser Leu Ser Leu Ser Leu Gly
    290                 295                 300
```

<210> SEQ ID NO 103
<211> LENGTH: 32
<212> TYPE: PRT
<213> ORGANISM: Artificial Sequence
<220> FEATURE:
<223> OTHER INFORMATION: SS302-017M B chain

<400> SEQUENCE: 103

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```

<210> SEQ ID NO 104
<211> LENGTH: 304
<212> TYPE: PRT
<213> ORGANISM: Artificial Sequence
<220> FEATURE:
<223> OTHER INFORMATION: SS302-017M A chain-L-Fc8

<400> SEQUENCE: 104

```
Gly Ile Val Glu Gln Cys Cys Thr Ser Ile Cys Ser Leu Tyr Gln Leu
1               5                   10                  15

Glu Asn Tyr Cys Asn Gly Gly Ala Ala Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Val Ala Pro Pro Pro
    50                  55                  60

Ala Leu Pro Ala Pro Val Arg Leu Pro Gly Pro Ala Glu Ser Lys Tyr
65                  70                  75                  80

Gly Pro Pro Cys Pro Pro Cys Pro Ala Pro Glu Phe Leu Gly Gly Pro
                85                  90                  95

Ser Val Phe Leu Phe Pro Pro Lys Pro Lys Asp Thr Leu Tyr Ile Thr
            100                 105                 110

Arg Glu Pro Glu Val Thr Cys Val Val Val Asp Val Ser Gln Glu Asp
        115                 120                 125

Pro Glu Val Gln Phe Asn Trp Tyr Val Asp Gly Val Glu Val His Asn
    130                 135                 140

Ala Lys Thr Lys Pro Arg Glu Glu Gln Phe Ala Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Gly Leu Pro Ser Ser Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Gln Glu Glu Met Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Arg Leu Thr Val Asp Lys
            260                 265                 270

Ser Arg Trp Gln Glu Gly Asn Val Phe Ser Cys Ser Val Met His Glu
        275                 280                 285
```

Ala Leu His Asn His Tyr Thr Gln Lys Ser Leu Ser Leu Ser Leu Gly
    290                 295                 300

<210> SEQ ID NO 105
<211> LENGTH: 32
<212> TYPE: PRT
<213> ORGANISM: Artificial Sequence
<220> FEATURE:
<223> OTHER INFORMATION: SS302-018M B chain

<400> SEQUENCE: 105

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 106
<211> LENGTH: 304
<212> TYPE: PRT
<213> ORGANISM: Artificial Sequence
<220> FEATURE:
<223> OTHER INFORMATION: SS302-018M A chain-L-Fc9

<400> SEQUENCE: 106

Gly Ile Val Glu Gln Cys Cys Thr Ser Ile Cys Ser Leu Tyr Gln Leu
1               5                   10                  15

Glu Asn Tyr Cys Asn Gly Gly Ala Ala Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Val Ala Pro Pro Pro
    50                  55                  60

Ala Leu Pro Ala Pro Val Arg Leu Pro Gly Pro Ala Glu Ser Lys Tyr
65                  70                  75                  80

Gly Pro Pro Cys Pro Pro Cys Pro Ala Pro Glu Phe Leu Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser Gln Glu Asp
        115                 120                 125

Pro Glu Val Gln Phe Asn Trp Tyr Val Asp Gly Val Glu Val His Asn
    130                 135                 140

Ala Lys Thr Lys Pro Arg Glu Glu Gln Phe Ala Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Gly Leu Pro Ser Ser Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Gln Glu Glu Met Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Arg Leu Thr Val Asp Lys
            260                 265                 270

Ser Arg Trp Gln Glu Gly Asn Val Phe Ser Cys Ser Val Leu His Glu
275 280 285

Ala Leu His Ser His Tyr Thr Gln Lys Ser Leu Ser Leu Ser Leu Gly
290 295 300

<210> SEQ ID NO 107
<211> LENGTH: 32
<212> TYPE: PRT
<213> ORGANISM: Artificial Sequence
<220> FEATURE:
<223> OTHER INFORMATION: SS302-019M B chain

<400> SEQUENCE: 107

Phe Val Asn Gln His Leu Cys Gly Ser His Leu Val Glu Ala Leu Glu
1 5 10 15

Leu Val Cys Gly Glu Arg Gly Phe His Tyr Thr Pro Lys Thr Arg Arg
20 25 30

<210> SEQ ID NO 108
<211> LENGTH: 304
<212> TYPE: PRT
<213> ORGANISM: Artificial Sequence
<220> FEATURE:
<223> OTHER INFORMATION: SS302-019M A chain-L-Fc7

<400> SEQUENCE: 108

Gly Ile Val Glu Gln Cys Cys Thr Ser Ile Cys Ser Leu Glu Gln Leu
1 5 10 15

Glu Asn Tyr Cys Asn Gly Gly Ala Ala Val Ala Pro Pro Pro Ala Leu
20 25 30

Pro Ala Pro Val Arg Leu Pro Gly Pro Ala Val Ala Pro Pro Pro Ala
35 40 45

Leu Pro Ala Pro Val Arg Leu Pro Gly Pro Ala Val Ala Pro Pro Pro
50 55 60

Ala Leu Pro Ala Pro Val Arg Leu Pro Gly Pro Ala Glu Ser Lys Tyr
65 70 75 80

Gly Pro Pro Cys Pro Pro Cys Pro Ala Pro Glu Ala Ala Gly Gly Pro
85 90 95

Ser Val Phe Leu Phe Pro Pro Lys Pro Lys Asp Thr Leu Met Ile Ser
100 105 110

Arg Thr Pro Glu Val Thr Cys Val Val Val Asp Val Ser Gln Glu Asp
115 120 125

Pro Glu Val Gln Phe Asn Trp Tyr Val Asp Gly Val Glu Val His Asn
130 135 140

Ala Lys Thr Lys Pro Arg Glu Glu Gln Phe Asn Ser Thr Tyr Arg Val
145 150 155 160

Val Ser Val Leu Thr Val Leu His Gln Asp Trp Leu Asn Gly Lys Glu
165 170 175

Tyr Lys Cys Lys Val Ser Asn Lys Gly Leu Pro Ser Ser Ile Glu Lys
180 185 190

Thr Ile Ser Lys Ala Lys Gly Gln Pro Arg Glu Pro Gln Val Tyr Thr
195 200 205

Leu Pro Pro Ser Gln Glu Glu Met Thr Lys Asn Gln Val Ser Leu Thr
210 215 220

Cys Leu Val Lys Gly Phe Tyr Pro Ser Asp Ile Ala Val Glu Trp Glu
225 230 235 240

Ser Asn Gly Gln Pro Glu Asn Asn Tyr Lys Thr Thr Pro Pro Val Leu

```
                245                 250                 255

Asp Ser Asp Gly Ser Phe Phe Leu Tyr Ser Arg Leu Thr Val Asp Lys
            260                 265                 270

Ser Arg Trp Gln Glu Gly Asn Val Phe Ser Cys Ser Val Met His Glu
        275                 280                 285

Ala Leu His Asn His Tyr Thr Gln Lys Ser Leu Ser Leu Ser Leu Gly
    290                 295                 300


<210> SEQ ID NO 109
<211> LENGTH: 35
<212> TYPE: PRT
<213> ORGANISM: Artificial Sequence
<220> FEATURE:
<223> OTHER INFORMATION: SS302-022M B chain

<400> SEQUENCE: 109

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Arg
            20                  25                  30

Ile Lys Arg
        35


<210> SEQ ID NO 110
<211> LENGTH: 282
<212> TYPE: PRT
<213> ORGANISM: Artificial Sequence
<220> FEATURE:
<223> OTHER INFORMATION: SS302-022M A chain-L-Fc16

<400> SEQUENCE: 110

Gly Ile Val Glu Gln Cys Cys Thr Ser Ile Cys Ser Leu Tyr Gln Leu
1               5                   10                  15

Glu Asn Tyr Cys Asn Gly Gly Gly Ser Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Val Glu Cys Pro Pro
    50                  55                  60

Cys Pro Ala Pro Pro Val Ala Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Gln Phe Asn Trp
            100                 105                 110

Tyr Val Asp Gly Val Glu Val His Asn Ala Lys Thr Lys Pro Arg Glu
        115                 120                 125

Glu Gln Phe Asn Ser Thr Phe Arg Val Val Ser Val Leu Thr Val Val
    130                 135                 140

His Gln Asp Trp Leu Asn Gly Lys Glu Tyr Lys Cys Lys Val Ser Asn
145                 150                 155                 160

Lys Gly Leu Pro Ala Pro Ile Glu Lys Thr Ile Ser Lys Thr Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205
```

Pro Ser Asp Ile Ala Val Glu Trp Glu Ser Asn Gly Gln Pro Glu Asn
    210                 215                 220

Asn Tyr Lys Thr Thr Pro Pro Met Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 111
<211> LENGTH: 35
<212> TYPE: PRT
<213> ORGANISM: Artificial Sequence
<220> FEATURE:
<223> OTHER INFORMATION: SS302-023M B chain

<400> SEQUENCE: 111

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Asp Asp
            20                  25                  30

Asp Asp Lys
        35

<210> SEQ ID NO 112
<211> LENGTH: 282
<212> TYPE: PRT
<213> ORGANISM: Artificial Sequence
<220> FEATURE:
<223> OTHER INFORMATION: SS302-023M A chain-L-Fc16

<400> SEQUENCE: 112

Gly Ile Val Glu Gln Cys Cys Thr Ser Ile Cys Ser Leu Tyr Gln Leu
1               5                   10                  15

Glu Asn Tyr Cys Asn Gly Gly Gly Ser Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Val Glu Cys Pro Pro
    50                  55                  60

Cys Pro Ala Pro Pro Val Ala Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Gln Phe Asn Trp
            100                 105                 110

Tyr Val Asp Gly Val Glu Val His Asn Ala Lys Thr Lys Pro Arg Glu
        115                 120                 125

Glu Gln Phe Asn Ser Thr Phe Arg Val Val Ser Val Leu Thr Val Val
    130                 135                 140

His Gln Asp Trp Leu Asn Gly Lys Glu Tyr Lys Cys Lys Val Ser Asn
145                 150                 155                 160

Lys Gly Leu Pro Ala Pro Ile Glu Lys Thr Ile Ser Lys Thr Lys Gly
                165                 170                 175

Gln Pro Arg Glu Pro Gln Val Tyr Thr Leu Pro Pro Ser Arg Glu Glu
            180                 185                 190

```
Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Met Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280


<210> SEQ ID NO 113
<211> LENGTH: 32
<212> TYPE: PRT
<213> ORGANISM: Artificial Sequence
<220> FEATURE:
<223> OTHER INFORMATION: SS302-029M B chain

<400> SEQUENCE: 113

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys Thr Arg Arg
            20                  25                  30


<210> SEQ ID NO 114
<211> LENGTH: 304
<212> TYPE: PRT
<213> ORGANISM: Artificial Sequence
<220> FEATURE:
<223> OTHER INFORMATION: SS302-029M A chain-L-Fc8

<400> SEQUENCE: 114

Gly Ile Val Glu Gln Cys Cys Thr Ser Ile Cys Ser Leu Glu Gln Leu
1               5                   10                  15

Glu Asn Tyr Cys Asn Gly Gly Ala Ala Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Val Ala Pro Pro Pro
    50                  55                  60

Ala Leu Pro Ala Pro Val Arg Leu Pro Gly Pro Ala Glu Ser Lys Tyr
65                  70                  75                  80

Gly Pro Pro Cys Pro Pro Cys Pro Ala Pro Glu Phe Leu Gly Gly Pro
                85                  90                  95

Ser Val Phe Leu Phe Pro Pro Lys Pro Lys Asp Thr Leu Tyr Ile Thr
            100                 105                 110

Arg Glu Pro Glu Val Thr Cys Val Val Val Asp Val Ser Gln Glu Asp
        115                 120                 125

Pro Glu Val Gln Phe Asn Trp Tyr Val Asp Gly Val Glu Val His Asn
    130                 135                 140

Ala Lys Thr Lys Pro Arg Glu Glu Gln Phe Ala Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Gly Leu Pro Ser Ser Ile Glu Lys
```

```
            180                 185                 190

Thr Ile Ser Lys Ala Lys Gly Gln Pro Arg Glu Pro Gln Val Tyr Thr
        195                 200                 205

Leu Pro Pro Ser Gln Glu Glu Met Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Arg Leu Thr Val Asp Lys
            260                 265                 270

Ser Arg Trp Gln Glu Gly Asn Val Phe Ser Cys Ser Val Met His Glu
        275                 280                 285

Ala Leu His Asn His Tyr Thr Gln Lys Ser Leu Ser Leu Ser Leu Gly
    290                 295                 300


<210> SEQ ID NO 115
<211> LENGTH: 32
<212> TYPE: PRT
<213> ORGANISM: Artificial Sequence
<220> FEATURE:
<223> OTHER INFORMATION: SS302-030M B chain

<400> SEQUENCE: 115

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys Thr Arg Arg
            20                  25                  30


<210> SEQ ID NO 116
<211> LENGTH: 304
<212> TYPE: PRT
<213> ORGANISM: Artificial Sequence
<220> FEATURE:
<223> OTHER INFORMATION: SS302-030M A chain-L-Fc9

<400> SEQUENCE: 116

Gly Ile Val Glu Gln Cys Cys Thr Ser Ile Cys Ser Leu Glu Gln Leu
1               5                   10                  15

Glu Asn Tyr Cys Asn Gly Gly Ala Ala Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Val Ala Pro Pro Pro
    50                  55                  60

Ala Leu Pro Ala Pro Val Arg Leu Pro Gly Pro Ala Glu Ser Lys Tyr
65                  70                  75                  80

Gly Pro Pro Cys Pro Pro Cys Pro Ala Pro Glu Phe Leu Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser Gln Glu Asp
        115                 120                 125

Pro Glu Val Gln Phe Asn Trp Tyr Val Asp Gly Val Glu Val His Asn
    130                 135                 140

Ala Lys Thr Lys Pro Arg Glu Glu Gln Phe Ala Ser Thr Tyr Arg Val
145                 150                 155                 160
```

```
Val Ser Val Leu Thr Val Leu His Gln Asp Trp Leu Asn Gly Lys Glu
                165                 170                 175

Tyr Lys Cys Lys Val Ser Asn Lys Gly Leu Pro Ser Ser Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Gln Glu Glu Met Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Arg Leu Thr Val Asp Lys
            260                 265                 270

Ser Arg Trp Gln Glu Gly Asn Val Phe Ser Cys Ser Val Leu His Glu
        275                 280                 285

Ala Leu His Ser His Tyr Thr Gln Lys Ser Leu Ser Leu Ser Leu Gly
    290                 295                 300


<210> SEQ ID NO 117
<211> LENGTH: 30
<212> TYPE: PRT
<213> ORGANISM: Artificial Sequence
<220> FEATURE:
<223> OTHER INFORMATION: SS302-035M B chain

<400> SEQUENCE: 117

Phe Val Asn Gln His Leu Cys Gly Ser His Leu Val Glu Ala Leu His
1               5                   10                  15

Leu Val Cys Gly Glu Arg Gly Phe His Tyr Thr Pro Lys Arg
            20                  25                  30


<210> SEQ ID NO 118
<211> LENGTH: 287
<212> TYPE: PRT
<213> ORGANISM: Artificial Sequence
<220> FEATURE:
<223> OTHER INFORMATION: SS302-035M A chain-L-Fc15

<400> SEQUENCE: 118

Gly Ile Val Glu Gln Cys Cys Thr Ser Ile Cys Ser Leu Glu Gln Leu
1               5                   10                  15

Glu Asn Tyr Cys Asn Gly Gly Ala Ala Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Glu Ser Lys Tyr Gly
    50                  55                  60

Pro Pro Cys Pro Pro Cys Pro Ala Pro Glu Ala Ala Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser Gln Glu Asp Pro
            100                 105                 110

Glu Val Gln Phe Asn Trp Tyr Val Asp Gly Val Glu Val His Asn Ala
        115                 120                 125

Lys Thr Lys Pro Arg Glu Glu Gln Phe Asn Ser Thr Tyr Arg Val Val
    130                 135                 140
```

```
Ser Val Leu Thr Val Leu His Gln Asp Trp Leu Asn Gly Lys Glu Tyr
145                 150                 155                 160

Lys Cys Lys Val Ser Asn Lys Gly Leu Pro Ser Ser Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Gln Glu Glu Met Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Arg Leu Thr Val Asp Lys Ser
                245                 250                 255

Arg Trp Gln Glu Gly Asn Val Phe Ser Cys Ser Val Met His Glu Ala
            260                 265                 270

Leu His Asn His Tyr Thr Gln Lys Ser Leu Ser Leu Ser Leu Gly
        275                 280                 285


<210> SEQ ID NO 119
<211> LENGTH: 30
<212> TYPE: PRT
<213> ORGANISM: Artificial Sequence
<220> FEATURE:
<223> OTHER INFORMATION: SS302-036M B chain

<400> SEQUENCE: 119

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys Arg
            20                  25                  30


<210> SEQ ID NO 120
<211> LENGTH: 287
<212> TYPE: PRT
<213> ORGANISM: Artificial Sequence
<220> FEATURE:
<223> OTHER INFORMATION: SS302-036M A chain-L-Fc15

<400> SEQUENCE: 120

Gly Ile Val Glu Gln Cys Cys Thr Ser Ile Cys Ser Leu Glu Gln Leu
1               5                   10                  15

Glu Asn Tyr Cys Asn Gly Gly Ala Ala Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Glu Ser Lys Tyr Gly
    50                  55                  60

Pro Pro Cys Pro Pro Cys Pro Ala Pro Glu Ala Ala Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser Gln Glu Asp Pro
            100                 105                 110

Glu Val Gln Phe Asn Trp Tyr Val Asp Gly Val Glu Val His Asn Ala
        115                 120                 125

Lys Thr Lys Pro Arg Glu Glu Gln Phe Asn Ser Thr Tyr Arg Val Val
```

```
    130                 135                 140

Ser Val Leu Thr Val Leu His Gln Asp Trp Leu Asn Gly Lys Glu Tyr
145                 150                 155                 160

Lys Cys Lys Val Ser Asn Lys Gly Leu Pro Ser Ser Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Gln Glu Glu Met Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Arg Leu Thr Val Asp Lys Ser
                245                 250                 255

Arg Trp Gln Glu Gly Asn Val Phe Ser Cys Ser Val Met His Glu Ala
            260                 265                 270

Leu His Asn His Tyr Thr Gln Lys Ser Leu Ser Leu Ser Leu Gly
        275                 280                 285


<210> SEQ ID NO 121
<211> LENGTH: 30
<212> TYPE: PRT
<213> ORGANISM: Artificial Sequence
<220> FEATURE:
<223> OTHER INFORMATION: SS302-037M B chain

<400> SEQUENCE: 121

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Arg
            20                  25                  30


<210> SEQ ID NO 122
<211> LENGTH: 287
<212> TYPE: PRT
<213> ORGANISM: Artificial Sequence
<220> FEATURE:
<223> OTHER INFORMATION: SS302-037M A chain-L-Fc15

<400> SEQUENCE: 122

Gly Ile Val Glu Gln Cys Cys Thr Ser Ile Cys Ser Leu Glu Gln Leu
1               5                   10                  15

Glu Asn Tyr Cys Asn Gly Gly Ala Ala Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Glu Ser Lys Tyr Gly
    50                  55                  60

Pro Pro Cys Pro Pro Cys Pro Ala Pro Glu Ala Ala Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser Gln Glu Asp Pro
            100                 105                 110

Glu Val Gln Phe Asn Trp Tyr Val Asp Gly Val Glu Val His Asn Ala
        115                 120                 125
```

```
Lys Thr Lys Pro Arg Glu Glu Gln Phe Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Gly Leu Pro Ser Ser Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Gln Glu Glu Met Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Arg Leu Thr Val Asp Lys Ser
                245                 250                 255

Arg Trp Gln Glu Gly Asn Val Phe Ser Cys Ser Val Met His Glu Ala
            260                 265                 270

Leu His Asn His Tyr Thr Gln Lys Ser Leu Ser Leu Ser Leu Gly
        275                 280                 285


<210> SEQ ID NO 123
<211> LENGTH: 32
<212> TYPE: PRT
<213> ORGANISM: Artificial Sequence
<220> FEATURE:
<223> OTHER INFORMATION: SS302-038M B chain

<400> SEQUENCE: 123

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 124
<211> LENGTH: 287
<212> TYPE: PRT
<213> ORGANISM: Artificial Sequence
<220> FEATURE:
<223> OTHER INFORMATION: SS302-038M A chain-L-Fc15

<400> SEQUENCE: 124

Gly Ile Val Glu Gln Cys Cys Thr Ser Ile Cys Ser Leu Tyr Gln Leu
1               5                   10                  15

Glu Asn Tyr Cys Asn Gly Gly Ala Ala Val Ala Pro Pro Pro Ala Leu
            20                  25                  30

Pro Ala Pro Val Arg Leu Pro Gly Pro Ala Val Ala Pro Pro Pro Ala
        35                  40                  45

Leu Pro Ala Pro Val Arg Leu Pro Gly Pro Ala Glu Ser Lys Tyr Gly
    50                  55                  60

Pro Pro Cys Pro Pro Cys Pro Ala Pro Glu Ala Ala Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser Gln Glu Asp Pro
            100                 105                 110

Glu Val Gln Phe Asn Trp Tyr Val Asp Gly Val Glu Val His Asn Ala
        115                 120                 125
```

```
Lys Thr Lys Pro Arg Glu Glu Gln Phe Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Gly Leu Pro Ser Ser Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Gln Glu Glu Met Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Arg Leu Thr Val Asp Lys Ser
                245                 250                 255

Arg Trp Gln Glu Gly Asn Val Phe Ser Cys Ser Val Met His Glu Ala
            260                 265                 270

Leu His Asn His Tyr Thr Gln Lys Ser Leu Ser Leu Ser Leu Gly
        275                 280                 285


<210> SEQ ID NO 125
<211> LENGTH: 6
<212> TYPE: PRT
<213> ORGANISM: Artificial Sequence
<220> FEATURE:
<223> OTHER INFORMATION: Rigid unit
<220> FEATURE:
<221> NAME/KEY: MISC_FEATURE
<222> LOCATION: (4)..(4)
<223> OTHER INFORMATION: X1 can be any naturally occurring amino acid

<400> SEQUENCE: 125

Pro Pro Pro Xaa Leu Pro
1               5


<210> SEQ ID NO 126
<211> LENGTH: 8
<212> TYPE: PRT
<213> ORGANISM: Artificial Sequence
<220> FEATURE:
<223> OTHER INFORMATION: Rigid unit
<220> FEATURE:
<221> NAME/KEY: MISC_FEATURE
<222> LOCATION: (1)..(1)
<223> OTHER INFORMATION: X2 is K or V
<220> FEATURE:
<221> NAME/KEY: MISC_FEATURE
<222> LOCATION: (6)..(6)
<223> OTHER INFORMATION: X1 can be any naturally occurring amino acid

<400> SEQUENCE: 126

Xaa Ala Pro Pro Pro Xaa Leu Pro
1               5


<210> SEQ ID NO 127
<211> LENGTH: 22
<212> TYPE: PRT
<213> ORGANISM: Artificial Sequence
<220> FEATURE:
<223> OTHER INFORMATION: Rigid unit

<400> SEQUENCE: 127
```

-continued

```
Pro Pro Pro Ser Leu Pro Ser Pro Ser Arg Leu Pro Gly Pro Ser Asp
1               5                   10                  15

Thr Pro Ile Leu Pro Gln
            20


<210> SEQ ID NO 128
<211> LENGTH: 14
<212> TYPE: PRT
<213> ORGANISM: Artificial Sequence
<220> FEATURE:
<223> OTHER INFORMATION: Rigid unit

<400> SEQUENCE: 128

Pro Pro Pro Ala Leu Pro Ala Pro Val Arg Leu Pro Gly Pro
1               5                   10


<210> SEQ ID NO 129
<211> LENGTH: 15
<212> TYPE: PRT
<213> ORGANISM: Artificial Sequence
<220> FEATURE:
<223> OTHER INFORMATION: Rigid unit

<400> SEQUENCE: 129

Pro Pro Pro Ala Leu Pro Ala Val Ala Pro Pro Pro Ala Leu Pro
1               5                   10                  15


<210> SEQ ID NO 130
<211> LENGTH: 24
<212> TYPE: PRT
<213> ORGANISM: Artificial Sequence
<220> FEATURE:
<223> OTHER INFORMATION: Rigid unit

<400> SEQUENCE: 130

Lys Ala Pro Pro Pro Ser Leu Pro Ser Pro Ser Arg Leu Pro Gly Pro
1               5                   10                  15

Ser Asp Thr Pro Ile Leu Pro Gln
            20


<210> SEQ ID NO 131
<211> LENGTH: 16
<212> TYPE: PRT
<213> ORGANISM: Artificial Sequence
<220> FEATURE:
<223> OTHER INFORMATION: Rigid unit

<400> SEQUENCE: 131

Val Ala Pro Pro Pro Ala Leu Pro Ala Pro Val Arg Leu Pro Gly Pro
1               5                   10                  15


<210> SEQ ID NO 132
<211> LENGTH: 17
<212> TYPE: PRT
<213> ORGANISM: Artificial Sequence
<220> FEATURE:
<223> OTHER INFORMATION: Rigid unit

<400> SEQUENCE: 132

Val Ala Pro Pro Pro Ala Leu Pro Ala Val Ala Pro Pro Pro Ala Leu
1               5                   10                  15

Pro
```

INSULIN-Fc FUSION PROTEIN AND APPLICATION THEREOF

CROSS REFERENCE TO RELATED APPLICATIONS

This application is a U.S. National Phase Application of PCT International Application No. PCT/CN2021/107040, filed Jul. 19, 2021, which claims the priority of Chinese Patent Application No. 202010723972.9, filed with the China National Intellectual Property Administration on Jul. 24, 2020, and titled with "INSULIN-FC FUSION PROTEIN AND APPLICATION THEREOF." The contents of these applications are incorporated herein by reference in their entirety.

FIELD

The present disclosure relates to the field of polypeptide drugs, in particular to an insulin-Fc fusion protein with enhanced insulin activity and prolonged in vivo half-life after being cleaved by site-specific protease, a preparation method thereof and an application thereof.

BACKGROUND

In recent years, the incidence of diabetes has been increasing year by year. For type I diabetes, blood glucose is controlled mainly by exogenous insulin; and for type 2 diabetes, insulin has become the main drug for blood glucose control as the disease progresses. Therefore, the use of insulin to treat diabetes has become an effective way.

Insulin therapy is necessary for patients with abnormal insulin secretion (type I) or insulin resistance (type II), and blood glucose levels can be normally regulated by insulin administration. However, like other protein and peptide hormones, insulin has a very short in vivo half-life and thus suffers from the disadvantage of repeated administration. Such frequent administration causes severe pain and discomfort to the patient. For this reason, many studies have been carried out on protein formulations and chemical conjugation (fatty acid conjugates, polyethylene polymer conjugates) in order to improve the quality of life by prolonging the in vivo half-life of proteins and reducing the frequency of administration. Commercially available long-acting insulins include insulin glargine (lantus, lasting about 20 hours to 22 hours) manufactured by Sanofi Aventis, and insulin detemir (levemir, lasting about 18 hours to 22 hours) and tresiba (insulin degludec, lasting about 40 hours) manufactured by Novo Nordisk. These long-acting insulin formulations do not produce peaks in blood insulin concentration, which makes them suitable as basal insulins. However, since these formulations do not have a sufficiently long half-life, there is still the disadvantage of being injected once a day or every two to three days. Thus, there are limitations in achieving the intended goal of once-weekly dosing frequency to improve convenience for diabetic patients requiring long-term insulin administration.

Patent publication CN103509118B discloses a single-chain insulin fused to the Fc region of an antibody. Although this insulin-Fc fusion protein has showed an improved half-life in in vitro experiments, it has low in vivo hypoglycemic activity and is not suitable for clinical use.

The success in controlling diabetes is highly correlated with the compliance of the patient being treated, and it is desirable to reduce the frequency of injections required. However, these existing modified insulin molecules are either very inactive and not suitable for clinical use, or very active and have a rapid hypoglycemic effect after administration to patients, resulting in the side effect of hypoglycemia. Therefore, there is an urgent need in the field for a novel long-acting insulin suitable for clinical use.

SUMMARY

After extensive research, the inventors provide an insulin-Fc fusion protein, which can obtain enhanced insulin activity and prolonged in vivo half-life after being cleaved by site-specific protease, and it is surprisingly found that the fusion protein has steady and stable in vivo hypoglycemic effect, which can improve the safety of clinical medication and patient compliance, thereby better achieving blood glucose management and providing a better quality of life.

In a first aspect, the present disclosure provides an insulin-Fc fusion protein with enhanced insulin activity and prolonged in vivo half-life after being cleaved by site-specific protease, having the structure of formula (I):

X-E1-Y-E2-Z-L-Fc (I), wherein,

- X and Z are the B and A chains of insulin, respectively; if X is the B chain, then Z is the A chain, and if X is the A chain, then Z is the B chain.
- Y is an optional linking peptide and may comprise 1-100 or more amino acids in length, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100 amino acids or a value between any two of the values; for example, Y is insulin C-peptide or a variant or fragment thereof.

One or both of E1 and E2 are present and are an amino acid fragment comprising a site-specific protease cleavage site; E1 and E2 each may comprise 1-10 or more amino acids in length, such as 1, 2, 3, 4, 5, 6, 7, 8, 9 or 10 amino acids; if present at the same time, E1 and E2 may be cleaved by the same or different site-specific proteases, such as by the same site-specific protease; if Y is present, preferably both E1 and E2 are present; if Y is absent, preferably one of E1 and E2 is present; the site-specific protease cleavage site may be a cleavage site of Kex2 and/or Furin protease, such as a cleavage site of Kex2 protease.

L is a linker linking Z and Fc; L may be a polypeptide fragment, for example, L comprises a flexible unit (also referred to as a flexible peptide fragment herein) of one, two or more amino acids selected from Ala, Thr, Gly and Ser, such as a flexible unit consisting of G and S; L may also be a polypeptide fragment comprising a rigid unit (also referred to as a rigid peptide fragment herein).

In some embodiments, the rigid unit comprises or consists essentially of rigid amino acids, the rigid amino acids including but not limited to V, P, I, K and L.

In some embodiments, the rigid unit comprises one or more PPP$X_1$LP (SEQ ID NO: 125), wherein $X_1$ is any amino acid;

In other embodiments, the rigid unit comprises one or more $X_2$APPP$X_1$LP (SEQ ID NO: 126), wherein $X_1$ is any amino acid and $X_2$ is K or V.

In other embodiments, the rigid unit comprises a polypeptide fragment selected from the group consisting of:

```
(SEQ ID NO: 127)
PPPSLPSPSRLPGPSDTPILPQ;

(SEQ ID NO: 128)
PPPALPAPVRLPGP;
and

(SEQ ID NO: 129)
PPPALPAVAPPPALP.
```

In other embodiments, the rigid unit comprises a polypeptide fragment selected from the group consisting of:

```
(SEQ ID NO: 130)
KAPPPSLPSPSRLPGPSDTPILPQ;

(SEQ ID NO: 131)
VAPPPALPAPVRLPGP;
and

(SEQ ID NO: 132)
VAPPPALPAVAPPPALP.
```

In some embodiments, L comprises both rigid and flexible units, and may be more than two units.

Fc is the Fc region of an immunoglobulin; Fc may be derived from a human immunoglobulin; the Fc region may be an Fc region derived from IgG, IgA, IgD, IgE or IgM; preferably, the Fc region is an Fc region derived from IgG, such as an Fc region derived from IgG1, IgG2, IgG3 or IgG4; further preferably, the Fc region is an Fc region derived from IgG2; or compared to the sequence from which it is derived, the Fc region may have one or more substitutions, additions and/or deletions while still retains the ability to prolong half-life, for example, the Fc region is derived from human IgG and has a mutation that reduces or eliminates the binding to FcγR and/or a mutation that enhances the binding to FcRn, the mutation may be selected from the group consisting of: N297A, G236R/L328R, L234A/L235A, N434A, M252Y/S254T/T256E, M428L/N434S, T250R/M428L and a combination thereof, and the Fc region may be glycosylated or unglycosylated.

In some embodiments, for the fusion protein of the present disclosure, the insulin is selected from human insulin, bovine insulin or porcine insulin, preferably human insulin; for example, the A and B chains of insulin are derived from human insulin.

In some embodiments, Y, E1 and E2 are all present, or wherein Y is absent and one of E1 and E2 is present.

In other embodiments, the fusion protein comprises an amino acid sequence selected from the group consisting of SEQ ID NOs: 47-72.

In a second aspect, the present disclosure provides an insulin-Fc fusion protein with a structure of Ins-L-Fc. In some embodiments, the C-peptide may be removed from the fusion protein of the first aspect of the present disclosure by a specific protease to produce the fusion protein of the second aspect of the present disclosure. In some embodiments, the insulin-Fc fusion protein exists in the form of a homodimer, the structural diagram of which is shown in FIG. 3. In some embodiments, the insulin-Fc fusion protein has secondary and tertiary structures similar to natural insulin.

Wherein, Ins is an insulin moiety providing insulin activity and comprises A and B chains of insulin linked by a covalent bond and located in different peptide chains; the covalent bond is preferably a disulfide bond.

L is a linker linking Z and Fc; L may be a polypeptide fragment (also referred to as a linking peptide in some embodiments herein), for example, L comprises a flexible unit of one, two or more amino acids selected from Ala, Thr, Gly and Ser; L may also be a polypeptide fragment comprising a rigid unit.

In some embodiments, L comprises one or more rigid units comprising or consisting essentially of rigid amino acids, the rigid amino acids including but not limited to V, P, I, K and L.

In other embodiments, the rigid unit comprises one or more PPP$X_1$LP (SEQ ID NO: 125), wherein $X_1$ is any amino acid.

In other embodiments, the rigid unit comprises one or more $X_2$APPP$X_1$LP (SEQ ID NO: 126), wherein $X_1$ is any amino acid and $X_2$ is K or V.

In other embodiments, the rigid unit comprises a polypeptide fragment selected from the group consisting of:

```
(SEQ ID NO: 127)
PPPSLPSPSRLPGPSDTPILPQ;

(SEQ ID NO: 128)
PPPALPAPVRLPGP;
and

(SEQ ID NO: 129)
PPPALPAVAPPPALP.
```

In other embodiments, the rigid unit comprises a polypeptide fragment selected from the group consisting of:

```
(SEQ ID NO: 130)
KAPPPSLPSPSRLPGPSDTPILPQ;

(SEQ ID NO: 131)
VAPPPALPAPVRLPGP;
and

(SEQ ID NO: 132)
VAPPPALPAVAPPPALP.
```

Fc is the Fc region of an immunoglobulin; Fc may be derived from a human immunoglobulin; the Fc region may be an Fc region derived from IgG, IgA, IgD, IgE or IgM; preferably, the Fc region is an Fc region derived from IgG, such as an Fc region derived from IgG1, IgG2, IgG3 or IgG4; further preferably, the Fc region is an Fc region derived from IgG2; or compared to the sequence from which it is derived, the Fc region may have one or more substitutions, additions and/or deletions while still retains the ability to prolong half-life, for example, the Fc region is derived from human IgG and has a mutation that reduces or eliminates the binding to FcγR and/or a mutation that enhances the binding to FcRn, the mutation is selected from the group consisting of: N297A, G236R/L328R, L234A/L235A, N434A, M252Y/S254T/T256E, M428L/N434S, T250R/M428L and a combination thereof, and the Fc region may be glycosylated or unglycosylated.

In some embodiments, the insulin is selected from human insulin, bovine insulin or porcine insulin, preferably human insulin; for example, the A and B chains of the insulin are derived from human insulin.

In other embodiments, L comprises CTP, for example, 1, 2, 3 or more CTPs.

In a third aspect, the present disclosure provides a method for producing an insulin-Fc fusion protein with enhanced insulin activity and prolonged half-life, comprising contacting the fusion protein described in the first aspect of the present disclosure with a site-specific protease capable of cleaving the site-specific protease cleavage site, preferably the site-specific protease is Kex2 and/or Furin protease.

In some embodiments, the insulin-Fc fusion protein with enhanced insulin activity and prolonged in vivo half-life of the present disclosure is obtained by the above method.

In a fourth aspect, the present disclosure provides a polynucleotide encoding the fusion protein, preferably the polynucleotide is an expression vector capable of expressing the fusion protein.

In a fifth aspect, the present disclosure provides a cell capable of expressing an insulin-Fc fusion protein, comprising the above-described polynucleotide.

In a sixth aspect, the present disclosure provides a method for producing an insulin-Fc fusion protein, comprising culturing the cells described in the fifth aspect of the present disclosure under conditions for expressing the insulin-Fc fusion protein; preferably further comprising contacting the insulin-Fc fusion protein with a site-specific protease capable of cleaving the site-specific protease cleavage site, wherein the culturing and the contacting may be performed simultaneously or separately. The method may also comprise a protein purification step to obtain the target fusion protein.

In a seventh aspect, the present disclosure provides a method for characterizing the structure of an insulin-Fc fusion protein, comprising detecting the deglycosylated molecular weight of the fusion protein and characterizing disulfide bonds.

In an eighth aspect, the present disclosure provides a pharmaceutical composition comprising the fusion protein described in the first and third aspects, the polynucleotide described in the fourth aspect or the cell described in the fifth aspect.

In a ninth aspect, the present disclosure provides a method for lowering blood glucose and/or treating diabetes, comprising administering the fusion protein described in the first and second aspects, the polynucleotide described in the fourth aspect or the cell described in the fifth aspect to a subject in need thereof, preferably the diabetes is type I or type II diabetes. Furthermore, when administering the fusion protein described in the first aspect of the present disclosure, additional administration of appropriate site-specific protease, or utilization of appropriate site-specific proteases present in the body, may also be considered.

Corresponding to the above methods for lowering blood glucose and/or treating diabetes, the present disclosure also provides use of the fusion protein, polynucleotide or cell in the manufacture of a medicament for lowering blood glucose and/or treating diabetes. The present disclosure also provides the fusion protein, polynucleotide or cell for lowering blood glucose and/or treating diabetes.

BRIEF DESCRIPTION OF DRAWINGS

FIG. 1 shows a schematic diagram of the vector for the expression of insulin precursor fusion protein of the present disclosure; wherein, FIG. 1A shows a stable transfection expression vector, and FIG. 1B shows a transient transfection expression vector.

DETAILED DESCRIPTION

Figure 1:
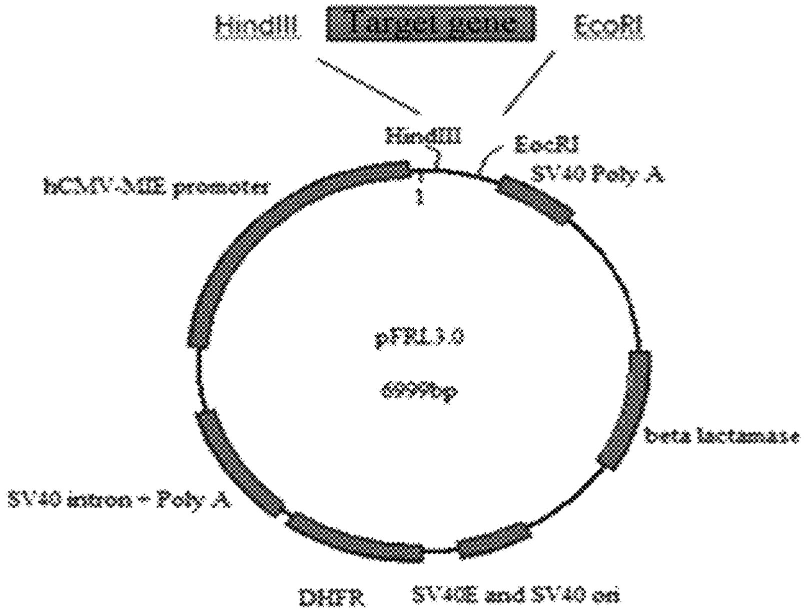
Figure 1:
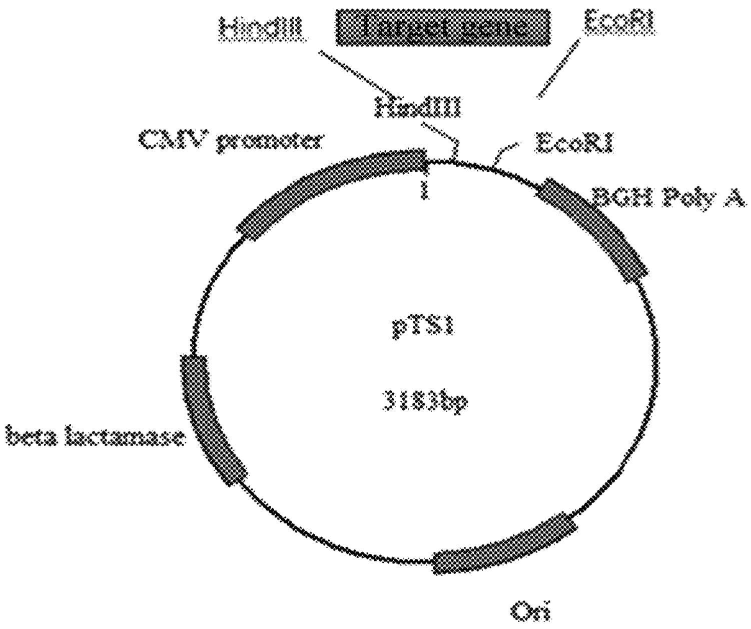

Next, the present disclosure will be described in more detail in conjunction with the embodiments. It is apparent that the described embodiments are only a part of the embodiments of the present disclosure, rather than all of the embodiments. Based on the embodiments of the present disclosure, all other embodiments obtained by those of ordinary skill in the art without creative efforts shall fall within the protection scope of the present disclosure.

Terms

Insulin

Insulin is a hormone secreted by pancreatic β cells to promote glucose uptake and inhibit fat degradation, thus acting to control blood glucose levels. In the nucleus of R cells, the DNA of the insulin gene region on the shorter arm of Chromosome 11 is transcribed into mRNA, and the mRNA moves from the nucleus to the endoplasmic reticulum in the cytoplasm, and is translated into preproinsulin, which consists of 106 amino acid residues and contains a signal peptide of about 20 residues at the N-terminal. When preproinsulin passes through the endoplasmic reticulum membrane, the signal peptide is removed by signal peptidase to form a long peptide chain, proinsulin, consisting of 86 amino acids. Proinsulin is cleaved by proteolytic enzymes in the Golgi apparatus to cut off two arginine residues at positions 31 and 32, a lysine residue at position 64 and an arginine residue at position 65. The cleaved chain is called the C-peptide serving as a linking moiety, and the simultaneously produced insulin is secreted out of β cells into the blood circulation. A small part of proinsulin that has not been hydrolyzed by protease enters the blood circulation along with insulin. Proinsulin has almost no biological activity, only 5%-10% of insulin.

The "insulin" of the present disclosure includes not only naturally occurring insulin, but also functional variants of insulin. The functional variant refers to a polypeptide that is obtained by modifications, such as additions, deletions and/or substitution of one or more amino acids, to the native sequence and/or structure of insulin and still has insulin activity (regulating blood glucose levels in the body). The substitution, addition or deletion of an amino acid may be a naturally occurring mutant form or an artificially modified mutant form for specific purposes. It is well known to those of ordinary skill in the art that in practice, functional variants of insulin are often also referred to as insulin. Another example is the insulin analogs disclosed in CN105636979 B and CN 201480006998. With reference to this specification, this practice is also covered herein.

From another aspect, a functional variant of insulin refers to a polypeptide that has at least 80% (preferably 85%, 90%, 91%, 92%, 93%, 94%, 95%, 96%, 97%, 98%, 99%, or 100%) amino acid sequence homology to natural insulin, and still has insulin activity. For some functional variants, chemical substitutions (e.g., α-methylation, α-hydroxylation), deletions (e.g., deamination), or modifications (e.g., N-methylation) are possible at some groups of specific amino acid residues.

Those skilled in the art are familiar with the methods of preparing functional variants of insulin and methods of testing their effects, and the insulin analogs that have been marketed include, for example, insulin lispro (Eli Lilly), insulin aspart (Novo Nordisk), insulin glulisine (Aventis), insulin glargine (Sanofi), insulin detemir (Novo Nordisk), and insulin degludec (Novo Nordisk).

For insulin lispro, proline at position 28 and lysine at position 29 on the B chain of human insulin are reversed, and the other amino acid sequence and structure remain unchanged. As a result of the reversal of the two amino acids, the function of insulin has not been changed, but the insulin, which used to form dimers and hexamers easily, no longer aggregates easily into dimers and hexamers, but exists in the form of monomers. Therefore, it will be easily absorbed after subcutaneous injection, resulting in a rapid onset of action.

Insulin aspart is also a fast-acting insulin, in which the proline at position B28 of human insulin is substituted by aspartic acid, so that this insulin analog is less prone to aggregate as a hexamer, which makes it easily absorbed subcutaneously for rapid action.

Insulin glulisine uses lysine instead of asparagine at position B3 and glutamic acid instead of lysine at position B29 to achieve a rapid onset of action.

Insulin glargine (Lantus) differs from human insulin in that 1) the asparagine at position 21 of the A chain is substituted by glycine; 2) two arginine residues are added to the C-terminal of the B chain. The result of such changes are as follows: the substitution at position A21 by glycine leads to a more stable binding of hexamer, and in the neutral environment of the subcutaneous tissue, the solubility decreases to form precipitate, resulting in slow absorption, similar to the peakless secretion of basal insulin, which is suitable for long-acting treatment, and its action time will be further prolonged if a small amount of zinc is added; the addition of two arginine residues to the C-terminal of the B chain changes the isoelectric point of insulin, rising from the original pH 4.5 to pH 6.7, which allows the formation of micro-precipitates in the neutral environment of subcutaneous tissues and prolongs the decomposition, absorption and action time of insulin.

For insulin detemir (Levermir), which is developed and produced by Novo Nordisk, structurally, the amino acid at position B30 is deleted, and a 14-carbon fatty acid chain of N-16-alkanoic acid group is linked at the lysine at position B29. In the drug solution with zinc ions, the insulin molecule still exists in the form of hexamer. The modification of the fatty acid chain leads to slow subcutaneous absorption, and the insulin detemir in the plasma will bind to the albumin in the plasma due to the presence of the fatty acid, while only free insulin detemir can play a hypoglycemic effect, which also prolongs the action time of insulin.

For insulin degludec, the threonine at position B30 is deleted, and a 16-carbon fatty diacid side chain is linked at the lysine at position B29 via a glutamic acid linker. Under the action of phenol and zinc ions, insulin degludec aggregates into double hexamers in the preparation. After subcutaneous injection, with the diffusion of phenol and the slow release of zinc ions, insulin degludec monomer can be slowly and continuously released, and then absorbed into the blood. Based on the above characteristics, insulin degludec has an ultra-long action time in diabetic patients with a half-life of about 25 hours.

Fusion Protein

The fusion protein described herein refers to both a protein formed by amino acids linked by peptide bonds and a protein formed from two or more peptide chains linked by disulfide bonds.

The "insulin-Fc fusion protein" in the present disclosure refers to a fusion protein formed by insulin (including functional variants thereof) and the Fc region of an immunoglobulin, and is sometimes simply referred to as "fusion protein" herein. In addition, in order to distinguish between the insulin-Fc fusion proteins before and after the cleavage of the linking peptide moiety by enzyme, the fusion protein before the cleavage by enzyme is sometimes referred to as "insulin precursor-Fc fusion protein", and the corresponding "insulin-Fc fusion protein" used refers to the fusion protein after the cleavage of the linking peptide moiety by enzyme. However, it is more common herein to not specifically distinguish between the fusion proteins before and after the cleavage by enzyme, in which case the fusion protein or insulin-Fc fusion protein encompasses its forms both before and after the cleavage by enzyme. In addition, when it is clear from the context which form the fusion protein refers to, "fusion protein" or "insulin-Fc fusion protein" is often used directly to refer to this form.

The sequence of A chain in natural human insulin is:

```
                                        (SEQ ID NO: 1)
Gly-Ile-Val-Glu-Gln-Cys-Cys-Thr-Ser-Ile-Cys-Ser-

Leu-Tyr-Gln-Leu-Glu-Asn-Tyr-Cys-Asn
```

The sequence of B chain in natural human insulin is:

```
                                        (SEQ ID NO: 2)
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr
```

The fusion protein described herein may also comprise an additional sequence that prolongs in vivo half-life, and for example, the additional sequence is selected from one or more of Fc, CTP (C-terminal peptide), XTEN, SABA (serum albumin binding adnectin) and PAS. The additional sequence may be located at the terminal, linker or other positions in the fusion protein. For simplicity, the structural formulae X-E1-Y-E2-Z-L-Fc and Ins-L-Fc used herein encompass also these cases where the additional sequence is located at other positions.

Linking Peptide

During the in vivo processing of insulin, the linking peptide linking the A and B chains of insulin is C-peptide. C-peptide includes both its naturally-occurring sequence and a variant form with the same function formed by substitution, deletion or addition of one or more amino acids based on the naturally-occurring sequence.

As a reference, the sequence of C-peptide of human insulin in its natural form is:

```
                                            (SEQ ID NO: 3)
Glu-Ala-Glu-Asp-Leu-Gln-Val-Gly-Gln-Val-Glu-Leu-

Gly-Gly-Gly-Pro-Gly-Ala-Gly-Ser-Leu-Gln-Pro-Leu-

Ala-Leu-Glu-Gly-Ser-Leu-Gln
```

In the insulin-Fc fusion protein of the present disclosure, the linking peptide is not limited to the C-peptide of natural insulin or the variant/fragment thereof, but can also be any other suitable polypeptide linking the A and B chains of insulin. In some embodiments, the linking peptide may comprise 1-100 or more amino acids in length, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100 amino acids, or a value between any two of the values above.

In some embodiments, the sequence of the linking peptide is:

```
                                            (SEQ ID NO: 4)
EAEDLQVGQVELGGGPGAGSLQPLALEGSL

                                            (SEQ ID NO: 5)
Glu-Ala-Glu-Asp-Leu-Gln-Val-Gly-Gln-Val-Glu-Leu-

Gly-Gly-Gly-Pro-Gly-Ala-Gly-Ser,

                                            (SEQ ID NO: 6)
Glu-Ala-Glu-Asp-Leu-Gln-Val-Gly-Gln-Val-Glu-Leu-

Gly-Gly-Gly,
or

                                            (SEQ ID NO: 7)
EAEDLQVGQVELSLQPLAL.
```

In other embodiments, the linking peptide may be in the form of a polypeptide of any length:

```
                        (SEQ ID NO: 8)
EAED,

                        (SEQ ID NO: 9)
YPGDV,

                        (SEQ ID NO: 10)
AA,
or

                        (SEQ ID NO: 11)
EW.
```

Human immunoglobulin IgG is composed of four polypeptides (two identical copies of light chain and heavy chain) covalently linked by disulfide bonds. The proteolysis of IgG molecules by papain produces two Fab fragments and one Fc fragment. The Fc fragment is composed of two polypeptides linked together by disulfide bonds. Each polypeptide, from N- to C-terminal, consists of hinge region, CH2 domain and CH3 domain. The structure of the Fc fragment is almost the same in all subtypes of human immunoglobulin. IgG is one of the most abundant proteins in human blood, which constitutes 70% to 75% of total immunoglobulin in human serum.

The Fc region of immunoglobulin is safe to be used as a pharmaceutical carrier because it is a biodegradable polypeptide that can be metabolized in the body. In addition, compared with the entire immunoglobulin molecule, the Fc region of immunoglobulin has a relatively low molecular weight, which is beneficial to the preparation, purification and production of fusion proteins. Since the immunoglobulin Fc region does not contain Fab fragment (its amino acid sequence varies according to the antibody subclass and is therefore highly heterogeneous), it is expected that the immunoglobulin Fc region can greatly increase the homogeneity of the substance and have low antigenicity It is generally understood by those of ordinary skill in the art that the term "Fc region of an immunoglobulin" refers to a protein fragment comprising heavy chain constant region 2 (CH2) and heavy chain constant region 3 (CH3) of an immunoglobulin but not comprising the variable regions of the heavy and light chains of an immunoglobulin. It may also contain the hinge region in the heavy chain constant region. Furthermore, the Fc fragment used in the present disclosure may contain part or all of the Fc region containing heavy chain constant region 1 (CH1) and/or the light chain constant region 1 (CL1) without variable regions of heavy chain and light chain, as long as it has a physiological function that is basically similar to or better than that of natural protein. Moreover, it may be an Fc fragment with a relatively long deletion in the amino acid sequences of CH2 and/or CH3. For example, the immunoglobulin Fc region used in the present disclosure may comprise 1) CH1 domain, CH2 domain and CH3 domain; 2) CH1 domain and CH2 domain; 3) CH1 domain and CH3 domain; 4) CH2 domain and CH3 domain; 5) CH1 domain, CH2 domain, CH3 or CL domain; 6) the combination of one or more constant region domains with (part or all of) the immunoglobulin hinge region; or 7) the dimer of any domains of heavy chain constant region and light chain constant region. In summary, the Fc region of an immunoglobulin in the present disclosure refers to any form of Fc or variants/derivatives thereof comprising one or more constant region domains of heavy/light chain or variants thereof and capable of imparting a function of prolonging in vivo half-life to the fusion protein, such as a single chain Fc, a monomeric Fc.

Besides, the immunoglobulin Fc region of the present disclosure comprises natural amino acid sequence and sequence variants (mutants) thereof. Owing to one or more deletions, insertions, non-conservative or conservative substitutions, or combination thereof of amino acid residues, the amino acid sequence derivative may have a sequence different from the natural amino acid sequence. For example, for IgG Fc, amino acid residues at positions 214 to 238, 297 to 299, 318 to 322, or 327 to 331 that are known to be critical to binding can be used as suitable targets for modification. The immunoglobulin Fc region of the present disclosure may also comprise a variety of other derivatives, including those without the region capable of forming disulfide bonds, those having several amino acid residues deletion at the N-terminal of the natural Fc, or those having additional methionine residues to the N-terminal of the natural Fc. In addition, to get rid of effector functions, deletion may be designed at complement binding site, such as C1q binding site and ADCC site. Techniques for preparing such derivatives of the immunoglobulin Fc region are disclosed in WO 97/34631 and WO 96/32478, which are incorporated herein by reference in their entirety. In addition, it is well known to those of ordinary skill in the art that the mutation of one or more amino acids in the Fc region can enhance the affinity of Fc to FcRn and prolong half-life in serum, such as the T250Q/M428L mutation (CN 1798767 B), and these mutant forms of Fc regions are also within the meaning of the Fc region of the present disclosure.

For proteins and peptides, amino acid substitutions that generally do not change the molecular activity are known in the art (H. Neurath, R. L. Hill, The Proteins, Academic Press, New York, 1979). The most common substitutions are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in either way.

If necessary, the Fc region is allowed to be modified, such as phosphorylation, sulfation, acrylate, glycosylation, methylation, farnesylation, acetylation, and amidation.

The Fc derivatives have the same biological activity as the Fc region in the present disclosure or have improved structural stability (such as structural stability to heat, pH, etc.) than the corresponding Fc region thereof.

In addition, these Fc regions can be derived from natural forms isolated from human and other animals including cattle, goat, pig, mouse, rabbit, hamster, rat and guinea pig, or derived from recombinant or derivative of transformed animal cells or microorganisms. Herein, the Fc region can be obtained from natural immunoglobulin by separating intact immunoglobulin from human or animal organisms and treating them with proteolytic enzymes. Papain digests natural immunoglobulin into Fab and Fc regions, while pepsin treatment results in the production of pFc' and $F(ab')_2$ fragments. Fc or pFc' fragments can be isolated, e.g., by size exclusion chromatography.

In addition, the immunoglobulin Fc region of the present disclosure may be a form having natural sugar chains, or increased or reduced sugar chains compared to the natural form, or may be a deglycosylated form. The increase, decrease or removal of immunoglobulin Fc sugar chains can be accomplished by methods commonly used in the art, such as chemical methods, enzymatic methods, genetic engineering methods or methods of mutating the N297 glycosylation site. Removal of sugar chains from the Fc fragment results in a significant reduction in binding affinity to complement (C1q) and reduction or loss of antibody-dependent cell-mediated cytotoxicity or complement-dependent cytotoxicity, and thereby unnecessary in vivo immune responses will not be induced. In view of this, the immunoglobulin Fc region in deglycosylated or unglycosylated form may be more suitable for the purpose of the present disclosure for use as a medicament.

The term "deglycosylation" as used in the present disclosure means the enzymatic removal of carbohydrate moiety from the Fc region, and the term "unglycosylation" means that the Fc region is produced in an aglycosylated form by prokaryotes (preferably *E. coli*), or by a method of mutating the N297 glycosylation site to G, A or any other amino acid.

In addition, the immunoglobulin Fc region may be an Fc region derived from IgG, IgA, IgD, IgE, and IgM, or prepared by a combination or hybrid thereof. Preferably, it is derived from IgG or IgM (two of the most abundant proteins in human blood), most preferably IgG (which is known to extend the half-life of ligand-binding protein)

The term "combination" as used in the present disclosure means a dimer or a multimer formed by two or more single-chain polypeptides which are linked together, where the single-chain polypeptides can be derived from the same or different immunoglobulin Fc region. That is, the dimer or the multimer may be formed by two or more fragments selected from the group consisting of IgG Fc fragment, IgA Fc fragment, IgM Fc fragment, IgD Fc fragment, and IgE Fc fragment.

Proteolysis by Protease

Proinsulin is inactive or very low in activity, and the conventional process for preparing recombinant insulin in the prior art is to express protein by *Escherichia coli* or yeast, and then process the expressed protein into an active molecule with trypsin or trypsin plus carboxypeptidase B. However, when the Fc region of the antibody is used to form a conjugate with insulin, the conventional preparation process cannot be used because there are many trypsin cleavage sites on the Fc, which will be cleaved and become inactive during processing proinsulin into an active molecule. In the prior art, in order to avoid this problem, single-chain insulin is directly conjugated with the Fc region. However, the inventors have found through research that such insulin has very low in vivo activity.

The inventors unexpectedly found that if the mature mechanism of insulin in vivo is simulated and the insulin conjugate is prepared which has a more similar structure to natural insulin (the A and B chain in the mature molecule are linked by disulfide bonds) and is linked to an Fc region, the activity of insulin can be greatly improved. After extensive screening, the inventors found that an active long-acting insulin conjugate molecule can be obtained by preparing the fusion polypeptide with the structure of the present disclosure, introducing a protease cleavage site of Kex2 or Furin protease, and then processing with the protease.

The Kex2 protease described in the present disclosure is a calcium ion-dependent protease, which can specifically recognize and cleave the carboxyl-terminal peptide bond of bibasic amino acids such as Arg-Arg and Lys-Arg. Unlike trypsin, Kex2 cannot recognize and cleave the carboxy-terminal peptide bond of a single basic amino acid, namely arginine or lysine. The Kex2 protease is responsible for processing precursors of killer toxin and α-factor in yeast. The activity of Kex2 protease is not inhibited by conventional serine protease inhibitors such as aprotinin, PMSF and TPCK.

Furin described in the present disclosure is an important endoprotease in eukaryotic cells. It is located in the network outside the Golgi apparatus and is a major protein convertase in the exocrine pathway, which can recognize specific amino acid sequences, and cleaves and processes the precursors of many important polypeptides and proteins in the secretory pathway to make them biologically active after activated by two times of self-cleavage in the endoplasmic reticulum-Golgi apparatus. It is named because its encoding gene (fur) is located upstream of the proto-oncogene fes/feps. Specifically, furin catalyzes and cleaves the carboxy-terminal peptide bond of Arg-Xaa-Yaa-Arg (Xaa is any amino acid and Yaa is Arg or Lys) in the proprotein to produce a mature protein.

After the fusion polypeptide of the present disclosure is processed with protease, the linking peptide between the A chain and the B chain is removed, so that disulfide bonds are formed between the A chain and the B chain in a manner similar to natural insulin. For example, two disulfide bonds are formed by the sulfhydryl groups in four cysteines, A7 (Cys)-B7(Cys) and A20 (Cys)-B19 (Cys), to link the two chains A and B. In addition, a disulfide bond is also preferably formed by A6 (Cys) and A11 (Cys) inside the A chain. The inventors surprisingly found that even if the A chain or the B chain is linked to the Fc region, it does not affect the formation of correct disulfide bond linking and spatial folding between the A chain and the B chain to form the insulin fused to the Fc region, thereby accomplishing the present disclosure.

Linker

In the fusion protein of the present disclosure, the function of the linker L is to link the A chain or B chain of insulin with the Fc region. The linker L may be a polypeptide or a chemical structure other than a peptide chain.

In some embodiments, the linker is a polypeptide comprising a flexible unit (flexible peptide fragment) consisting essentially of A, T, G and/or S, such as a flexible unit consisting of G and S; the flexible unit may comprise 2-50 or more amino acids in length, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 amino acids.

In other embodiments, the linker is a polypeptide comprising a rigid unit (rigid peptide fragment) consisting essentially of rigid amino acids including but not limited to V, P, I, K, and L.

Characterization of Structure

The insulin-Fc fusion protein is fermented and secreted by CHO cells. After transcription and translation in CHO cells, the fusion protein undergoes a series of processing comprising post-translational modifications such as proline hydroxylation, O-glycosylation, N-glycosylation, deletion of lysine at C-terminal and the like, and such modifications occur on sequences other than the B and A chains of insulin. Besides, the insulin-Fc fusion protein also forms disulfide bonds in the organelles of CHO cells to stabilize its structure.

The disulfide bond of the insulin-Fc fusion protein is formed between two cysteine (Cys) residues. Its disulfide bonds can be divided into two parts according to the position with some in insulin and others in Fc. The disulfide bonds of insulin are located in the B and A chains, and the amino acids of the B and A chains are represented by position (X) in order from the N-terminal to the C-terminal, which are BX and AX, respectively. In some embodiments, the disulfide bonds are CysA7-CysB7, CysA20-CysB19 and CysA6-CysA11. The Fc region consists of two single chains with the same amino acid sequence, and in some embodiments, there are two disulfide bonds in each single chain and two interchain disulfide bonds between the two single chains, meaning that there are 6 disulfide bonds in Fc.

UPLC-QTOF is a conventional instrument for analyzing the structure of biological macromolecules. Its main functional modules are UPLC and QTOF. After being separated by UPLC, the sample to be tested enters the ion source in the state of solution to be ionized and becomes charged ions, which enter the mass analyzer QTOF under the action of an accelerating electric field. Under the action of electric and magnetic fields, the m/z of various ions are captured by two mass spectrometers of triple quadrupole (Q) and time-of-flight mass spectrometry (TOF). The software calculates the precise molecular weight, and finally realizes the structure analysis of complex biological macromolecular proteins. The present disclosure adopts UPLC-QTOF, a commonly used instrument with high resolution and high sensitivity, as an ideal method for analyzing fusion proteins, and mainly analyzes and characterizes the deglycosylation of the fusion protein, its molecular weight after deglycosylation reduction, disulfide bonds and disulfide bond mismatch rate.

The results show that in some embodiments, the insulin-Fc fusion protein has a molecular weight and disulfide bonds consistent with the theory, a low mismatch rate, and post-translational modifications such as proline hydroxylation, O-glycosylation, N-glycosylation, deletion of lysine at C-terminal and the like.

Example 1: Construction of Expression Vector of Insulin Precursor Fusion Protein In this example, the construction method of the insulin precursor fusion protein is mainly described. Herein, the insulin precursor fusion protein is sometimes also referred to as insulin fusion protein and has a molecular form of proINS-L-Fc. It may be secreted and expressed in yeast or eukaryotic cells (such as CHO, HEK293, etc.), and the expressed protein exists in the form of homodimer. In order to assist protein to be secreted and expressed, a signal peptide and/or propeptide can be added to the N-terminal of the protein. The signal peptide includes but is not limited to the sequences shown in Table 1 below.

TABLE 1

| Sequence of signal peptide | |
|---|---|
| Signal peptide name | Sequence |
| NS | MALWMRLLPLLALLALWGPDPAAA (SEQ ID NO: 12) |
| LS | MRSLGALLLLLSACLAVSA (SEQ ID NO: 13) |
| HMM + 38 | MWWRLWWLLLLLLLLWPMVWA (SEQ ID NO: 14) |
| Exendin-4 | MKIILWLCVFGLFLATLFPISWQ (SEQ ID NO: 15) |

proINS refers to a natural insulin precursor or an analog thereof derived from human or otherwise. The analog includes inserted, deleted, truncated or mutated insulin precursors, such as A14E\B16E\B25H\desB30 variant, A14E\B16H\B25H\desB30 variant or A14E\desB30 variant. The analog may reduce the immunogenicity of insulin, or reduce proteolysis to improve the stability of insulin, or reduce the affinity of insulin to insulin receptor (IR) to prolong the in vivo half-life and the like. It can also be used for any other purpose.

The insulin precursor of this example can be processed into mature insulin by proteases such as Kex2, Furin, trypsin and the like. The insulin precursor of this example can also promote the correct folding and processing of the protein through the optimized C-peptide. The analog of the insulin precursor used in this example includes but is not limited to those shown in Table 3 below.

TABLE 3

| Sequence of insulin precursor or analog thereof | | |
|---|---|---|
| Insulin No. | Sequence feature | Sequence |
| proINS-1 | Human insulin precursor | FVNQHLCGSHLVEALYLVCGERGFFYTPKTRREAEDLQVGQVELGGGPGAGSLQPLALEGSLQKRGIVEQCCTSICSLYQLENYCN (SEQ ID NO: 16) |
| proINS-2 | Human insulin precursor, A14E/B16E/B25H | FVNQHLCGSHLVEALELVCGERGFHYTPKTRREAEDLQVGQVELGGGPGAGSLQPLALEGSLQKRGIVEQCCTSICSLEQLENYCN (SEQ ID NO: 17) |
| proINS-3 | Human insulin precursor with modified C-peptide (which can be cleaved by Furin) | FVNQHLCGSHLVEALYLVCGERGFFYTPKTKRIKREAEDLQVGQVELGGGPGAGSLQPLALEGSLQKRIKRGIVEQCCTSICSLYQLENYCN (SEQ ID NO: 18) |
| proINS-4 | Human insulin precursor with modified C-peptide (which can be cleaved by enterokinase) | FVNQHLCGSHLVEALYLVCGERGFFYTPKTDDDDKEAEDLQVGQVELGGGPGAGSLQPLALEGSLQKRDDDDKGIVEQCCTSICSLYQLENYCN (SEQ ID NO: 19) |
| proINS-6 | Human insulin precursor, A14E/B16H/B25H/desB30 | FVNQHLCGSHLVEALHLVCGERGFHYTPKREAEDLQVGQVELGGGPGAGSLQPLALEGSLQKRGIVEQCCTSICSLEQLENYCN (SEQ ID NO: 20) |
| proINS-7 | Human insulin precursor, A14E/B16E/B25H/desB30 | FVNQHLCGSHLVEALELVCGERGFHYTPKREAEDLQVGQVELGGGPGAGSLQPLALEGSLKRGIVEQCCTSICSLEQLENYCN (SEQ ID NO: 21) |
| proINS-8 | Human insulin precursor, A14E/desB30 | FVNQHLCGSHLVEALYLVCGERGFFYTPKREAEDLQVGQVELGGGPGAGSLQPLALEGSLQKRGIVEQCCTSICSLEQLENYCN (SEQ ID NO: 22) |

L represents the linker between proINS and Fc and can consist of amino acids of 0 to any number in length. It can be either a flexible polypeptide or a rigid polypeptide. L can assist the two insulin molecules linked to the Fc homodimer to form correct spatial structures, respectively. Preferably, L has a sequence including but not limited to the sequences shown in Tables 4 and 5.

TABLE 4

| Sequence of flexible linker | |
|---|---|
| L's name | L's sequence |
| GS-$(G_4S)_5$ | GSGGGGSGGGGSGGGGSGGGGSGGGGS (SEQ ID NO: 23) |
| $(G_4S)_5$ | GGGGSGGGGSGGGGSGGGGSGGGGS (SEQ ID NO: 24) |
| $(G_4S)_3$ | GGGGSGGGGSGGGGS (SEQ ID NO: 25) |

TABLE 5

| Sequence of rigid linker | |
|---|---|
| L's name | Sequence |
| GS-CTP | GSGGGGSGGGGSGGGGSGGGGSGGGGSSSSSKAPPPSLPSPSRLPGPSDTPILPQ (SEQ ID NO: 26) |

TABLE 5-continued

| Sequence of rigid linker | |
|---|---|
| L's name | Sequence |
| CA | SASSKAPPPSLPSPSRLPGPSDTPILPQ (SEQ ID NO: 27) |
| CTP | SSSSKAPPPSLPSPSRLPGPSDTPILPQ (SEQ ID NO: 28) |
| 2CTP | SASSKAPPPSLPSPSRLPGPSDTPILPQSSSSKAPPPSLPSPSRLPGPSDTPILPQ (SEQ ID NO: 29) |
| C1 | VAPPPALPAPVRLPGPA (SEQ ID NO: 30) |
| C1C | GGGSVAPPPALPAPVRLPGPASSSSKAPPPSLPSPSRLPGPSDTPILPQ (SEQ ID NO: 31) |
| 2C1 | GGGSVAPPPALPAPVRLPGPAVAPPPALPAPVRLPGPA (SEQ ID NO: 32) |
| C2C | GGGSVAPPPALPAVAPPPALPASSSSKAPPPSLPSPSRLPGPSDTPILPQ (SEQ ID NO: 33) |
| 3C1 | GGAAVAPPPALPAPVRLPGPAVAPPPALPAPVRLPGPAVAPPPALPAPVRLPGPA (SEQ ID NO: 34) |
| 2C1A | GGAAVAPPPALPAPVRLPGPAVAPPPALPAPVRLPGPA (SEQ ID NO: 35) |

Fc is preferably derived from human IgG; more preferably human IgG and variants thereof without ADCC and CDC activities, such as IgG2 and IgG4; more preferably mutated human IgG with prolonged half-life. Fc may also be a fragment of Fc or a fusion of Fc with other proteins/protein fragments. The Fc used in the present disclosure includes but is not limited to the following sequences.

```
Fc1: Human IgG1 Fc
                                        (SEQ ID NO: 36)
EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPG;

Fc2: Human IgG2 Fc, T250Q/P331S/M428L
                                        (SEQ ID NO: 37)
VECPPCPAPPVAGPSVFLFPPKPKDQLMISRTPEVTCVVVDVSHEDPEV

QFNWYVDGVEVHNAKTKPREEQFNSTFRVVSVLTVVHQDWLNGKEYKCK

VSNKGLPASIEKTISKTKGQPREPQVYTLPPSREEMTKNQVSLTCLVKG

FYPSDIAVEWESNGQPENNYKTTPPMLDSDGSFFLYSKLTVDKSRWQQG

NVFSCSVLHEALHNHYTQKSLSLSPGK;

Fc3: Human IgG4 Fc, S228P
                                        (SEQ ID NO: 38)
ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLG;

]Fc4: Human IgG2 Fc, T250Q/N297A/P331S/M428L
                                        (SEQ ID NO: 39)
VECPPCPAPPVAGPSVFLFPPKPKDQLMISRTPEVTCVVVDVSHEDPEV

QFNWYVDGVEVHNAKTKPREEQFASTFRVVSVLTVVHQDWLNGKEYKCK

VSNKGLPASIEKTISKTKGQPREPQVYTLPPSREEMTKNQVSLTCLVKG

FYPSDIAVEWESNGQPENNYKTTPPMLDSDGSFFLYSKLTVDKSRWQQG

NVFSCSVLHEALHNHYTQKSLSLSPGK;

Fc5: Human IgG2 Fc, M252Y/S254T/T256E/N297A
                                        (SEQ ID NO: 40)
VECPPCPAPPVAGPSVFLFPPKPKDTLYITREPEVTCVVVDVSHEDPEV

QFNWYVDGVEVHNAKTKPREEQFASTFRVVSVLTVVHQDWLNGKEYKCK

VSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQG

NVFSCSVMHEALHNHYTQKSLSLSPGK;

Fc6: Human IgG2 Fc, N297A/M428L/N434S
                                        (SEQ ID NO: 41)
VECPPCPAPPVAGPSVFLFPPKPKDTLMISRTPEVTCVVVDVSHEDPEV

QFNWYVDGVEVHNAKTKPREEQFASTFRVVSVLTVVHQDWLNGKEYKCK

VSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQG

NVFSCSVLHEALHSHYTQKSLSLSPGK;
```

-continued

```
Fc7: Human IgG4 Fc, S228P/F234A/L235A
                                        (SEQ ID NO: 42)
ESKYGPPCPPCPAPEAAGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLG;

Fc8: Human IgG4 Fc, S228P/M252Y/S254T/T256E/N297A
                                        (SEQ ID NO: 43)
ESKYGPPCPPCPAPEFLGGPSVFLFPPKPKDTLYITREPEVTCVVVDVS

QEDPEVQFNWYVDGVEVHNAKTKPREEQFASTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLG;

Fc9: Human IgG4 Fc, S228P/N297A/M428L/N434S
                                        (SEQ ID NO: 44)
ESKYGPPCPPCPAPEFLGGPSVFLFPPKPKDTLMISRTPEVTCVVVDVS

QEDPEVQFNWYVDGVEVHNAKTKPREEQFASTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVLHEALHSHYTQKSLSLSLG;

Fc15: Human IgG4 Fc, S228P/F234A/L235A
                                        (SEQ ID NO: 45)
ESKYGPPCPPCPAPEAAGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLG;

Fc16: Human IgG2 Fc
                                        (SEQ ID NO: 46)
VECPPCPAPPVAGPSVFLFPPKPKDTLMISRTPEVTCVVVDVSHEDPEV

QFNWYVDGVEVHNAKTKPREEQFNSTFRVVSVLTVVHQDWLNGKEYKCK

VSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQG

NVFSCSVMHEALHNHYTQKSLSLSPGK.
```

The amino acid sequence features of some insulin precursor fusion proteins constructed in the present disclosure are shown in Table 6.

TABLE 6

Sequence features of insulin precursor fusion protein (proINS-L-Fc)

| Protein name | Insulin precursor (proINS) | Linker (L) | Fc | SEQ ID NO: |
|---|---|---|---|---|
| SS302-001 | proINS-1 | GS-CTP | Fc1 | 47 |
| SS302-002 | proINS-1 | GS-CTP | Fc2 | 48 |
| SS302-003 | proINS-1 | GS-CTP | Fc3 | 49 |
| SS302-004 | proINS-1 | GS-$(G_4S)_5$ | Fc2 | 50 |
| SS302-005 | proINS-1 | $(G_4S)_5$ | Fc4 | 51 |
| SS302-006 | proINS-1 | CA | Fc16 | 52 |
| SS302-007 | proINS-1 | CTP | Fc16 | 53 |

TABLE 6-continued

| Sequence features of insulin precursor fusion protein (proINS-L-Fc) | | | | |
|---|---|---|---|---|
| Protein name | Insulin precursor (proINS) | Linker (L) | Fc | SEQ ID NO: |
| SS302-008 | proINS-1 | 2CTP | Fc16 | 54 |
| SS302-009 | proINS-1 | C1C | Fc16 | 55 |
| SS302-011 | proINS-1 | C2C | Fc16 | 56 |
| SS302-012 | proINS-1 | 2C1 | Fc16 | 57 |
| SS302-013 | proINS-1 | 3C1 | Fc16 | 58 |
| SS302-014 | proINS-1 | 3C1 | Fc5 | 59 |
| SS302-015 | proINS-1 | 3C1 | Fc6 | 60 |
| SS302-016 | proINS-1 | 3C1 | Fc7 | 61 |
| SS302-017 | proINS-1 | 3C1 | Fc8 | 62 |
| SS302-018 | proINS-1 | 3C1 | Fc9 | 63 |
| SS302-019 | proINS-2 | 3C1 | Fc7 | 64 |
| SS302-022 | proINS-3 | 2C1 | Fc16 | 65 |
| SS302-023 | proINS-4 | 2C1 | Fc16 | 66 |
| SS302-029 | proINS-2 | 3C1 | Fc8 | 67 |
| SS302-030 | proINS-2 | 3C1 | Fc9 | 68 |
| SS302-035 | proINS-6 | 2C1A | Fc15 | 69 |
| SS302-036 | proINS-7 | 2C1A | Fc15 | 70 |
| SS302-037 | proINS-8 | 2C1A | Fc15 | 71 |
| SS302-038 | proINS-1 | 2C1A | Fc15 | 72 |

The insulin precursor fusion protein can be converted into a mature insulin fusion protein after processed by proteases such as Kex2, Furin, trypsin, etc. to remove sequences such as C-peptide and the like. In all the examples of the present patent, the protein cleaved and processed by enzyme is named by adding the suffix M (mature) to the name of the precursor protein. For example, after the insulin precursor fusion protein SS302-002 is processed by the protease Kex2, the mature protein is named as SS302-002M. The amino acid sequences of the mature insulin fusion proteins obtained by some insulin precursor fusion proteins of the present disclosure processed by protease are as follows.

```
SS302-001M
]B chain:
                                                  (SEQ ID NO: 73)
FVNQHLCGSHLVEALYLVCGERGFFYTPKTRR;

]A chain-L-Fc1:
                                                  (SEQ ID NO: 74)
GIVEQCCTSICSLYQLENYCNGSGGGGSGGGGSGGGGSGGGGSGGGGSSSSSKAPPPSLP

SPSRLPGPSDTPILPQEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHEALHNHYTQ

KSLSLSPG.

]SS302-002M
]B chain:
                                                  (SEQ ID NO: 75)
FVNQHLCGSHLVEALYLVCGERGFFYTPKTRR;

]A chain-L-Fc2:
                                                  (SEQ ID NO: 76)
GIVEQCCTSICSLYQLENYCNGSGGGGSGGGGSGGGGSGGGGSGGGGSSSSSKAPPPSLP

SPSRLPGPSDTPILPQVECPPCPAPPVAGPSVFLFPPKPKDQLMISRTPEVTCVVVDVSHED

PEVQFNWYVDGVEVHNAKTKPREEQFNSTFRVVSVLTVVHQDWLNGKEYKCKVSNKG

LPASIEKTISKTKGQPREPQVYTLPPSREEMTKNQVSLTCLVKGFYPSDIAVEWESNGQPE

NNYKTTPPMLDSDGSFFLYSKLTVDKSRWQQGNVFSCSVLHEALHNHYTQKSLSLSPGK.
]
SS302-003M
]B chain:
                                                  (SEQ ID NO: 77)
FVNQHLCGSHLVEALYLVCGERGFFYTPKTRR;

]A chain-L-Fc3:
                                                  (SEQ ID NO: 78)
GIVEQCCTSICSLYQLENYCNGSGGGGSGGGGSGGGGSGGGGSGGGGSSSSSKAPPPSLP

SPSRLPGPSDTPILPQESKYGPPCPPCPAPEFLGGPSVFLFPPKPKDTLMISRTPEVTCVVVD

VSQEDPEVQFNWYVDGVEVHNAKTKPREEQFNSTYRVVSVLTVLHQDWLNGKEYKCK
```

-continued

VSNKGLPSSIEKTISKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHEALHNHYTQKSLS

LSLG.

]SS302-004M
]B chain:
(SEQ ID NO: 79)
FVNQHLCGSHLVEALYLVCGERGFFYTPKTRR;

]A chain-L-Fc2:
(SEQ ID NO: 80)
GIVEQCCTSICSLYQLENYCNGSGGGGSGGGGSGGGGSGGGGSGGGGSVECPPCPAPPV

AGPSVFLFPPKPKDQLMISRTPEVTCVVVDVSHEDPEVQFNWYVDGVEVHNAKTKPREE

QFNSTFRVVSVLTVVHQDWLNGKEYKCKVSNKGLPASIEKTISKTKGQPREPQVYTLPPS

REEMTKNQVSLTCLVKGFYPSDIAVEWESNGQPENNYKTTPPMLDSDGSFFLYSKLTVD

KSRWQQGNVFSCSVLHEALHNHYTQKSLSLSPGK.

]SS302-005M
]B chain:
(SEQ ID NO: 81)
FVNQHLCGSHLVEALYLVCGERGFFYTPKTRR;

]A chain-L-Fc4:
(SEQ ID NO: 82)
GIVEQCCTSICSLYQLENYCNGGGGSGGGGSGGGGSGGGGSGGGGSVECPPCPAPPVAG

PSVFLFPPKPKDQLMISRTPEVTCVVVDVSHEDPEVQFNWYVDGVEVHNAKTKPREEQF

ASTFRVVSVLTVVHQDWLNGKEYKCKVSNKGLPASIEKTISKTKGQPREPQVYTLPPSRE

EMTKNQVSLTCLVKGFYPSDIAVEWESNGQPENNYKTTPPMLDSDGSFFLYSKLTVDKSR

WQQGNVFSCSVLHEALHNHYTQKSLSLSPGK.

]SS302-006M
]B chain:
(SEQ ID NO: 83)
FVNQHLCGSHLVEALYLVCGERGFFYTPKTRR;

]A chain-L-Fc16:
(SEQ ID NO: 84)
GIVEQCCTSICSLYQLENYCNSASSKAPPPSLPSPSRLPGPSDTPILPQVECPPCPAPPVAGP

SVFLFPPKPKDTLMISRTPEVTCVVVDVSHEDPEVQFNWYVDGVEVHNAKTKPREEQFN

STFRVVSVLTVVHQDWLNGKEYKCKVSNKGLPAPIEKTISKTKGQPREPQVYTLPPSREE

MTKNQVSLTCLVKGFYPSDIAVEWESNGQPENNYKTTPPMLDSDGSFFLYSKLTVDKSR

WQQGNVFSCSVMHEALHNHYTQKSLSLSPGK.

]SS302-007M
]B chain:
(SEQ ID NO: 85)
FVNQHLCGSHLVEALYLVCGERGFFYTPKTRR;

]A chain-L-Fc16:
(SEQ ID NO: 86)
GIVEQCCTSICSLYQLENYCNSSSSKAPPPSLPSPSRLPGPSDTPILPQVECPPCPAPPVAGPS

VFLFPPKPKDTLMISRTPEVTCVVVDVSHEDPEVQFNWYVDGVEVHNAKTKPREEQFNS

TFRVVSVLTVVHQDWLNGKEYKCKVSNKGLPAPIEKTISKTKGQPREPQVYTLPPSREE

MTKNQVSLTCLVKGFYPSDIAVEWESNGQPENNYKTTPPMLDSDGSFFLYSKLTVDKSR

WQQGNVFSCSVMHEALHNHYTQKSLSLSPGK.

]SS302-008M
]B chain:
(SEQ ID NO: 87)
FVNQHLCGSHLVEALYLVCGERGFFYTPKTRR;

-continued

]A chain-L-Fc16:

(SEQ ID NO: 88)
GIVEQCCTSICSLYQLENYCNSASSKAPPPSLPSPSRLPGPSDTPILPQSSSSKAPPPSLPSPS

RLPGPSDTPILPQVECPPCPAPPVAGPSVFLFPPKPKDTLMISRTPEVTCVVVDVSHEDPEV

QFNWYVDGVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVEWESNGQPENNY

KTTPPMLDSDGSFFLYSKLTVDKSRWQQGNVFSCSVMHEALHNHYTQKSLSLSPGK.

]SS302-009M
]B chain:

(SEQ ID NO: 89)
FVNQHLCGSHLVEALYLVCGERGFFYTPKTRR;

]A chain-L-Fc16:

(SEQ ID NO: 90)
GIVEQCCTSICSLYQLENYCNGGGSVAPPPALPAPVRLPGPASSSSKAPPPSLPSPSRLPGPS

DTPILPQVECPPCPAPPVAGPSVFLFPPKPKDTLMISRTPEVTCVVVDVSHEDPEVQFNWY

VDGVEVHNAKTKPREEQFNSTFRVVSVLTVVHQDWLNGKEYKCKVSNKGLPAPIEKTIS

KTKGQPREPQVYTLPPSREEMTKNQVSLTCLVKGFYPSDIAVEWESNGQPENNYKTTPP

MLDSDGSFFLYSKLTVDKSRWQQGNVFSCSVMHEALHNHYTQKSLSLSPGK.

]SS302-011M
]B chain:

(SEQ ID NO: 91)
FVNQHLCGSHLVEALYLVCGERGFFYTPKTRR;

]A chain-L-Fc16:

(SEQ ID NO: 92)
GIVEQCCTSICSLYQLENYCNGGGSVAPPPALPAVAPPPALPASSSSKAPPPSLPSPSRLPGPS

DTPILPQVECPPCPAPPVAGPSVFLFPPKPKDTLMISRTPEVTCVVVDVSHEDPEVQFNWY

VDGVEVHNAKTKPREEQFNSTFRVVSVLTVVHQDWLNGKEYKCKVSNKGLPAPIEKTIS

KTKGQPREPQVYTLPPSREEMTKNQVSLTCLVKGFYPSDIAVEWESNGQPENNYKTTPP

MLDSDGSFFLYSKLTVDKSRWQQGNVFSCSVMHEALHNHYTQKSLSLSPGK.

]SS302-012M
]B chain:

(SEQ ID NO: 93)
FVNQHLCGSHLVEALYLVCGERGFFYTPKTRR;

]A chain-L-Fc16:

(SEQ ID NO: 94)
GIVEQCCTSICSLYQLENYCNGGGSVAPPPALPAPVRLPGPAVAPPPALPAPVRLPGPAVEC

PPCPAPPVAGPSVFLFPPKPKDTLMISRTPEVTCVVVDVSHEDPEVQFNWYVDGVEVHN

AKTKPREEQFNSTFRVVSVLTVVHQDWLNGKEYKCKVSNKGLPAPIEKTISKTKGQPRE

PQVYTLPPSREEMTKNQVSLTCLVKGFYPSDIAVEWESNGQPENNYKTTPPMLDSDGSFF

LYSKLTVDKSRWQQGNVFSCSVMHEALHNHYTQKSLSLSPGK.
]
SS302-013M
]B chain:

(SEQ ID NO: 95)
FVNQHLCGSHLVEALYLVCGERGFFYTPKTRR;

]A chain-L-Fc16:

(SEQ ID NO: 96)
GIVEQCCTSICSLYQLENYCNGGAAVAPPPALPAPVRLPGPAVAPPPALPAPVRLPGPAVAPP

PALPAPVRLPGPAVECPPCPAPPVAGPSVFLFPPKPKDTLMISRTPEVTCVVVDVSHEDPEV

QFNWYVDGVEVHNAKTKPREEQFNSTFRVVSVLTVVHQDWLNGKEYKCKVSNKGLPA

-continued

PIEKTISKTKGQPREPQVYTLPPSREEMTKNQVSLTCLVKGFYPSDIAVEWESNGQPENNY

KTTPPMLDSDGSFFLYSKLTVDKSRWQQGNVFSCSVMHEALHNHYTQKSLSLSPGK.

]

SS302-014M

]B chain:

(SEQ ID NO: 97)

FVNQHLCGSHLVEALYLVCGERGFFYTPKTRR;

]A chain-L-Fc5:

(SEQ ID NO: 98)

GIVEQCCTSICSLYQLENYCNGGAAVAPPPALPAPVRLPGPAVAPPPALPAPVRLPGPAVAPP

PALPAPVRLPGPAVECPPCPAPPVAGPSVFLFPPKPKDTLYITREPEVTCVVVDVSHEDPEV

QFNWYVDGVEVHNAKTKPREEQFASTFRVVSVLTVVHQDWLNGKEYKCKVSNKGLPA

PIEKTISKTKGQPREPQVYTLPPSREEMTKNQVSLTCLVKGFYPSDIAVEWESNGQPENNY

KTTPPMLDSDGSFFLYSKLTVDKSRWQQGNVFSCSVMHEALHNHYTQKSLSLSPGK.

SS302-015M

B chain:

(SEQ ID NO: 99)

FVNQHLCGSHLVEALYLVCGERGFFYTPKTRR;

A chain-L-Fc6:

(SEQ ID NO: 100)

GIVEQCCTSICSLYQLENYCNGGAAVAPPPALPAPVRLPGPAVAPPPALPAPVRLPGPAVAPP

PALPAPVRLPGPAVECPPCPAPPVAGPSVFLFPPKPKDTLMISRTPEVTCVVVDVSHEDPEV

QFNWYVDGVEVHNAKTKPREEQFASTFRVVSVLTVVHQDWLNGKEYKCKVSNKGLPA

PIEKTISKTKGQPREPQVYTLPPSREEMTKNQVSLTCLVKGFYPSDIAVEWESNGQPENNY

KTTPPMLDSDGSFFLYSKLTVDKSRWQQGNVFSCSVLHEALHSHYTQKSLSLSPGK.

SS302-016M

B chain:

(SEQ ID NO: 101)

FVNQHLCGSHLVEALYLVCGERGFFYTPKTRR;

A chain-L-Fc7:

(SEQ ID NO: 102)

GIVEQCCTSICSLYQLENYCNGGAAVAPPPALPAPVRLPGPAVAPPPALPAPVRLPGPAVAPP

PALPAPVRLPGPAESKYGPPCPPCPAPEAAGGPSVFLFPPKPKDTLMISRTPEVTCVVVDV

SQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESN

GQPENNYKTTPPVLDSDGSFFLYSRLTVDKSRWQEGNVFSCSVMHEALHNHYTQKSLSLSLG.

SS302-017M

B chain:

(SEQ ID NO: 103)

FVNQHLCGSHLVEALYLVCGERGFFYTPKTRR;

A chain-L-Fc8:

(SEQ ID NO: 104)

GIVEQCCTSICSLYQLENYCNGGAAVAPPPALPAPVRLPGPAVAPPPALPAPVRLPGPAVAPP

PALPAPVRLPGPAESKYGPPCPPCPAPEFLGGPSVFLFPPKPKDTLYITREPEVTCVVVDVS

QEDPEVQFNWYVDGVEVHNAKTKPREEQFASTYRVVSVLTVLHQDWLNGKEYKCKVS

NKGLPSSIEKTISKAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALHNHYTQKSLSLSLG.

SS302-018M

B chain:

(SEQ ID NO: 105)

FVNQHLCGSHLVEALYLVCGERGFFYTPKTRR;

-continued

A chain-L-Fc9:

(SEQ ID NO: 106)
GIVEQCCTSICSLYQLENYCNGGAAVAPPPALPAPVRLPGPAVAPPPALPAPVRLPGPAVAPP

PALPAPVRLPGPAESKYGPPCPPCPAPEFLGGPSVFLFPPKPKDTLMISRTPEVTCVVVDVS

QEDPEVQFNWYVDGVEVHNAKTKPREEQFASTYRVVSVLTVLHQDWLNGKEYKCKVS

NKGLPSSIEKTISKAKGQPREPQVYTLPPSQEEMTKNQVSLTCLVKGFYPSDIAVEWESNG

QPENNYKTTPPVLDSDGSFFLYSRLTVDKSRWQEGNVFSCSVLHEALHSHYTQKSLSLSLG.

SS302-019M
B chain:

(SEQ ID NO: 107)
FVNQHLCGSHLVEALELVCGERGFHYTPKTRR;

A chain-L-Fc7:

(SEQ ID NO: 108)
GIVEQCCTSICSLEQLENYCNGGAAVAPPPALPAPVRLPGPAVAPPPALPAPVRLPGPAVAPP

PALPAPVRLPGPAESKYGPPCPPCPAPEAAGGPSVFLFPPKPKDTLMISRTPEVTCVVVDV

SQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESN

GQPENNYKTTPPVLDSDGSFFLYSRLTVDKSRWQEGNVFSCSVMHEALHNHYTQKSLSLSLG.

SS302-022M
B chain:

(SEQ ID NO: 109)
FVNQHLCGSHLVEALYLVCGERGFFYTPKTKRIKR;

A chain-L-Fc16:

(SEQ ID NO: 110)
GIVEQCCTSICSLYQLENYCNGGGSVAPPPALPAPVRLPGPAVAPPPALPAPVRLPGPAVEC

PPCPAPPVAGPSVFLFPPKPKDTLMISRTPEVTCVVVDVSHEDPEVQFNWYVDGVEVHN

AKTKPREEQFNSTFRVVSVLTVVHQDWLNGKEYKCKVSNKGLPAPIEKTISKTKGQPRE

PQVYTLPPSREEMTKNQVSLTCLVKGFYPSDIAVEWESNGQPENNYKTTPPMLDSDGSFF

LYSKLTVDKSRWQQGNVFSCSVMHEALHNHYTQKSLSLSPGK.

SS302-023M
B chain:

(SEQ ID NO: 111)
FVNQHLCGSHLVEALYLVCGERGFFYTPKTDDDDK;

A chain-L-Fc16:

(SEQ ID NO: 112)
GIVEQCCTSICSLYQLENYCNGGGSVAPPPALPAPVRLPGPAVAPPPALPAPVRLPGPAVEC

PPCPAPPVAGPSVFLFPPKPKDTLMISRTPEVTCVVVDVSHEDPEVQFNWYVDGVEVHN

AKTKPREEQFNSTFRVVSVLTVVHQDWLNGKEYKCKVSNKGLPAPIEKTISKTKGQPRE

PQVYTLPPSREEMTKNQVSLTCLVKGFYPSDIAVEWESNGQPENNYKTTPPMLDSDGSFF

LYSKLTVDKSRWQQGNVFSCSVMHEALHNHYTQKSLSLSPGK.

SS302-029M
B chain:

(SEQ ID NO: 113)
FVNQHLCGSHLVEALELVCGERGFHYTPKTRR;

A chain-L-Fc8:

(SEQ ID NO: 114)
GIVEQCCTSICSLEQLENYCNGGAAVAPPPALPAPVRLPGPAVAPPPALPAPVRLPGPAVAPP

PALPAPVRLPGPAESKYGPPCPPCPAPEFLGGPSVFLFPPKPKDTLYITREPEVTCVVVDVS

QEDPEVQFNWYVDGVEVHNAKTKPREEQFASTYRVVSVLTVLHQDWLNGKEYKCKVS

NKGLPSSIEKTISKAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALHNHYTQKSLSLSLG.

SS302-030M

-continued

B chain:

(SEQ ID NO: 115)
FVNQHLCGSHLVEALELVCGERGFHYTPKTRR;

A chain-L-Fc9:

(SEQ ID NO: 116)
GIVEQCCTSICSLEQLENYCNGGAAVAPPPALPAPVRLPGPAVAPPPALPAPVRLPGPAVAPP

PALPAPVRLPGPAESKYGPPCPPCPAPEFLGGPSVFLFPPKPKDTLMISRTPEVTCVVVDVS

QEDPEVQFNWYVDGVEVHNAKTKPREEQFASTYRVVSVLTVLHQDWLNGKEYKCKVS

NKGLPSSIEKTISKAKGQPREPQVYTLPPSQEEMTKNQVSLTCLVKGFYPSDIAVEWESNG

QPENNYKTTPPVLDSDGSFFLYSRLTVDKSRWQEGNVFSCSVLHEALHSHYTQKSLSLSLG.

SS302-035M
B chain:

(SEQ ID NO: 117)
FVNQHLCGSHLVEALHLVCGERGFHYTPKR;

A chain-L-Fc15:

(SEQ ID NO: 118)
GIVEQCCTSICSLEQLENYCNGGAAVAPPPALPAPVRLPGPAVAPPPALPAPVRLPGPAESK

YGPPCPPCPAPEAAGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLG.

SS302-036M
B chain:

(SEQ ID NO: 119)
FVNQHLCGSHLVEALELVCGERGFHYTPKR;

A chain-L-Fc15:

(SEQ ID NO: 120)
GIVEQCCTSICSLEQLENYCNGGAAVAPPPALPAPVRLPGPAVAPPPALPAPVRLPGPAESK

YGPPCPPCPAPEAAGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLG.

SS302-037M
B chain:

(SEQ ID NO: 121)
FVNQHLCGSHLVEALYLVCGERGFFYTPKR;

A chain-L-Fc15:

(SEQ ID NO: 122)
GIVEQCCTSICSLEQLENYCNGGAAVAPPPALPAPVRLPGPAVAPPPALPAPVRLPGPAESK

YGPPCPPCPAPEAAGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLG.

SS302-038M
B chain:

(SEQ ID NO: 123)
FVNQHLCGSHLVEALYLVCGERGFFYTPKTRR;

A chain-L-Fc15:

(SEQ ID NO: 124)
GIVEQCCTSICSLYQLENYCNGGAAVAPPPALPAPVRLPGPAVAPPPALPAPVRLPGPAESK

YGPPCPPCPAPEAAGGPSVFLFPPKPKDTLMISRTPEVTCVVVDVSQEDPEVQFNWYVDG

-continued

```
VEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLG.
```

According to the method described in the "Molecular Cloning: A Laboratory Manual (Third Edition)", the expression vector of insulin precursor fusion protein was constructed.

The sequence of each insulin precursor fusion protein was optimized based on the codon preference of CHO cells.

After gene synthesis of the optimized DNA sequence, it was cloned into a eukaryotic expression vector pFRL3.0 or pTS1 by virtue of HindIII and EcoRI sites. The pFRL3.0 vector comprises the dihydrofolatereductase (DHFR) gene and can achieve high-level protein expression through the co-amplification of DHFR and the target gene. The CHO cells transfected with the vector was screened under MTX to establish a stably expressed cell line. pTS1 is a transient transfection plasmid without screening marker, and can quickly obtain a small amount of insulin precursor fusion protein for early molecular identification. The schematic diagrams of the expression vectors of the insulin precursor fusion protein are shown in FIGS. 1A and 1B.

Example 2: Expression of Insulin Fusion Protein

1. Preparation of Target Protein by Transient Transfection

The plasmids expressing the insulin precursor-Fc fusion protein prepared in Example 1 were transfected into human embryonic kidney cell HEK-293 to transiently express the target protein. HEK-293 cells were thawed and cultured in cell culture shaker flasks for passage culture at a density of $1.0\times10^6$ cells/mL with a culture medium of OPM-293 CD05 Medium (Shanghai OPM Biosciences Co., Ltd.) under the culture conditions of 37° C., 120 rpm and $CO_2$. The cells were passaged every two days, and could be used for transient transfection after one week of culture. The cell density was adjusted before transfection to make the cell density of about $4.0\times10^6$ cells/ml on the day of transfection. The plasmid was transiently transfected into HEK-293 cells using the FectoPRO kit (Polyplus Transfection), with a ratio of DNA to FectoPRO® Reagent of 1:1 (μg/μL), that is, 1 g of DNA transfected per milliliter of cells corresponding to 1 μL of FectoPRO® Reagent. The plasmid was diluted with Opti-MEM (Gibco) at room temperature in an amount of 10% of the total volume of the transient transfection system, and mixed well by shaking. The diluted plasmid was added to the centrifuge tube of FectoPRO® Reagent at one time, mixed well immediately, and incubated at room temperature for 10 min. The prepared plasmid and transfection reagent mixture were added to the density-adjusted HEK-293 cell suspension at one time and mixed well. Then the cell culture shaker flask was placed in an incubator under the culture conditions of 37° C., 5% $CO_2$, and a shaker speed of 120 rpm. After the cells were transfected and cultured for 4 hours, Volume of FectoPRO® Booster was added at 0.5 μL per milliliter of cells. After 24 hours of culture, the culture conditions were changed to 31° C., 5% $CO_2$ and 120 rpm for fermentation. After 3-5 days of culture, when the cell viability was less than 90%, the supernatant was harvested by centrifugation (3000 rpm), detected for expression level, and then purified to obtain the target protein.

2. Transfection of Stably Expressing Cell Lines and Selection of High Expressing Cell Lines The plasmids partially expressing the insulin precursor-Fc fusion protein prepared in Example 1 were transfected into Chinese hamster ovary cells (CHO DG44) (Invitrogen) to construct stably expressing cell lines, from which high-yielding cell lines were selected for fed-batch culture to prepare the target protein.

The host cell DG44 was thawed and cultured with complete medium containing CDM1N (Shanghai OPM Biosciences Co., Ltd.) plus 1% HT (Invitrogen) under the culture conditions of 37° C., 5% $CO_2$, and a shaker speed of 120 rpm. A certain amount of cell suspension was taken up aseptically with a pipette every day for counting. When the cell density reached $3\times10^6$-$4\times10^6$ cells/mL, cells were passaged, and the initial density of the passaged cell was maintained at about $1\times10^6$ cells/mL. When the total amount of cells met the transfection requirements, cells were harvested for electroporation. The host cells (CHO DG44) were transfected by electroporation using a Bio-Rad electroporator. A 4 mm electroporation cup was used for electroporation, and the specific electroporation parameters were as follows: voltage of 290V, pulse length of 20 milliseconds, and the number of electroporation of 1 time. $1\times10^7$ cells were subjected to electroporation at a time, and 40 g of plasmid was used at a total volume of 0.8 mL. After electroporation, cells were transferred into 15 mL of recovery medium (CDM1N+1% HT), and cultured statically in a cell culture dish for 48 hours. After 48 hours, cells were centrifuged, resuspended in screening medium (CDM1N+100 nM MTX), and diluted to about $1\times10^4$ cells/mL. Then the diluted cells were inoculated in a 96-well plate at 100 μL/well, and placed in an incubator for static culture at 37° C. and 5% $CO_2$. After 5 days of culture, cells were supplemented with 50 μL of the screening medium. When the clone confluence rate reached 80% or more, the expression level was analyzed by dot blotting, in which the antibody was HRP-labeled goat anti-human IgG antibody. The clones with high expression level were screened out, transferred from 96-well plates to 24-well plates for continuous culture, and supplemented with 1 mL of the screening medium. The screening and amplification of high-yielding clones in 12-well plates and 10 cm cell culture dishes were carried out using the same method.

To increase the yield of the fusion protein, cells were cultured with increasing MTX concentrations. The co-amplification of DHFR gene and the fusion protein gene was achieved through the inhibition of DHFR gene by MTX. In the screening process, methods known to those of ordinary skill in the art were used. For example, the details can be referred to: 1. Yang Wei, Wang Di, Chen Keqing, et al. Selection of electroporation transfection conditions of plasmid [J]. Journal of Huazhong University of Science and Technology, 2009, 38 (6): 858-860.; 2. Gu Xin, Li Yan. Discussion on the method of electroporation of mammalian cells DG44-CHO [J]. Biotechnology Letters, 2008, 19(1): 87; 3. Jun, Kim, Baik, Hwang, Lee: Selection strategies for the establishment of recombinant Chinese hamster ovary cell line with dihydrofolate reductase-mediated gene amplification. Appl Microbiol Biotechnol. 2005, 69 (2): 162-169. 10.1007/s00253-005-1972-8.

After screening the clone pool in the 10 cm cell culture dish, the high-yielding clones were transferred to cell culture shaker flasks for culture at 37° C., 5% $CO_2$ and a shaker speed of 120 rpm. After the high-yielding cell clones grew to a certain number, a part of the cells were collected for cryopreservation, and the remaining cells were subjected to fed-batch culture, during which cells were inoculated at a density of $1\times10^6$ cells/ml and placed in cell culture shaker flasks for culture at 37° C., 5% $CO_2$ and a shaker speed of 120 rpm. After inoculation, cells were taken every day for counting to record the cell density and viability. Feeding was started from the 3rd day of culture, once a day. On the 3rd to 8th day, the feeding amount was 2%, 3%, 4%, 3%, 3% and 3% of the initial volume, respectively, and from the 9th day, the feeding amount was 2%, with the total feeding ratio of 20%~30%. Glucose was supplemented once a day to maintain the glucose concentration in the culture system at 3-4 g/L. The culture period was 12-14 days. After the culture, the supernatant was harvested by centrifugation (3000 rpm), detected for expression level, and then purified to obtain the target protein.

Example 3: Purification of Insulin-Fc Fusion Protein

1. Capture of Insulin Precursor-Fc Fusion Protein

Each insulin precursor-Fc fusion protein (SS302-002, SS302-004, SS302-005, SS302-008, SS302-012, SS302-014, SS302-015, SS302-019, SS302-029, SS302-030 and SS302-035) expressed in Example 2 of the cell fermentation solution was captured by affinity chromatography after removing cell debris by centrifugation and filtration through a 0.22 m filter membrane. Bestchrom's protein A was used as an affinity medium. The protein A chromatography column was equilibrated using 3-5 times the column volume of buffer (20 mM $Na_2HPO_4$-citric acid, pH 7.5) to elute to a stable baseline, and then the treated supernatant of the fermentation solution was loaded on the column (loading capacity of 3-8 g/L). After the loading was completed, the impurity protein was washed to the baseline with washing buffer (20 mM Tris, 1.5 M NaCl, 2 M Urea, pH 7.5), and finally the column was eluted using elution buffer of 20 mM $Na_2HPO_4$-citric acid and 0.4M Arg with pH 3.5. The samples were collected separately according to the reading of the UV detector, starting from when the absorption value at UV280 nm was higher than 0.15 AU and stopping lower than 0.20 AU again. The collected samples were immediately added with 2.0 mol/L Tris-HCl buffer and stirred slowly to adjust the pH of the samples to 6.5-7.0. Then the samples were stored at −80° C. for subsequent SDS-PAGE analysis (FIG. 2) and structural identification (see Example 4).

Figure 2:
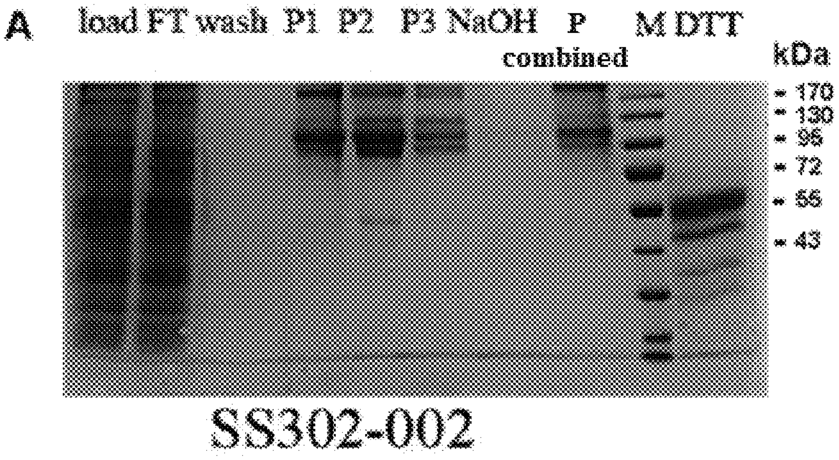
FIG. 2 shows the SDS-PAGE electrophoretogram of the insulin-Fc fusion protein captured in Example 3; M represents marker, different Ps represent the target proteins collected separately during chromatography, and P+DTT represents the target band after protein reduction. The marker size is marked on the side of the SDS electrophoretogram of molecule SS302-002, and the markers used in other electrophoretogram are the same.
Figure 2:
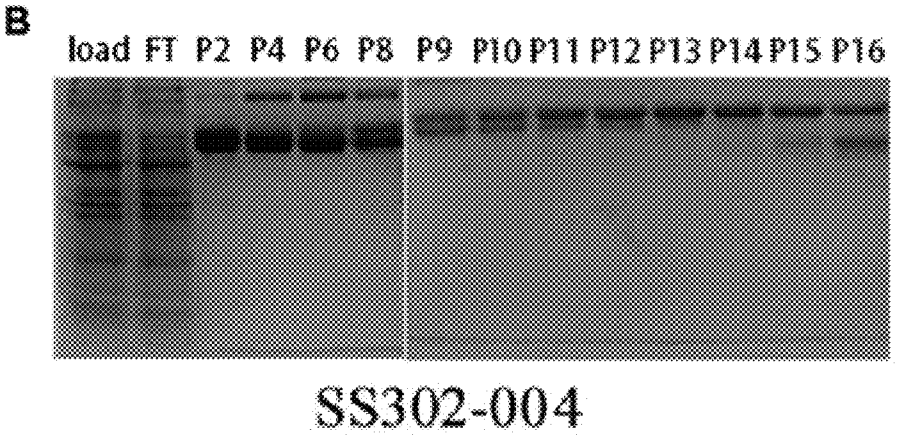
Figure 2:
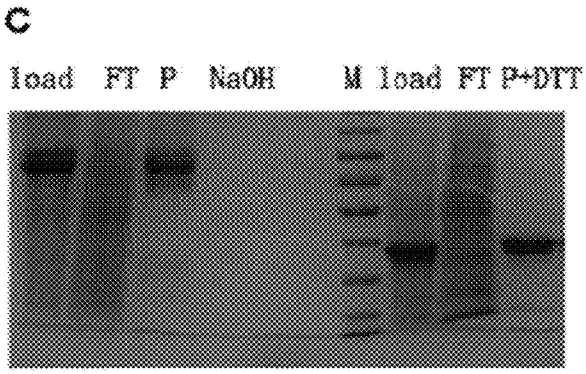
Figure 2:
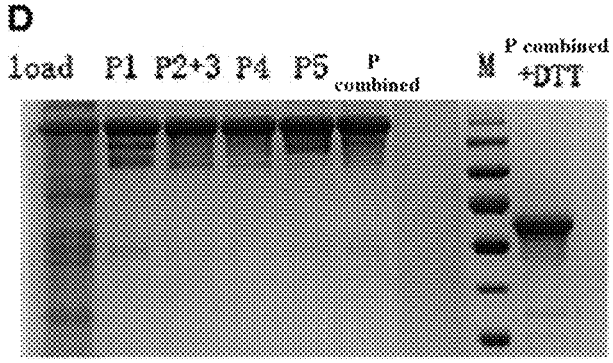
Figure 2:
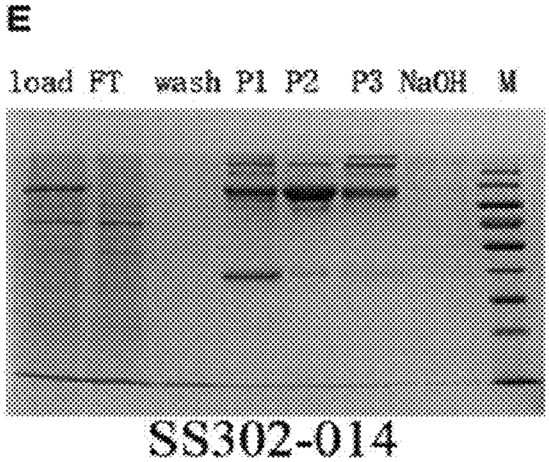
Figure 2:
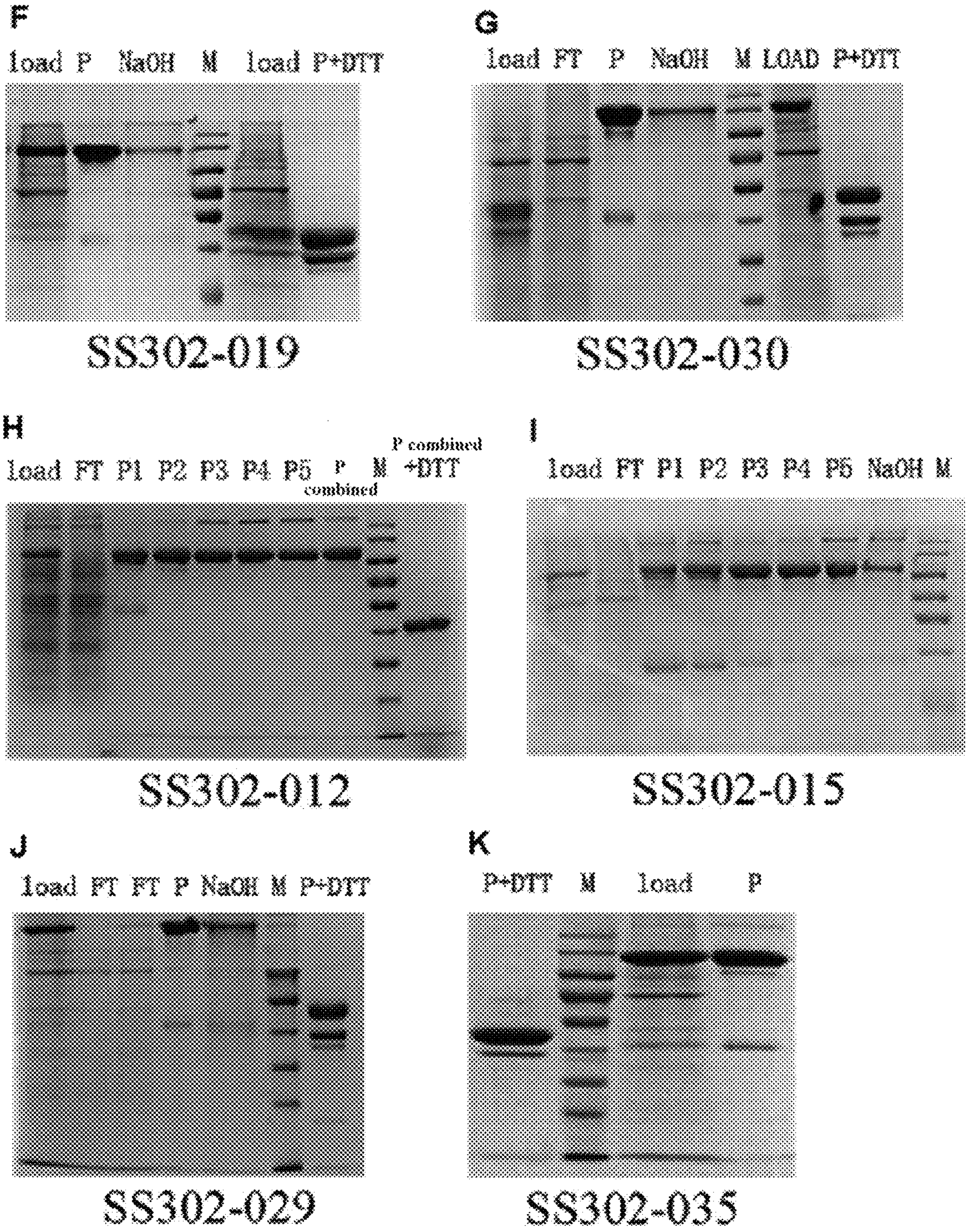

The SDS-PAGE results are shown in FIG. 2, where "load" represents the loaded sample for chromatography, "FT" represents the flow through sample, "wash" represents the elution sample, P1, P2, P3, etc. represent the target proteins collected separately during chromatography, "P combined" represents the separately collected samples which were combined according to the volume ratio of the collection volume, NaOH represents the sample collected by column washing, DTT represents the target protein after reduction, M represents the marker of molecular weight; A: SS302-002, B: SS302-004, C: SS302-005, D: SS302-008, E: SS302-014, F: SS302-019, G: SS302-030, H: SS302-012, I: SS302-015, J: SS302-029, and K: SS302-035. As can be seen from FIG. 2, the SS302-002 protein had an obvious upper band (about 130 KD), a lower band (between 95-130 KD), and a high molecular weight form (>170 KD). The yield of the upper band (130 KD) with a purity greater than 90% was about 60%. The SS302-004 protein had an obvious upper band (95-130 KD) and a lower band (about 95 KD), of which the lower band P1-4 combined sample and the upper band P13-15 combined sample were subjected to structural identification by mass spectrometry (Example 4). This molecule was mostly the lower band of 95 KD in the captured protein, and the upper band of 95-130 KD with a purity greater than 90% had a low yield (about 15%) in the captured protein. The SS302-005 protein was between 72-95 KD, with wide and diffuse electrophoresis band. The common feature of these molecules was that they all comprised GS flexible linker, while other molecules such as SS302-008, SS302-012, SS302-015, etc., were basically a single band, and their common feature was that they comprised a rigid linker such as CTP, C1, etc. The identification results of mass spectrometry (see Example 4) further showed that the insulin precursor-Fc fusion protein comprising a flexible linker (such as GS) had a certain mismatch rate of disulfide bonds and a low recovery rate of correct bands. However, compared with the insulin precursor-Fc fusion protein comprising a flexible linker (such as GS), the insulin precursor-Fc fusion protein comprising a rigid linker had a lower mismatch rate of disulfide bonds, and a higher content of the correctly folded insulin precursor protein in the obtained protein.

2. Cleavage of Insulin Precursor-Fc Fusion Protein by Protease

The protein captured in step 1 was subjected to buffer exchange with G25 using a buffer of 50 mM Tris, 150 mM NaCl, pH 8.0. After the buffer exchange, each protein was cleaved with Kex2 to remove the C-peptide to obtain insulin-Fc fusion proteins. The cleavage conditions of SS302-002 and SS302-004 were as follows: the final protein concentration of 1 mg/mL, the feeding ratio (mass ratio) of 200:1 (precursor: Kex2), the final concentration of $CaCl_2$ of 20 mM/L, and the total reaction volumes of 5 mL and 3 mL, respectively, and the cleavage was performed in a water bath at 37° C. for 6 h. The cleavage conditions of the three proteins SS302-008 and SS302-012 were as follows: the final protein concentration of 1 mg/mL, the feeding ratio (mass ratio) of 50:1 (precursor: Kex2), the final concentration of $CaCl_2$ of 20 mM/L, and the total reaction volume of 190 mL, and the cleavage was performed in a water bath at 37° C. for 6 h. The cleavage conditions of SS302-014, SS302-015, SS302-019, SS302-029, SS302-030 and SS302-035 were as follows: the final protein concentration of 1 mg/mL, the feeding ratio (mass ratio) of 1:25 (Kex2: precursor), the final concentration of $CaCl_2$ of 20 mM/L, and the total reaction volume of 60-180 mL (varying slightly for different proteins), and the cleavage was performed in a water bath at 37° C. for 6 h. The insulin-Fc fusion proteins after cleavage of each insulin precursor-Fc fusion by protease were named as S302-002M, SS302-004M, SS302-005M, SS302-008M, SS302-012M, SS302-014M, SS302-015M, SS302-019M, SS302-029M, SS302-030M and SS302-035M.

3. Purification of Cleaved Insulin-Fc Fusion Protein

In order to remove protease and impurities after the reaction and obtain the correctly folded insulin-Fc fusion protein with high purity, cleaved SS302-004M and SS302-005M were filtered with 10 KD ultrafiltration tube to remove protease and other impurities, so as to obtain the insulin-Fc fusion protein with high purity. Cleaved SS302-008M, SS302-012M, SS302-014M, SS302-015M, SS302-029M and SS302-030M were subjected to hydrophobic chromatography to remove impurities. The medium for hydrophobic chromatography, Butyl HP (Bestchrom), was equilibrated using 3-5 column volume of buffer of 20 mM Tris, 1M $(NH_4)_2SO_4$, pH 7.5. After the equilibration was completed, the sample was loaded (loading capacity of 3-8 g/L). After the loading was completed, the linear gradient elution was performed with a buffer of 20 mM Tris, pH 7.5 (0-100%, 20 column volume). The samples were collected separately according to the reading of the UV detector and detected. The impurities of cleaved SS302-019M and SS302-035M were removed in two steps. The first step was anion chromatography. The medium for anion chromatography, Q HP (Bestchrom), was equilibrated using 3-5 column volume of buffer of 20 mM Tris, pH 8.5. After the equilibration was completed, the sample was loaded (loading capacity of 5 g/L). After the loading was completed, the linear gradient elution was performed with a buffer of 20 mM Tris, 0.5M NaCl, pH 8.5 at a flow rate of 3 ml/min (0-60% B, 15 CV). The samples were collected separately according to the reading of the UV detector (by the same method as above) and detected. The samples with high purity were combined for hydrophobic chromatography of the next step. The medium for hydrophobic chromatography, Butyl HP (Bestchrom), was equilibrated using 3-5 column volume of buffer of 20 mM Tris, 1M NaCl, pH 8.0. After the equilibration was completed, the sample was loaded with a loading capacity of 3-8 g/L. After the loading was completed, the linear gradient elution was performed with a buffer of 20 mM Tris, pH 8.0 at a flow rate of 1 ml/min (0-100% B, 15 CV). The samples were collected separately according to the reading of the UV detector (by the same method as above) and detected for structural analysis, in which the molecular weight and disulfide bonds were characterized by UPLC-QTOF, see Example 4 for details.

Example 4: Structural Analysis of Fusion Protein

Figure 3:
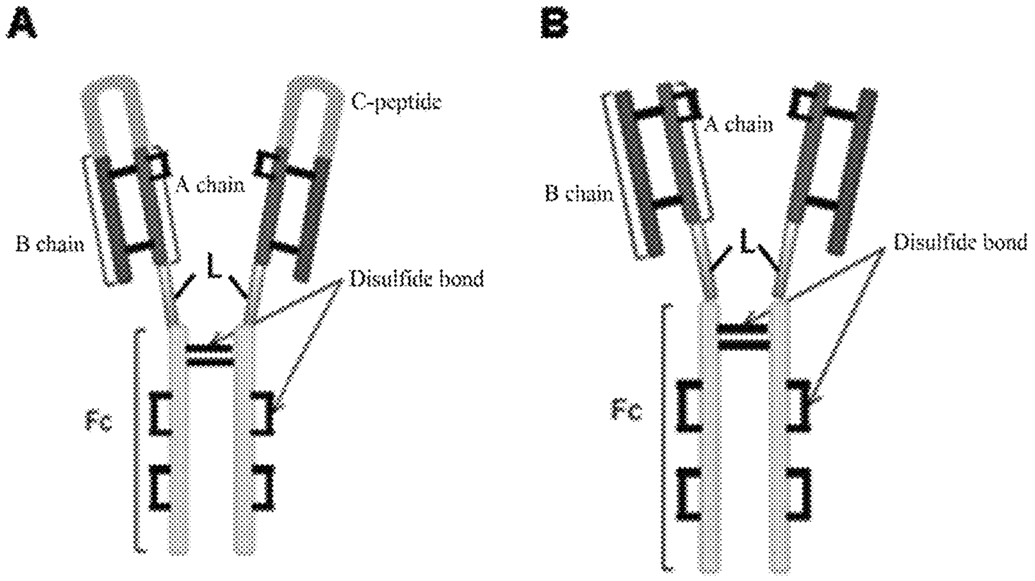
FIG. 3 shows the schematic diagram of the structure of the insulin-Fc fusion protein of the present disclosure before (3A) and after (3B) being cleaved by protease.

The insulin fusion protein precursor has a structure of proINS-L-Fc, with proINS being a human insulin precursor (comprising B—C-A) and L a linker, and its schematic diagram is shown in FIG. 3A. The proteolysis of the insulin fusion protein precursor produces a mature protein with a structure of insulin (B-A)-L-Fc, and its schematic diagram is shown in FIG. 3B. The linker used in the insulin fusion protein is a flexible linker (such as GS) or a rigid linker (such as CTP or C1). During the fermentation in CHO cells, the S and T on the propeptide and rigid linker (such as CTP or C1) may undergo O-glycosylation and P on the linker C1 may undergo proline hydroxylation, while the flexible linker such as GS hardly undergoes post-translational modifications. For structural analysis, the molecular weight and disulfide bonds were characterized by UPLC-QTOF. The insulin-Fc fusion protein (containing glycosylation modification) was subjected to deglycosylation and reduction to obtain an aglycosylated molecule that is easy to be analyzed. SS302-002 (about 130 KD), SS302-002 (between 95-130 KD), SS302-008, SS302-008M, SS302-012, SS302-012M, SS302-014, SS302-014M, SS302-015, SS302-015M, SS302-019, SS302-019M, SS302-029, SS302-029M, SS302-030, SS302-030M, SS302-035 and SS302-035M were detected for both their complete and reduced molecular weight after deglycosylation, and SS302-004 (between 95-130 KD), SS302-004 (about 95 KD) and SS302-005 were detected for both their complete and reduced molecular weight. The results indicated that the insulin-Fc fusion proteins had a molecular weight consistent with the theory.

The spatial structure of the insulin-Fc fusion protein was supported and stabilized by the disulfide bonds formed between the sulfhydryl groups of two Cys residues. The disulfide bonds are divided into two parts, with some in insulin and others in Fc. The disulfide bonds of insulin are located in the B and A chains, and the amino acids of the B and A chains are respectively named by BX and AX in order from the N-terminal to the C-terminal, wherein X is the position of the amino acid in the sequence, and the disulfide bonds are CysA7-CysB7, CysA20-CysB19, and CysA6-CysA11. Fc consists of two polypeptide chains with the same sequence, and there are two disulfide bonds in each polypeptide chain, i.e., four disulfide bonds in two polypeptide chains, and two interchain disulfide bonds between the two polypeptide chains, meaning that there are 6 disulfide bonds in Fc. Theoretically, the disulfide bonds of the insulin-Fc fusion protein is not affected by the kex2 proteolysis. The structural analysis of the disulfide bonds of the insulin-Fc fusion protein was accomplished by buffer exchange of non-reducing denaturation, cleavage by restriction enzyme and analysis by the software UNIFI. There were two pretreatment methods. When analyzed by UNIFI, the two chains of the insulin-Fc fusion protein precursor were named as chain 1 and chain 2, respectively, of which the peptide fragments formed through proteolysis by Glu-C in pretreatment method 1 were named as 1:VN and 2:VN by UNIFI (see Tables 8-11), and the peptide fragments formed through proteolysis by Glu-C and trypsin in pretreatment method 2 were named as 1:VTN and 2:VTN by UNIFI (see Table 15); the two B chains of the mature insulin-Fc fusion protein were named as chain 1 and chain 3, and the two A+Fc chains were named as chain 2 and chain 4, respectively, of which the peptide fragments formed through proteolysis by Glu-C and trypsin in pretreatment method 2 were named as 1:VTN, 2:VTN, 3:VTN and 4:VTN by UNIFI (see Tables 12-14 and 16), where N represents the software number of the peptide fragment after proteolysis, which was sequentially numbered as 1, 2, 3, . . . and so on from the N-terminal to the C-terminal. Moreover, the disulfide bond in UNIFI was represented by "=", the interchain disulfide bond was located between the two peptide fragments, and the intrachain disulfide bond was located on the right side of the peptide fragment.

SS302-002 (about 130 KD), SS302-002 (between 95-130 KD), SS302-004 (between 95-130 KD), SS302-004 (about 95 KD) and SS302-005 were treated by the pretreatment method 1 to analyze their disulfide bonds. The steps of the pretreatment method 1 are as follows. The sample of protein SS302 was placed into a 0.5 mL 10 kD ultrafiltration tube and concentrated to 5 mg/mL under a condition of 4° C. and 12000 rpm. 30 μL of the concentrated sample was added with 18 μL of 8M guanidine hydrochloride (pH7.5) and 0.48 μL of 1M IAA (iodoacetamide), mixed well by vortex, and incubated at room temperature in the dark for 40 min. 1.8 μL of the above sample was diluted with 23 μL of 50 mM Tris-HCl (pH8) buffer, added with 2.25 μL of 0.1 mg/mL Glu-C at a ratio of protein:enzyme=25:1 (μg:μg), water-bathed at 37° C. overnight, and added with 3 μL of 10% FA (formic acid) the next day to stop the reaction for UPLC-QTOF detection. Due to the incomplete denaturation by the pretreatment method 1, the linker region was difficult to be enzymatically cleaved, so that the disulfide bonds on the insulin and the disulfide bonds in the hinge region were linked together by the linking peptide. The large molecular weight makes matching difficult, so this method results in the loss of key disulfide bond information and was mainly used to compare the difference in disulfide bond mismatches between the two bands SS302-002 (about 130 KD) and SS302-002 (between 95-130 KD), and between the two bands SS302-004 (between 95-130 KD) and SS302-004 (about 95 KD).

SS302-008, SS302-012, SS302-012M, SS302-014, SS302-014M, SS302-015, SS302-015M, SS302-019M, SS302-029M, SS302-030M, SS302-035 and SS302-035M were treated by the pretreatment method 2 to analyze their disulfide bonds. The steps of the pretreatment method 2 are as follows. 40 μL of the sample of protein SS302 was added with 120 L of 8M guanidine hydrochloride, water-bathed at 60° C. for 1 h, cooled to room temperature, added with 3.2 μL of 1M IAA, incubated at room temperature in the dark for 45 min, and subjected to buffer exchange for 3 times into 50 mM Tris-HCl buffer (pH 8) using an 0.5 mL 10 kD ultra-filtration tube under a condition of 12000 rpm and 4° C., so that the sample concentration after the buffer exchange was about 0.62 mg/mL. 40 μL of the above sample was added with 2 L of Glu-C (0.5 mg/mL) and 2 μL of trypsin (0.5 mg/mL) at a ratio of protein:enzyme=25:1 (μg:μg), water-bathed at 37° C. overnight, and added with 5 μL of 10% FA the next day to stop the reaction for UPLC-QTOF detection. In the pretreatment method 2, trypsin and Glu-C were used together for enzymatic cleavage to realize the enzymatic cleavage of the linker region and the correct matching of disulfide bonds in the above SS302 molecules, and this method obtains more realistic calculation results of mismatched disulfide bonds.

The detection results of disulfide bonds obtained by UPLC-QTOF were analyzed combined with UNIFI software to analyze the correct disulfide bonds and mismatched disulfide bonds, and the disulfide bond mismatch is reflected by the total mismatch rate and insulin mismatch rate, where the total mismatch rate is the ratio of the total XIC peak area of the mismatched disulfide bond peptides to the total XIC peak area of all disulfide bond peptides, and the insulin mismatch rate is the ratio of the total XIC peak area of the mismatched disulfide bonds in the insulin moiety to the total XIC peak area of all disulfide bond peptides. The mismatch rates of SS302-002, SS302-004, SS302-005, SS302-008, SS302-012, SS302-012M, SS302-014, SS302-014M, SS302-015, SS302-015M, SS302-019M, SS302-029M, SS302-030M, SS302-035, and SS302-035M are shown in Table 7.

For fusion proteins comprising a flexible linker (SS302-004 and SS302-005), SS302-005 had the highest mismatch rate among all molecules, and the target band of SS302-004 (between 95-130 KD) had a relatively low mismatch rate, but a not high yield due to the fact that it was not easily separated from the components with high mismatch rate. For fusion proteins comprising both flexible and rigid moieties in the linker (SS302-002), the target band had a comparable total mismatch rate and insulin mismatch rate to fusion proteins comprising a flexible linker (SS302-004), both of which had components with high total mismatch rate and insulin mismatch rate and are not easily purified and separated. However, the precursor proteins and mature proteins comprising a rigid linker (SS302-008, SS302-012, SS302-012M, SS302-014, SS302-014M, SS302-015, SS302-015M, SS302-019M, SS302-029M, SS302-030M, SS302-035, SS302-035M) had a total mismatch rate and insulin mismatch rate of less than 8%. The disulfide bond results of SS302-002, SS302-004, SS302-012M, SS302-019M, SS302-030M, SS302-035 and SS302-035M in Example 4 are described in detail, and the results are shown in Tables 8-16.

In conclusion, a rigid linker had a great positive effect on the accuracy of the structural expression of the insulin fusion protein in CHO cells, and the stronger the rigidity, the higher the accuracy of its molecular structural expression.

TABLE 7

Mismatch rate of disulfide bonds in fusion proteins

| Molecule No. | Insulin mismatch rate | Total mismatch rate |
| --- | --- | --- |
| SS302-002[b] | Band of about 130 KD (target band, with a yield of the component with a purity greater than 90% of about 60%): 9% (detection result of the recovered protein)<br>Band between 95-130 KD: 29% | Band of about 130 KD (target band, with a yield of the component with a purity greater than 90% of about 60%): 9% (detection result of the recovered protein)<br>Band between 95-130 KD: 29% |
| SS302-004[a] | Band between 95-130 KD (target band, with a yield of the component with a purity greater than 90% of about 15%): 4%<br>Band of about 95 KD: 37% | Band between 95-130 KD (with a yield of the component with a purity greater than 90% of about 15%): 4%<br>Band of about 95 KD: 37% |
| SS302-005[a] | 69% | 69% |
| SS302-008[b] | 6.2% | 6.2% |
| SS302-012[b] | 5.6% | 7.5% |
| SS302-012M[b] | 2.2% | 2.9% |
| SS302-014[b] | 2.4% | 4.8% |
| SS302-014M[b] | 0.8% | 2.8% |
| SS302-015[b] | 1.8% | 4.5% |
| SS302-015M[b] | 1.2% | 3.6% |
| SS302-019M[b] | 1.2% | 2.8% |
| SS302-029M[b] | 0% | 1.1% |

TABLE 7-continued

| Mismatch rate of disulfide bonds in fusion proteins | | |
|---|---|---|
| Molecule No. | Insulin mismatch rate | Total mismatch rate |
| SS302-030M[b] | 0% | 1.7% |
| SS302-035[b] | 2.2% | 4.3% |
| SS302-035M[b] | 2.0% | 2.5% |

Note:
[a]represents that the fusion protein contains a flexible linker, and [b]represents that the fusion protein contains a rigid linker;
the total mismatch rate is the ratio of the total XIC peak area of the mismatched disulfide bond peptides to the total XIC peak area of all disulfide bond peptides; and
the insulin mismatch rate is the ratio of the total XIC peak area of the mismatched disulfide bonds in the insulin moiety to the total XIC peak area of all disulfide bond peptides.
1. SS302-002

Combined with SDS-PAGE technology, this molecule can be purified to obtain a band of about 130 KD and a band between 95-130 KD. The two bands were subjected to disulfide bond identification respectively to estimate the total mismatch rate and insulin mismatch rate of disulfide bonds. The results showed that total mismatch rate and insulin mismatch rate were both 900 for the band of about 130 KD, and the total mismatch rate and insulin mismatch rate were both 29% for the band between 95-130 KD. The results of the disulfide bonds of the band of about 130 KD are shown in Table 8, and the results of the disulfide bonds of the band between 95-130 KD are shown in Table 9. The mismatched disulfide bonds were mainly presented as the self-linking of the B chain of insulin and the mismatch between the two B chains of insulin.

TABLE 8

Detection results of disulfide bonds of ~130 KD band of insulin precursor-Fc fusion protein (SS302-002)

| Peptide fragment | Peak time (min) | Measured molecular weight (Da) | Error (ppm) | Sequence | XIC peak area | Measured m/z | Charge number |
|---|---|---|---|---|---|---|---|
| 1: V1-1: V8 | 43.23 | 2968.3103 | 0.2 | FVNQHLCGSHLVE = QCC TSICSLYQLE = | 1186566144 | 990.1083 | 3 |
| 1: V11-12-1: V17 | 32.63 | 3161.5521 | 0.9 | VTCVVVDVSHEDPE = YK CKVSNKGLPASIE | 674588864 | 791.1435 | 4 |
| 1: V20-1: V23 | 57.43 | 7379.5855 | 0.3 | MTKNQVSLTCLVKGFYP SDIAVE = NNYKTTPPMLD SDGSFFLYSKLTVDKSRW QQGNVFSCSVLHE | 22043154 | 1055.0899 | 7 |
| 1: V2-2: V2 | 52.36 | 1731.8312 | / | ALYLVCGE = ALYLVCGE | 20559026 | 866.4193 | 2 |
| 1: V1-1: V2 | 40.7 | 2347.1204 | / | FVNQHLCGSHLVE = ALYLVCGE | 73175656 | 783.0450 | 3 |
| 1: V2-1: V8 | 53.21 | 2353.0198 | / | ALYLVCGE = QCCTSICSLYQLE = | 54944492 | 1177.0136 | 2 |
| 1: V1-2: V1 | 32.96 | 2962.4083 | / | FVNQHLCGSHLVE = FVNQHLCGSHLVE | 36753932 | 741.3575 | 4 |
| 1: V8-2: V8 | 56.91 | 2974.2084 | / | QCCTSICSLYQLE = QCCTSICSLYQLE = | 7446664 | 992.0743 | 3 |

Note:
The underline represents the fragment where the mismatched disulfide bond is located.

TABLE 9

Detection results of disulfide bonds of 95-130 KD band of insulin precursor-Fc fusion protein (SS302-002)

| Peptide fragment | Peak time (min) | Measured molecular weight (Da) | Error (ppm) | Sequence | XIC peak area | Measured m/z | Charge number |
|---|---|---|---|---|---|---|---|
| 1:V1-1:V8 | 43.35 | 2968.3100 | 0.1 | FVNQHLCGSHLVE=QCCTSICSLYQLE= | 32977026 | 990.1082 | 3 |
| 1:V11-12-1:V17 | 32.71 | 3161.5537 | 1.4 | VTCVVVDVSHEDPE=YKCKVSNKGLPASIE | 673510272 | 791.1439 | 4 |
| 1:V20-1:V23 | 57.4 | 7379.5832 | −0.1 | MTKNQVSLTCLVKGFYPSDIAVE=NNYKTTPPMLDSDGSFFLYSKLTVDKSRWQQGNVFSCSVLHE | 22070320 | 1055.0896 | 7 |
| 1:V2-2:V2 | 52.33 | 1731.8324 | / | ALYLVCGE=ALYLVCGE | 23511048 | 866.4198 | 2 |
| 1:V1-1:V2 | 40.64 | 2347.1204 | / | FVNQHLCGSHLVE=ALYLVCGE | 208205216 | 783.0450 | 3 |
| 1:V2-1:V8 | 53.18 | 2353.0183 | / | ALYLVCGE=QCCTSICSLYQLE= | 10071084 | 1177.0128 | 2 |
| 1:V1-2:V1 | 33.03 | 2962.4118 | / | FVNQHLCGSHLVE=FVNQHLCGSHLVE | 48102752 | 741.3584 | 4 |
| 1:V8-2:V8 | 55.79 | 2974.2116 | / | QCCTSICSLYQLE=QCCTSICSLYQLE= | 7483038 | 992.0754 | 3 |

Note:
The underline represents the fragment where the mismatched disulfide bond is located.
2. SS302-004

This molecule was purified to obtain a band between 95-130 KD (P1-4 combined sample) and a band of about 95 KD (P13-15 combined sample). The two bands were subjected to disulfide bond identification, respectively. The results showed that total mismatch rate and insulin mismatch rate were both 400 for the band between 95-130 KD, and the total mismatch rate and insulin mismatch rate were both 37% for the band of about 95 KD. The results of the disulfide bonds of the band between 95-130 KD are shown in Table 10, and the results of the disulfide bonds of the band of about 95 KD are shown in Table 11. The mismatched disulfide bonds were mainly presented as the self-linking of the B chain of insulin and the mismatch between the two B chains of insulin.

TABLE 10

Detection results of disulfide bonds of 95-130 KD band of insulin precursor-Fc fusion protein (SS302-004)

| Peptide fragment | Peak time (min) | Measured molecular weight (Da) | Error (ppm) | Sequence | XIC peak area | Measured m/z | Charge number |
|---|---|---|---|---|---|---|---|
| 1:V20-21-1:V23 | 59.16 | 7694.7361 | 4 | MTKNQVSLTCLVKGFYPSDIAVEWE=NNYKTTPPMLDSDGSFFLYSKLTVDKSRWQQGNVFSCSVLHE | 46691960 | 1100.1114 | 7 |
| 1:V11-12-1:V17 | 32.48 | 3161.5451 | −1.3 | VTCVVVDVSHEDPE=YKCKVSNKGLPASIE | 167953840 | 791.1417 | 4 |
| 1:V1-1:V7-8 | 41.38 | 4035.9188 | 0.1 | FVNQHLCGSHLVE=GSLQKRGIVEQCCTSICSLYQLE= | 315009248 | 807.9896 | 5 |
| 1:V2-2:V2 | 51.87 | 1731.8299 | / | ALYLVCGE=ALYLVCGE | 1731012 | 866.4186 | 2 |
| 1:V1-1:V2 | 40.35 | 2347.1168 | / | FVNQHLCGSHLVE=ALYLVCGE | 14865076 | 783.0438 | 3 |

TABLE 10-continued

Detection results of disulfide bonds of 95-130 KD band of insulin precursor-Fc fusion protein (SS302-004)

| Peptide fragment | Peak time (min) | Measured molecular weight (Da) | Error (ppm) | Sequence | XIC peak area | Measured m/z | Charge number |
|---|---|---|---|---|---|---|---|
| 1:V2-1:V8 | 52.7 | 2353.0129 | / | ALYLVCGE═ QCCTSICSLYQLE═ | 1644195 | 1177.0101 | 2 |
| 1:V1-2:V1 | 32.8 | 2962.4079 | / | FVNQHLCGSHLVE═ FVNQHLCGSHLVE | 2344622 | 741.3574 | 4 |

Note:
The underline represents the fragment where the mismatched disulfide bond is located.

TABLE 11

Detection results of disulfide bonds of ~95 KD band of insulin precursor-Fc fusion protein (SS302-004)

| Peptide fragment | Peak time (min) | Measured molecular weight (Da) | Error (ppm) | Sequence | XIC peak area | Measured m/z | Charge number |
|---|---|---|---|---|---|---|---|
| 1:V1-1:V8 | 42.98 | 2968.3085 | -0.4 | FVNQHLCGSHLVE═QCC TSICSLYQLE═ | 3461461 | 742.8326 | 4 |
| 1:V20-21-1:V23 | 59.12 | 7694.7026 | -0.4 | MTKNQVSLTCLVKGFYP SDIAVEWE═NNYKTTPP MLDSDGSFFLYSKLTVDK SRWQQGNVFSCSVLHE | 32341352 | 1100.1066 | 7 |
| 1:V11-12-1:V17 | 32.56 | 3161.5447 | -1.5 | VTCVVVDVSHEDPE═YK CKVSNKGLPASIE | 60397856 | 791.1416 | 4 |
| 1:V2-2:V2 | 51.97 | 1731.8284 | / | ALYLVCGE═ALYLVCGE | 3500262 | 866.4178 | 2 |
| 1:V1-1:V2 | 40.35 | 2347.1210 | / | FVNQHLCGSHLVE═ ALYLVCGE | 46351952 | 783.0452 | 3 |
| 1:V2-1:V8 | 52.79 | 2353.0119 | / | ALYLVCGE═ QCCTSICSLYQLE═ | 619685 | 1177.0096 | 2 |
| 1:V1-2:V1 | 32.88 | 2962.4057 | / | FVNQHLCGSHLVE═ FVNQHLCGSHLVE | 5660477 | 741.3569 | 4 |
| 1:V8-2:V8 | 55.45 | 2974.2100 | / | QCCTSICSLYQLE═ QCCTSICSLYQLE═ | 1512188 | 992.0748 | 3 |

Note:
The underline represents the fragment where the mismatched disulfide bond is located.

3. SS302-012M

This molecule had disulfide bonds consistent with the theory, a total mismatch rate of 2.9% and an insulin mismatch rate of 2.2%. The results of the disulfide bonds are shown in Table 12.

TABLE 12

Detection results of disulfide bonds of insulin precursor-Fc fusion protein (SS302-012M)

| Peptide fragment | Peak time (min) | Measured molecular weight (Da) | Error (ppm) | Sequence | XIC peak area | Measured m/z | Charge number |
|---|---|---|---|---|---|---|---|
| 1:VT4-2:VT3 | 46.82 | 2801.382 | 2.4 | ALYLVCGE=NYCNGGGSVAPPPALPAPVR | 77401200 | 934.4654 | 3 |
| 2:VT31-1:VT39 | 45.31 | 2753.298 | 5 | NQVSLTCLVK=WQQGNVFSCSVMHE | 200181680 | 689.08 | 4 |
| 2:VT9-10-2:VT20 | 25.38 | 1774.804 | 2.8 | VTCVVVDVSHEDPE=CK | 277400448 | 592.2727 | 3 |
| 2:VT5-6-4:VT5-6 | 60.63 | 5814.054 | 0.2 | LPGPAVECPPCPAPPVAGPSVFLFPPKPK=LPGPAVECPPCPAPPVAGPSVFLFPPKPK | 400366784 | 969.8484 | 6 |
| 1:VT3-2:VT2 | 44.45 | 2968.325 | 5 | FVNQHLCGSHLVE=QCCTSICSLYQLE= | 520490464 | 990.113 | 3 |
| 2:VT2-2:VT20-2:VT31 | 46.82 | 2839.327 | 3.6 | QCCTSICSLYQLE=CK=NQVSLTCLVK | 11296762 | 710.5872 | 4 |
| 1:VT3x2 | 33.87 | 2962.406 | −0.9 | FVNQHLCGSHLVE= | 13642756 | 593.287 | 5 |
| 1:VT3-1:VT4 | 41.85 | 2347.132 | 4.7 | FVNQHLCGSHLVE=ALYLVCGE | 19307852 | 587.5384 | 4 |

Note:
The underline represents the fragment where the mismatched disulfide bond is located.

4. SS302-019M

This molecule had disulfide bonds consistent with the theory, a total mismatch rate of 2.8% and an insulin mismatch rate of 1.2%. The results of the disulfide bonds are shown in Table 13.

TABLE 13

Detection results of disulfide bonds of insulin precursor-Fc fusion protein (SS302-019M)

| Peptide fragment | Peak time (min) | Measured molecular weight (Da) | Error (ppm) | Sequence | XIC peak area | Measured m/z | Charge number |
|---|---|---|---|---|---|---|---|
| 1:VT5-2:VT4 | 38.44 | 2452.209 | −0.7 | LVCGE=NYCNGGAAVAPPPALPAPVR | 22246750 | 818.0746 | 3 |
| 2:VT13-14-2:VT24 | 26.29 | 1765.796 | −1.3 | VTCVVVDVSQEDPE=CK | 52450476 | 883.4016 | 2 |
| 1:VT3-2:VT2 | 35.06 | 2564.104 | 0.2 | FVNQHLCGSHLVE=QCCTSICSLE- | 135588016 | 855.3729 | 3 |
| 2:VT9-4:VT9 | 35.21 | 2449.994 | −0.8 | YGPPCPPCPAPE=YGPPCPPCPAPE | 193310336 | 1225.5006 | 2 |
| 2:VT34-2:VT43 | 40.53 | 2311.086 | −1 | NQVSLTCLVK=GNVFSCSVMHE | 206535696 | 771.0334 | 3 |
| 2:VT24-2:VT43 | 23.17 | 1456.596 | −3.7 | CK=GNVFSCSVMHE | 928513 | 728.8018 | 2 |
| 1:VT3-2:VT4 | 37.88 | 3414.682 | −0.4 | FVNQHLCGSHLVE=NYCNGGAAVAPPPALPAPVR | 1510880 | 854.426 | 4 |
| 1:VT5-2:VT43 | 34.23 | 1726.717 | −3.8 | LVCGE=GNVFSCSVMHE | 1533685 | 863.862 | 2 |

TABLE 13-continued

Detection results of disulfide bonds of insulin precursor-Fc fusion protein (SS302-019M)

| Peptide fragment | Peak time (min) | Measured molecular weight (Da) | Error (ppm) | Sequence | XIC peak area | Measured m/z | Charge number |
|---|---|---|---|---|---|---|---|
| 2:VT24-2:VT34 | 27.4 | 1351.704 | -2.8 | CK=NQVSLTCLVK | 1862756 | 676.3554 | 2 |
| 1:VT5-2:VT2 | 33.33 | 1601.627 | -2.6 | LVCGE=QCCTSICSLE= | 1953380 | 801.3173 | 2 |
| 1:VT5-2:VT34 | 36.23 | 1621.824 | -2.7 | LVCGE=NQVSLTCLVK | 2026153 | 811.4158 | 2 |
| 1:VT3-2:VT43 | 34.6 | 2689.19 | -2.1 | FVNQHLCGSHLVE=GNVFSCSVMHE | 3542051 | 673.0529 | 4 |
| 1:VT3-1:VT5 | 30.27 | 1999.935 | -0.6 | FVNQHLCGSHLVE=LVCGE | 4212471 | 667.3166 | 3 |

Note:
The underline represents the fragment where the mismatched disulfide bond is located.

5. SS302-030M

This molecule had disulfide bonds consistent with the theory, a total mismatch rate of 1.70% and an insulin mismatch rate of 0%. The results of the disulfide bonds are shown in Table 14.

TABLE 14

Detection results of disulfide bonds of insulin precursor-Fc fusion protein (SS302-030M)

| Peptide fragment | Peak time (min) | Measured molecular weight (Da) | Error (ppm) | Sequence | XIC peak area | Measured m/z | Charge number |
|---|---|---|---|---|---|---|---|
| 1:VT5-2:VT4 | 38.48 | 2452.208 | -1.4 | LVCGE=NYCNGGAAVAPPPALPAPVR | 40117228 | 818.0741 | 3 |
| 1:VT3-2:VT2 | 34.9 | 2564.101 | -1.2 | FVNQHLCGSHLVE=QCCTSICSLE= | 101441504 | 855.3717 | 3 |
| 2:VT13-14-2:VT24 | 26.15 | 1765.798 | -0.1 | VTCVVVDVSQEDPE=CK | 206735120 | 883.4027 | 2 |
| 2:VT9-4:VT9 | 35.04 | 2449.994 | -1 | YGPPCPPCPAPE=YGPPCPPCPAPE | 280355584 | 1225.5004 | 2 |
| 2:VT34-2:VT43 | 41.82 | 2293.13 | -0.9 | NQVSLTCLVK=GNVFSCSVLHE | 608834752 | 765.048 | 3 |
| 2:VT43x2 | 42.86 | 2380.065 | -2.2 | GNVFSCSVLHE= | 2241952 | 794.0264 | 3 |
| 1:VT5-2:VT43 | 36.62 | 1708.763 | -2.4 | LVCGE=GNVFSCSVLHE | 2406495 | 854.8851 | 2 |
| 1:VT5-2:VT34 | 36.18 | 1621.824 | -2.7 | LVCGE=NQVSLTCLVK | 2788118 | 811.4158 | 2 |
| 2:VT34x2 | 41.34 | 2206.188 | -2.6 | NQVSLTCLVK= | 2967141 | 736.0674 | 3 |
| 2:VT24-2:VT34 | 27.24 | 1351.704 | -2.3 | CK=NQVSLTCLVK | 3205830 | 676.3557 | 2 |
| 1:VT3-2:VT43 | 36.16 | 2671.229 | -3.7 | FVNQHLCGSHLVE=GNVFSCSVLHE | 4306797 | 891.0813 | 3 |

TABLE 14-continued

Detection results of disulfide bonds of insulin precursor-Fc fusion protein (SS302-030M)

| Peptide fragment | Peak time (min) | Measured molecular weight (Da) | Error (ppm) | Sequence | XIC peak area | Measured m/z | Charge number |
|---|---|---|---|---|---|---|---|
| 2:VT4-2:VT43 | 42.97 | 3123.506 | -2.7 | NYCNGGAAVAPPPALPAPVR═GNVFSCSVLHE | 1421928 | 1041.84 | 3 |
| 2:VT4-2:VT34 | 42.95 | 3036.571 | -1.6 | NYCNGGAAVAPPPALPAPVR═NQVSLTCLVK | 1651991 | 1012.8618 | 3 |

Note:
The underline represents the fragment where the mismatched disulfide bond is located.

6. SS302-035

This molecule had disulfide bonds consistent with the theory, a total mismatch rate of 4.3% and an insulin mismatch rate of 2.2%. The results of the disulfide bonds are shown in Table 15.

TABLE 15

Detection results of disulfide bonds of insulin precursor-Fc fusion protein (SS302-035)

| Peptide fragment | Peak time (min) | Measured molecular weight (Da) | Error (ppm) | Sequence | XIC peak area | Measured m/z | Charge number |
|---|---|---|---|---|---|---|---|
| 1:VT21-2:VT21 | 36.28 | 2449.991 | -1.9 | YGPPCPPCPAPE═YGPPCPPCPAPE | 464097280 | 1225.4993 | 2 |
| 1:VT25-26-1:VT36 | 27.77 | 1765.795 | -2 | VTCVVVDVSQEDPE═CK | 478602688 | 883.401 | 2 |
| 1:VT4-1:VT17 | 42.56 | 2773.397 | 2.1 | ALHLVCGE═NYCNGGAAVAPPPALPAPVR | 519631616 | 925.1372 | 3 |
| 1:VT3-1:VT15 | 36.69 | 2564.1 | -1.6 | FVNQHLCGSHLVE═QCCTSICSLE═ | 756947456 | 855.3714 | 3 |
| 1:VT46-1:VT55 | 42.41 | 2311.086 | -0.7 | NQVSLTCLVK═GNVFSCSVMHE | 822308096 | 771.0336 | 3 |
| 1:VT17-1:VT36 | 34.31 2 | 2182.091 | 0.8 | NYCNGGAAVAPPPALPAPVR═CK | 10774609 | 728.0353 | 3 |
| 1:VT3-1:VT36 | 23.49 | 1729.817 | 1.1 | FVNQHLCGSHLVE═CK | 12787250 | 433.2097 | 4 |
| 1:VT3-1:VT46 | 37.67 | 2584.304 | 1.1 | FVNQHLCGSHLVE═NQVSLTCLVK | 19985978 | 646.8314 | 4 |
| 1:VT36-1:VT46 | 29.34 | 1351.705 | -1.9 | CK═NQVSLTCLVK | 23382312 | 451.2398 | 3 |
| 1:VT15-1:VT17 | 45.75 | 3016.37 | -2.8 | QCCTSICSLE═NYCNGGAAVAPPPALPAPVR═ | 30024990 | 1006.1281 | 3 |
| 1:VT3-1:VT17 | 39.41 | 3414.679 | -1.2 | FVNQHLCGSHLVE═NYCNGGAAVAPPPALPAPVR | 39546540 | 854.4252 | 4 |

Note: The underline represents the fragment where the mismatched disulfide bond is located.

7. SS302-035M

This molecule had disulfide bonds consistent with the theory, a total mismatch rate of 2.5% and an insulin mismatch rate of 2.0%. The results of the disulfide bonds are shown in Table 16.

TABLE 16

Detection results of disulfide bonds of insulin precursor-Fc fusion protein (SS302-035M)

| Peptide fragment | Peak time (min) | Measured molecular weight (Da) | Error (ppm) | Sequence | XIC peak area | Measured m/z | Charge number |
|---|---|---|---|---|---|---|---|
| 1:VT4-2:VT4 | 42.38 | 2773.3961 | 1.8 | ALHLVCGE═NYCNGGAAVAPPPALPAPVR | 173933392 | 925.1369 | 3 |
| 2:VT12-13-2:VT23 | 27.91 | 1765.7966 | −0.9 | VTCVVVDVSQEDPE═CK | 217509472 | 883.402 | 2 |
| 2:VT33-2:VT42 | 42.48 | 2311.0837 | −1.8 | NQVSLTCLVK═GNVFSCSVMHE | 258554240 | 771.0328 | 3 |
| 2:VT8-4:VT8 | 36.23 | 2449.9915 | −1.8 | YGPPCPPCPAPE═YGPPCPPCPAPE | 265521792 | 1225.4994 | 2 |
| 1:VT3-2:VT2 | 36.69 | 2564.1129 | 3.6 | FVNQHLCGSHLVE═QCCTSICSLE═ | 546849088 | 855.3758 | 3 |
| <u>2:VT2-2:VT4</u> | 45.04 | 3016.3713 | −2.3 | QCCTSICSLE═NYCNGGAAVAPPPALPAPVR═ | 5217733 | 1006.1286 | 3 |
| <u>1:VT3-2:VT33</u> | 37.63 | 2584.3074 | 2.5 | FVNQHLCGSHLVE═NQVSLTCLVK | 8513202 | 646.8323 | 4 |
| <u>1:VT3x2</u> | 33.69 | 2962.4149 | 2.1 | FVNQHLCGSHLVE═ | 10616945 | 741.3592 | 4 |
| <u>1:VT3-2:VT4</u> | 39.29 | 3414.6839 | 0.2 | FVNQHLCGSHLVE═NYCNGGAAVAPPPALPAPVR | 13801928 | 854.4264 | 4 |

Note:
The underline represents the fragment where the mismatched disulfide bond is located.

Example 5: Hypoglycemic Effect of SS302-002 and SS302-002M on Kunming Mice 24 healthy male Kunming mice (22-28 g) were randomly divided into 4 groups, 6 mice/group: (1) SS302-002M—24 nmol/kg; (2) SS302-002—24 nmol/kg; (3) insulin glargine—48 nmol/kg; and (4) negative control group. The administration was performed by subcutaneous injection in the neck. The blood glucose level was detected at 0, 1, 2, 4, 6, 8, 10, 12, 24, 36, 48, 60, 72, and 96 h, respectively. During the experiment, the mice were not fasted, and were given sufficient water and food.

Figure 4:
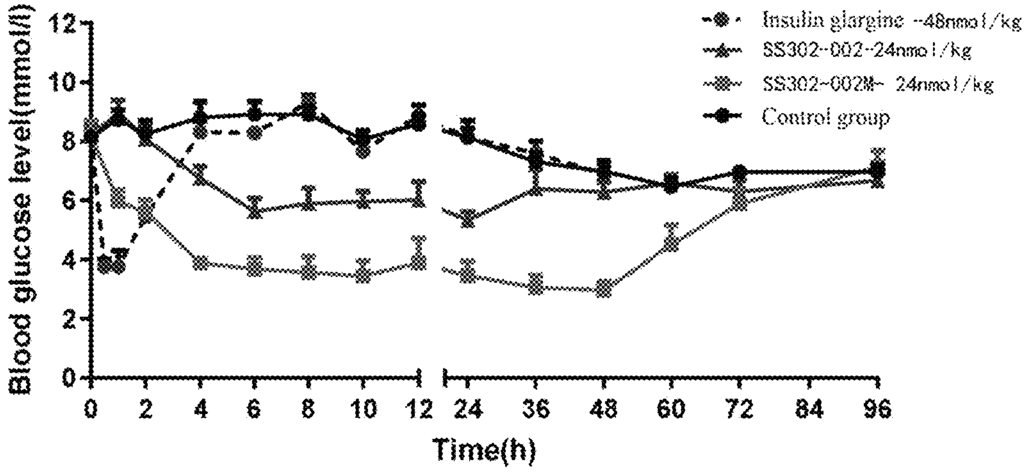
FIG. 4 shows the results of the efficacy of molecule SS 302-002 in normal Kunming mice before and after being cleaved by protease.

As shown in FIG. 4, the efficacy of insulin glargine lasted until 4 h. The SS302-002 group started to show obvious hypoglycemic effect at 4 h after administration, but was significantly weaker than the SS302-002M group in terms of hypoglycemic effect and duration of efficacy, with the maximum hypoglycemic effect of the SS302-002 group vs. the SS302-002M group being 5.33 vs. 2.97 mmol/L and the duration of efficacy of the SS302-002 group vs. the SS302-002M group being 36 h vs. 72 h. The above data analysis indicated that the insulin fusion protein after the removal of C-peptide had higher titer and better hypoglycemic effect.

Example 6: Hypoglycemic Effect of SS302-008M, SS302-012M, SS302-014M, SS302-015M, SS302-019M, SS302-029M, SS302-030M and SS302-035M on normal C57 mice 50 healthy male C57 mice aged 8-10 weeks and weighing 22-28 g were randomly divided into 10 groups, 5 mice/group, including SS302-008M, SS302-012M, SS302-014M, SS302-015M, SS302-019M, SS302-029M, SS302-030M, SS302-035M, insulin degludec and control group. The samples to be tested were administered subcutaneously at the neck at 15 nmol/kg and insulin degludec at 30 nmol/kg. The blood glucose level was detected at different time points before and after administration. During the experiment, the mice were not fasted. The experimental data were plotted using Graphpad prism 7.0, and the difference was statistically analyzed by Mann-Whitney test.

Figure 5:
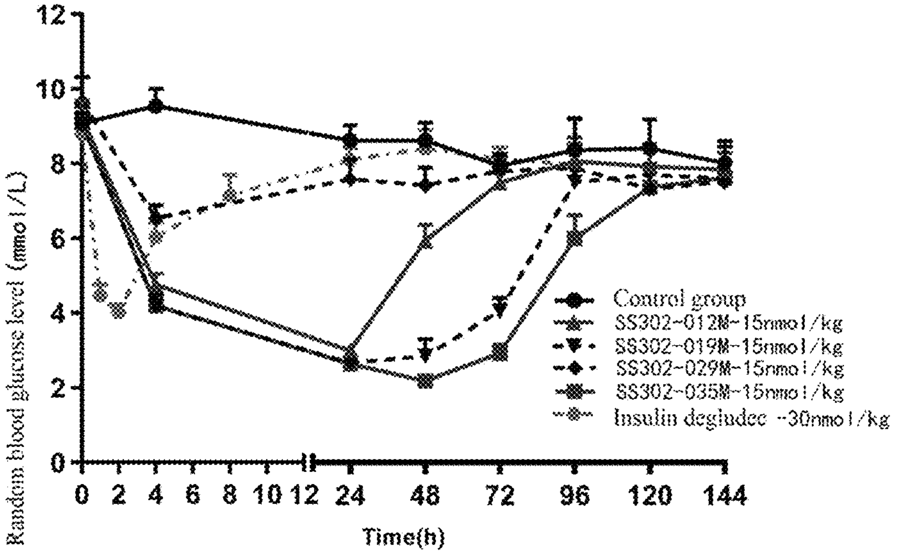
FIG. 5 shows the results of hypoglycemic effect of different fusion proteins on normal C57 mice; 5A shows the results of SS302-012M, SS302-019M, SS302-029M and SS302-035M, and 5B shows the results of SS302-008M, SS302 014M, SS302-015M and SS302-030M.
Figure 5:
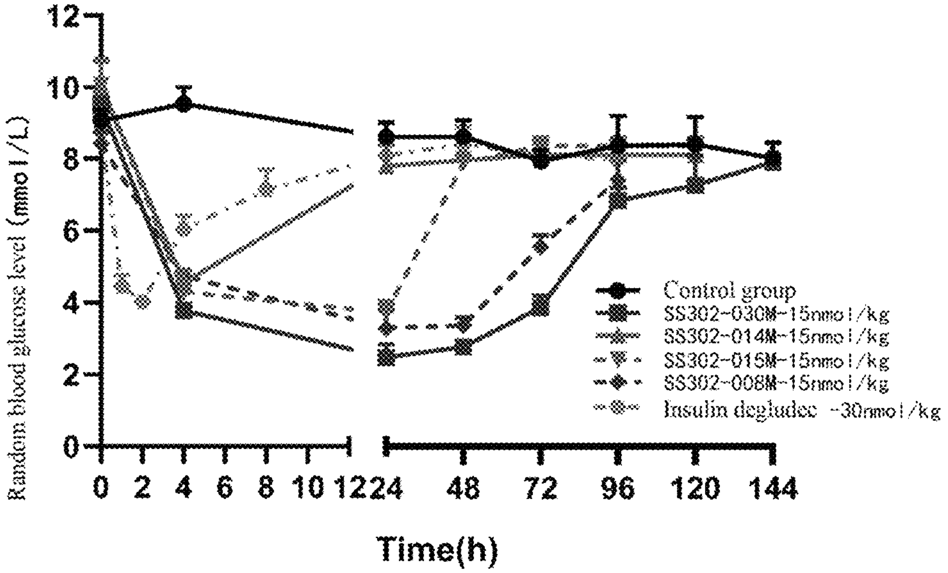

As shown in FIGS. 5A and 5B, the mice in the administration group had obvious hypoglycemic effect compared with the control group. The efficacy of insulin degludec (30 nmol/kg) lasted until 12 h. At a dose of 15 nmol/kg, the duration of efficacy of different insulin fusion proteins on normal C57 mice was as follows: SS302-035M/SS302-030M/SS302-019M/SS302-008M(96 h)>SS302-012M(72 h)>SS302-015M(48 h)>SS302-029M/SS302-014M(24 h).

Example 7: Hypoglycemic Effect of Different Doses of SS302-035M on Normal C57 Mice

[0260]25 healthy male C57 mice aged 8-10 weeks and weighing 22-28 g were randomly divided into 5 groups, 5 mice/group. SS302-035M was administered subcutaneously in the neck at 5, 7.5, 10, and 12.5 nmol/kg, respectively, and the blood glucose level was detected at 0, 4, 24, 48, 72, 96, and 120 h. During the experiment, the mice were not fasted. The experimental data were plotted using Graphpad prism 7.0, and the difference was statistically analyzed by Mann-Whitney test.

Figure 6:
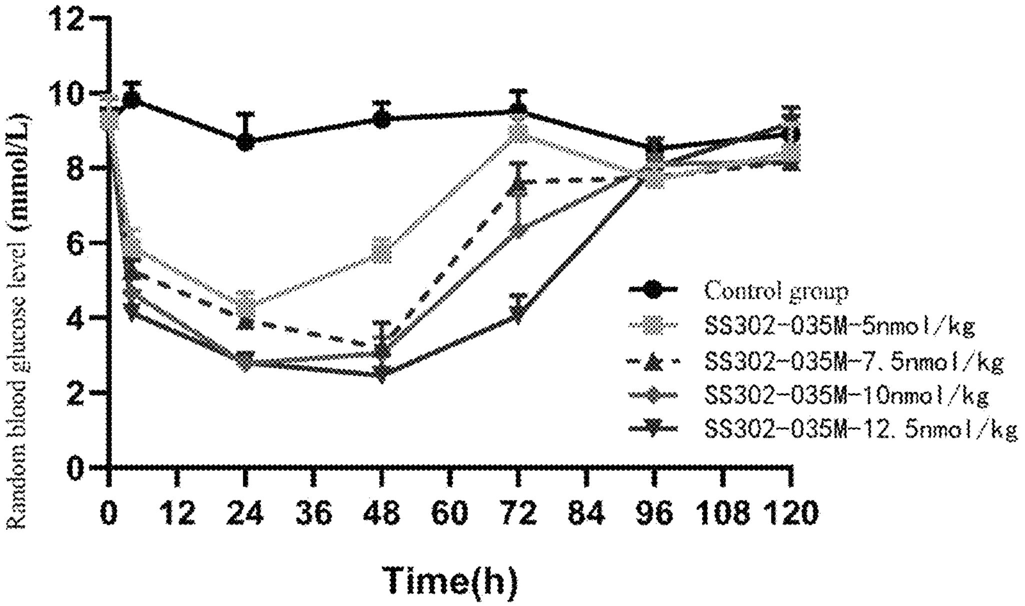
FIG. 6 shows a dose-effect curve of SS302-035M in normal C57 mice.

As shown in FIG. 6, the hypoglycemic effect of SS302-035M on normal C57 mice was obviously dose-dependent. In the SS302-035M—5 nmol/kg group, the lowest blood glucose value was 4.3 mmol/L and the efficacy lasted until 72 h; in the SSS302-035M—7.5 nmol/kg group, the lowest blood glucose value was 3.2 mmol/L and the efficacy lasted until 72 h; in the SSS302-035M—10 nmol/kg group, the lowest blood glucose value was 2.8 mmol/L and the efficacy lasted until 96 h; and in the SSS302-035M—12.5 nmol/kg group, the lowest blood glucose value was 2.5 mmol/L and the efficacy lasted until 96 h.

Example 8: Hypoglycemic Effect of SS302-004M and SS302-002M on Diabetic Model Mice 1. STZ-Induced Type I Diabetes Mouse Model C57BL/6j mice (8 weeks old, body weight of 22-28 g) were intraperitoneally injected with 0.4% streptozotocin (STZ) solution prepared in citric acid-sodium citrate buffer at 40 mg/kg for five consecutive days, once a day, and the fasting blood glucose level was detected on the 7th to 10th day after the last administration. A fasting blood glucose level >13.8 mmol/L (fasting time of 8:00 a.m-14:00 p.m) was considered as successful modeling.

2. In Vivo Activity and Long-Term Efficacy Assay

35 STZ-induced type I diabetic mice were randomly divided into 7 groups according to their blood glucose level: 1~2: high and low dose groups of SS302-002M; 3~4: high and low dose groups of SS302-004M; 5~6: high and low dose groups of insulin glargine; and (7) control group (20 mM Tris+300 mM NaCl). Among them, the high and low dose groups of SS302-002M and SS302-004M were respectively administered at 12.5 nmol/kg and 6.25 nmol/kg by subcutaneous injection in the neck, and the high and low dose groups of insulin glargine were respectively administered at 25 nmol/kg and 12.5 nmol/kg by subcutaneous injection in the neck. Changes in blood glucose levels were monitored at different time points before and after administration. During the experiment, the mice were not fasted, and were given sufficient water and food.

Figure 7:
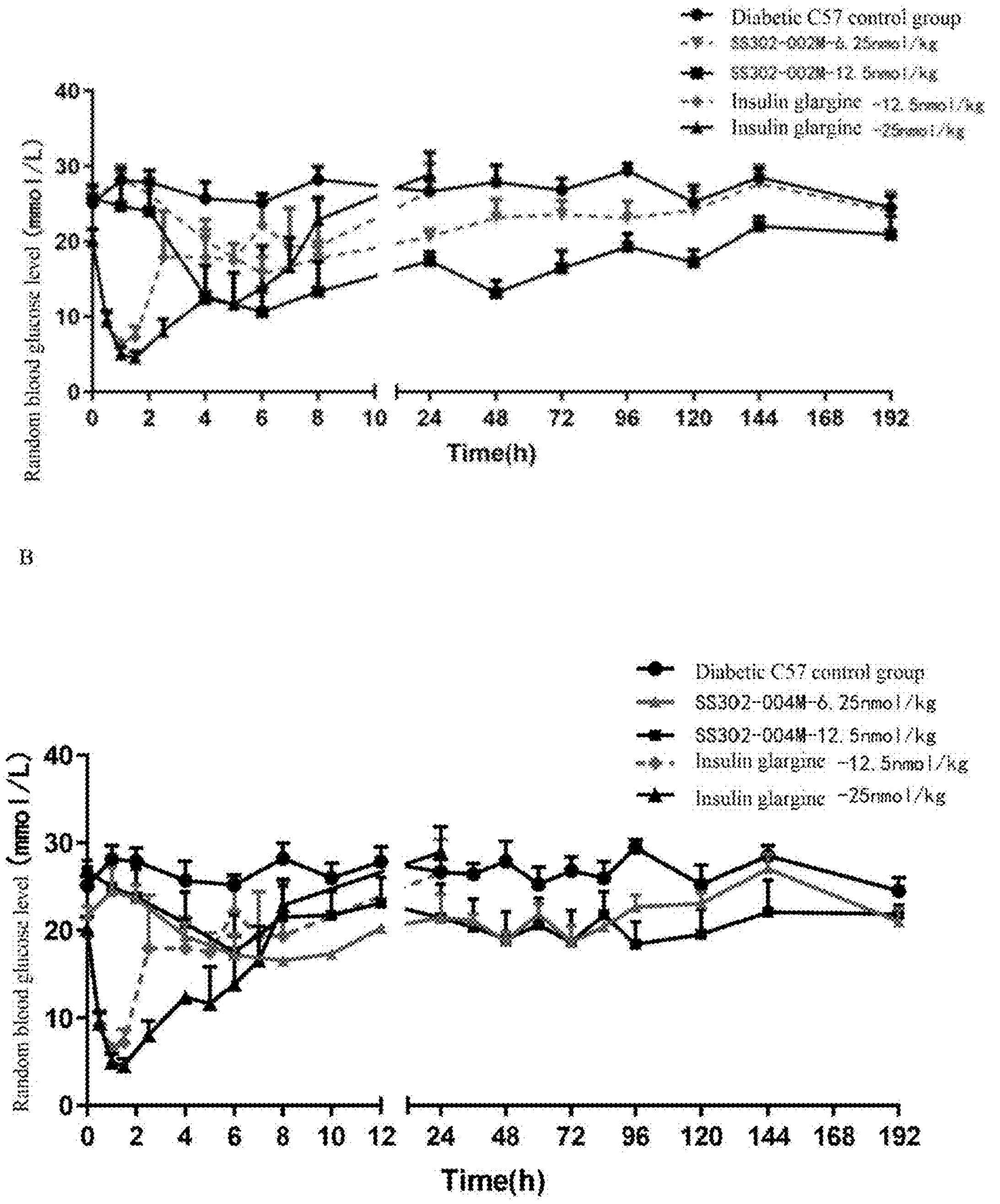
FIG. 7 shows the hypoglycemic effects of SS302-002M (7A) and SS302-004M (7B) in type I diabetes model mice.

The results are shown in FIGS. 7A (SS302-002M) and 7B (SS302-004M). After administration of SS302-002M or SS302-004M in STZ-induced type I diabetic mice, there was obvious hypoglycemic effect. The efficacy of the low dose group of S302-002M lasted until 120 h, and the efficacy of the high dose group lasted until 192 h. The efficacy of the low dose group of S302-004M lasted until 84 h, and the efficacy of the high dose group lasted until 144 h.

It is worth noting that at the same moles of insulin, i.e., at a dose of 25 nmol/kg, the blood glucose level decreased and recovered more rapidly in the insulin glargine group than in the SS302-002M and SS302-004M groups, dropped to the lowest blood glucose level (about 5 mmol/L) about 1 hour after administration (lower than the normal C57 blood glucose level of about 8 mmol/L), then quickly rose again, and returned to the initial blood glucose level at 6 h. This suggests that SS302-002M and SS302-004M had a more steady and stable PD profile and higher clinical safety.

Example 9: Hypoglycemic Effect of SS302-008M, SS302-012M and SS302-035M on Diabetic Model Mice 1. STZ-Induced Type I Diabetes Mouse Model C57BL/6j mice (12 weeks old, body weight of 22-28 g) were intraperitoneally injected with 0.4% streptozotocin (STZ) solution prepared in citric acid-sodium citrate buffer at 40 mg/kg for five consecutive days, once a day, and a fasting blood glucose level detected on the 7th to 10th day after the last administration >13.8 mmol/L (fasting time of 8:00 a.m-14:00 p.m) was considered as successful modeling.

2. In Vivo Activity and Long-Term Efficacy Assay 40 successfully STZ-modeled type I diabetic mice were randomly divided into 8 groups according to their blood glucose level: (1) SS302-008M—7.5 nmol/kg group; (2) SS302-012M—7.5 nmol/kg group; (3) SS302-035M—7.5 nmol/kg group; (4) SS302-008M—15 nmol/kg group; (5) SS302-012M—15 nmol/kg group; (6) SS302-035M—15 nmol/kg group; (7) insulin degludec—30 nmol/kg; and (8) buffer control group (20 mM Tris+150 mM NaCl). The blood glucose level was detected at different time points before and after administration. During the experiment, the mice were not fasted. The experimental results were plotted using Graphpad prism 7.0, and the difference was statistically analyzed by Mann-Whitney test.

Figure 8:
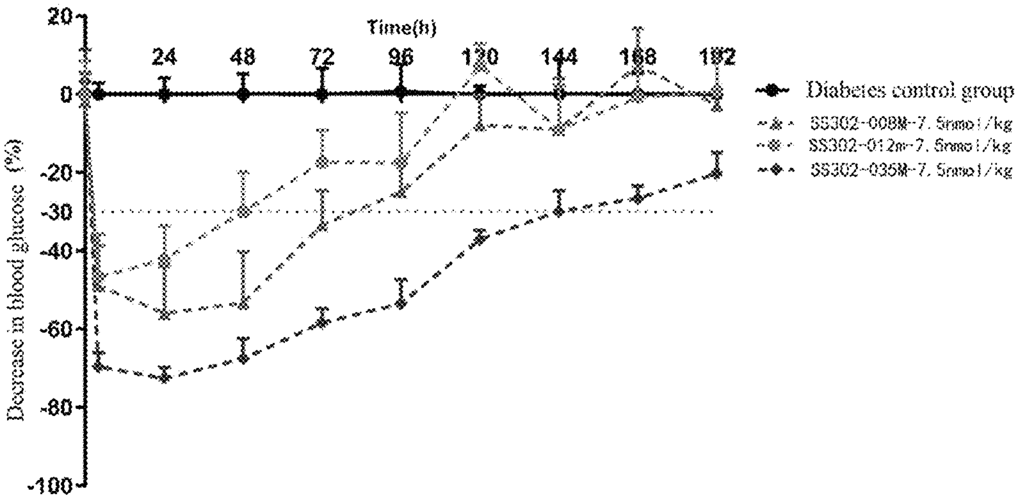
FIGS. 8A and 8B show the hypoglycemic effects of SS302-008M, SS302-012M and SS302-035M in type I diabetes model mice.
Figure 8:
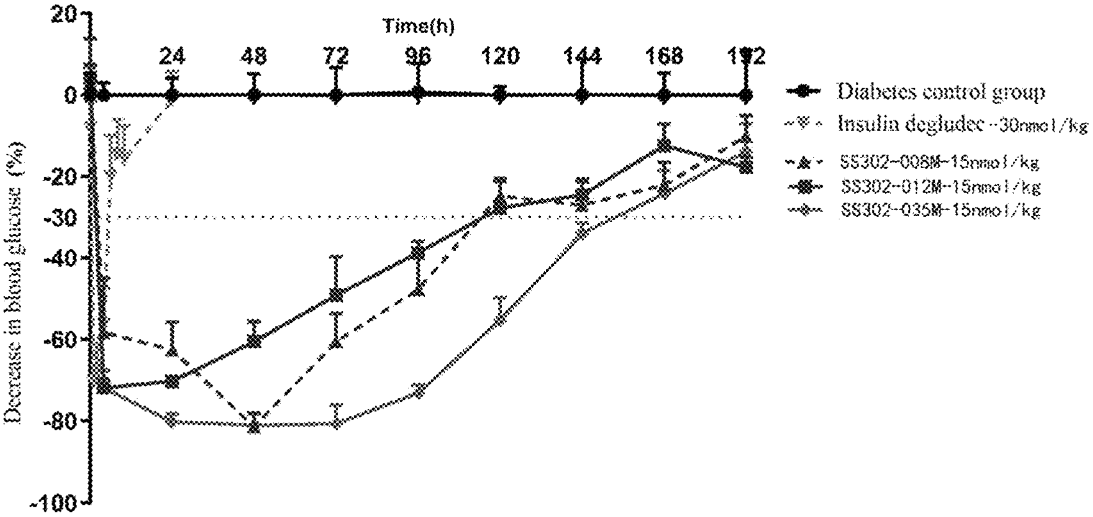

As shown in FIGS. 8A and 8B, the duration of efficacy of SS302-035M was significantly longer than that of SS302-008M and S302-012M at the same dose, especially in the low dose 7.5 nmol/kg groups (144 h vs. 72 h). In FIG. 8B, after administration of insulin degludec at 30 nmol/kg, the blood glucose level of the diabetic mice decreased and recovered rapidly, dropped to the lowest at about 1 h, and returned to the initial blood glucose level at 24 h. This suggests that SS302-008M, SS302-012M and SS302-035M had a longer PD profile, and the duration of efficacy was much longer than that of insulin degludec.

Example 10: Pharmacodynamic (PD) and Pharmacokinetic (PK) Experiments of SS302-008M and SS302-012M in SD Rats 10 SD rats (8-10 weeks old, body weight of 250-350 g) were randomly divided into 2 groups with 3♂/2♀ in each group, and SS302-008M or SS302-012M were administered subcutaneously in the neck at 20 nmol/kg, respectively. The blood glucose level was detected at different time points before and after administration, and whole blood was collected to separate serum for PK detection. During the experiment, the mice were not fasted, and were given sufficient water and food. All data were plotted with Graphpad prism 7.0, and the difference was statistically analyzed by Mann-Whitney test.

2. ELISA Detection

Mouse anti-insulin monoclonal antibody (abcam, ab8302) was diluted with PBS to 1 μg/mL, added to a microplate at 100 μL/well, and placed at 4° C. overnight for coating. After the removal of the coating solution, the plate was washed with PBST 4 times, then added with 4% BSA at 250 μl/well, and blocked at 37° C. for 2 h. After the removal of the blocking solution, the plate was washed with PBST 4 times. The SS302-008M/SS302-012M standard was serially diluted with 2% BSA to obtain a total of 8 gradients starting from 200 ng/ml to establish a standard curve. Rat serum was diluted to various gradients with 2% BSA. The negative control was normal rat serum. The above samples were added to a microplate at 100 μl/well and incubated at 37° C. for 1 h. The plate was then washed 4 times with PBST, added with a secondary antibody (Mouse monoclonal Anti-Human IgG2 Fc (HRP), 1:3000) (abcam, ab99779) diluted with 2% BSA at 100 μL/well and incubated at 37° C. for 1 h. The plate was then washed 4 times with PBST, added with TMB chromogen solution at 100 μl/well to develop color at 37° C. in dark for 10 min, and then added with 2M $H_2SO_4$ at 50 μL/well to stop the reaction. The OD450/630 value was detected by a microplate reader.

3. Pharmacodynamic Results

Figure 9:
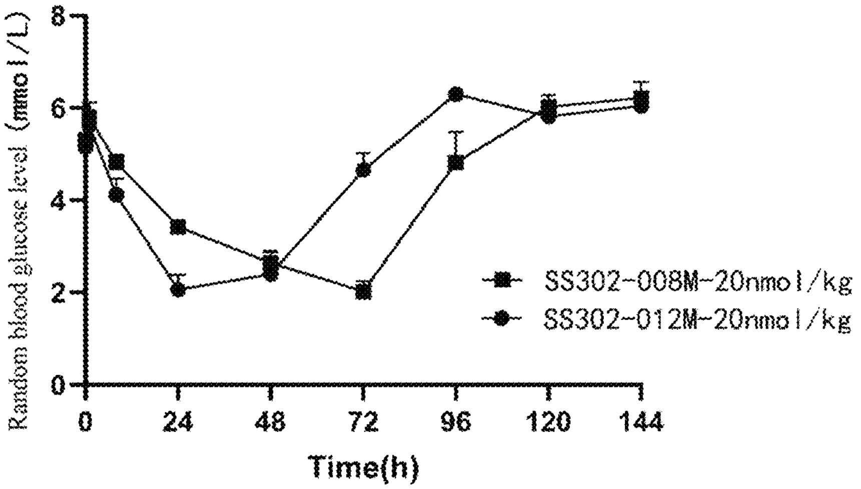
FIG. 9 shows the results of the efficacy of SS302-008M and SS302-012M in normal SD rats.

As shown in FIG. 9, SD rats had obvious hypoglycemic effect after administration of SS302-008M and SS302-

Figure 10:
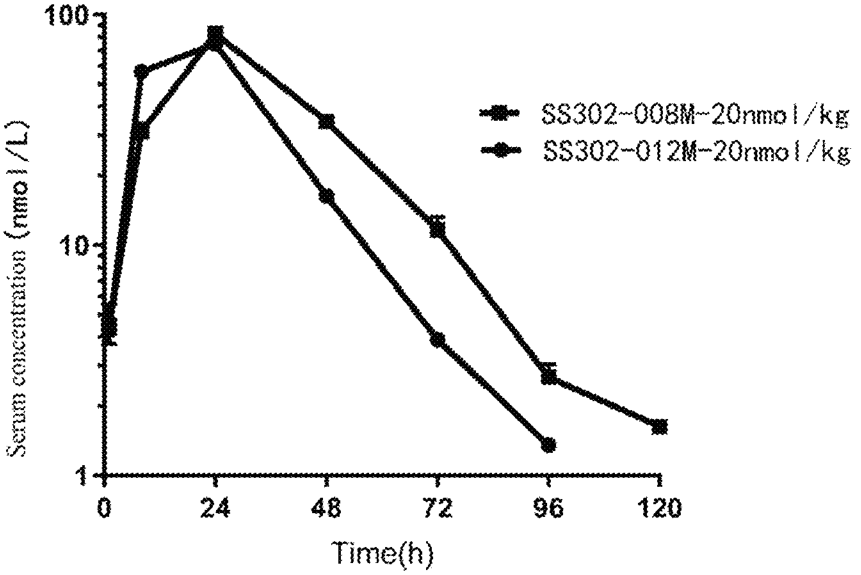
FIG. 10 shows the pharmacokinetic results of SS302-008M and SS302-012M in SD rats.

012M. The efficacy of SS302-008M lasted until 96 h, while the efficacy of SS302-012M lasted until 72 h. 4. Pharmacokinetic results and analysis The pharmacokinetic results of SS302-008M and SS302-012M in SD rats are shown in FIG. 10. The half-lives (T½) of SS302-008M and SS302-012M in SD rats were 16.32±0.77 h and 13.39±0.43 h, respectively. The specific PK parameters are shown in Table 17.

TABLE 17

PK parameters for SS302-008M and SS302-012M

| Group | SS3302-008M | SS3302-0012M |
|---|---|---|
| T1/2 (hr) | 16.32 ± 0.77 | 13.39 ± 0.43 |
| Tmax (hr) | 24.00 ± 0 | 24.00 ± 0 |
| Cmax (nmol/L) | 82.71 ± 7.77 | 74.72 ± 8.66 |
| AUC (hr*nmol/L) | 3217.73 ± 326.15 | 2664.67 ± 208.28 |
| Vss (L/kg) | 0.289 ± 0.039 | 0.289 ± 0.031 |
| Cl (L/hr/kg) | 0.012 ± 0.001 | 0.015 ± 0.001 |
| MRT (hr) | 34.41 ± 2.23 | 25.60 ± 2.23 |

Figure 11:
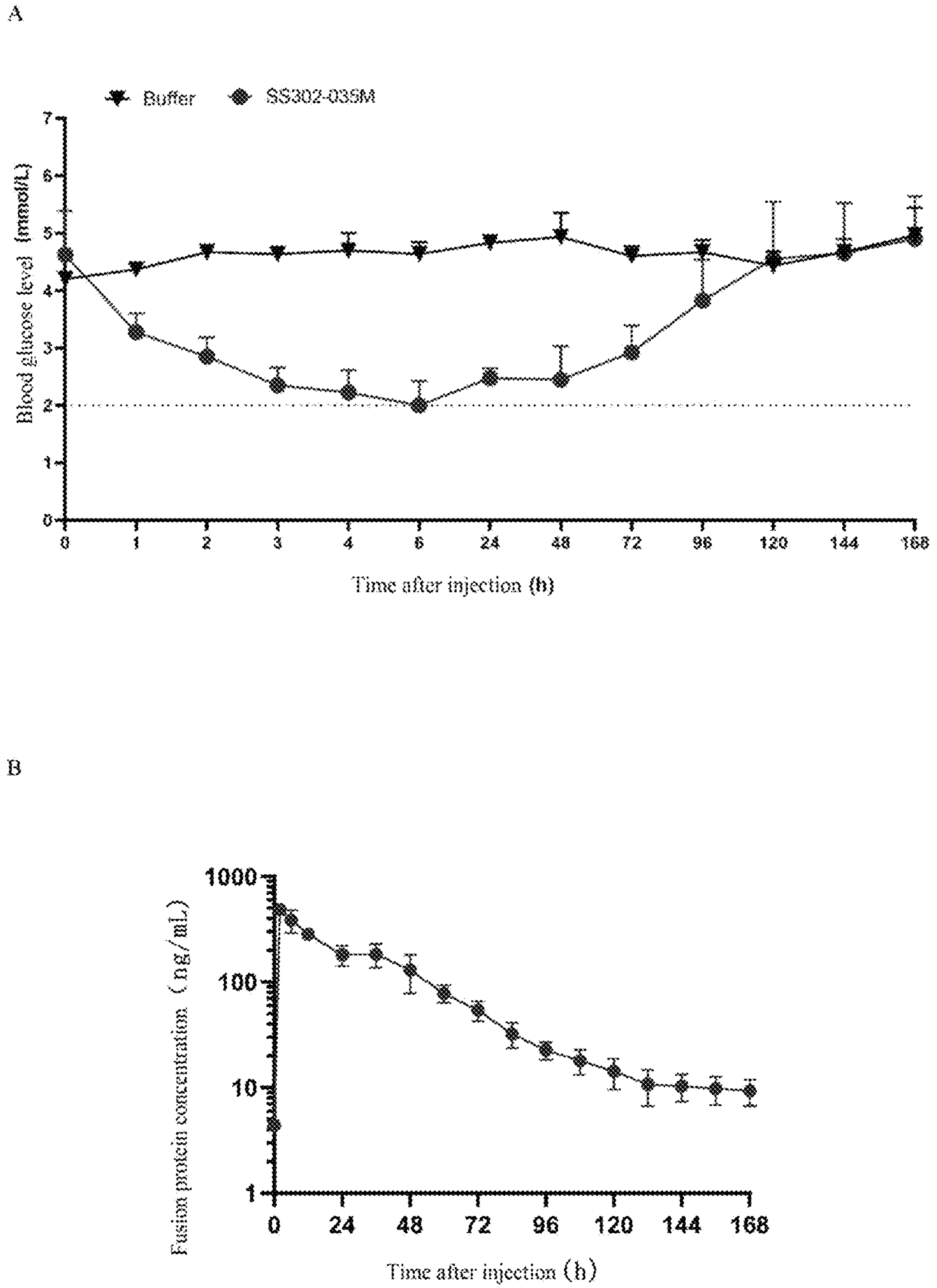
FIG. 11 shows the hypoglycemic effects (11A) and serum drug concentration-time curve (11B) of SS302-035M in beagle dogs.

Example 11: Pharmacodynamic (PD) and Pharmacokinetic (PK) Experiments of SS302-035M in Beagle Dogs 4 male healthy general-grade beagle dogs weighing 8-12 kg were evaluated for pharmacodynamic and pharmacokinetic parameters after a single subcutaneous administration of 2.5 nmol/kg SS302-035M. Blood samples were collected at different time points before and after administration, and the sampling sites were peripheral veins of four limbs. About 1 mL of whole blood was collected at each time point, put into an anticoagulant tube containing EDTA-K2, and then centrifuged at 3000 g/min for 10 min at 4° C. to collect plasma. A drop of whole blood at time points 0 h before administration and 1, 2, 3, 4, 6, 24, 48, 72, 96, 120, 144 and 168 h after administration was taken to detect the blood glucose level of the animal using a blood glucose meter (Roche's ACCU-CHEK Performa) and blood glucose test strips (Roche's ACCU-CHEK Performa). The pharmacodynamic (PD) results are shown in FIG. 11A, and the pharmacokinetic (PK) results are shown in FIG. 11B. During the experiment, the animals were fasted at 0-6 h, and then ate and drank freely. The pharmacokinetic parameters (non-compartmental model) were calculated using WinNonlin 8.2 software, and the relevant PK parameters are shown in Table 18. The PD results showed that SS302-035M at a dose of 2.5 nmol/kg could significantly reduce the random blood glucose of beagle dogs, and the hypoglycemic effect lasted until 120 h without obvious symptoms of hypoglycemia. The PK results showed that SS302-035M at a dose of 2.5 nmol/kg had an in vivo half-life in normal beagle dogs of 37.65±7.36h.

TABLE 18

PK parameters for SS302-035M

| PK parameter | Result |
|---|---|
| $AUC_{0-\infty}$ (ng*hr/mL) | 14631.28 ± 628.94 |
| T1/2 (hr) | 37.65 ± 7.36 |
| $T_{max}$ (hr) | 2 ± 0 |
| $C_{max}$ (ng/mL) | 485.75 ± 26.18 |
| Vss (mL/kg) | 498.53 ± 55.90 |
| CL (mL/hr/kg) | 11.83 ± 1.29 |
| MRT (hr) | 39.05 ± 4.11 |

The full-length sequences of the fusion protein precursors constructed in the examples of the present disclosure are as follows:

```
1) Insulin precursor fusion protein SS302-001
                                        SEQ ID NO: 47
FVNQHLCGSHLVEALYLVCGERGFFYTPKTRREAEDLQVG

QVELGGGPGAGSLQPLALEGSLQKRGIVEQCCTSICSLYQ

LENYCNGSGGGGSGGGGSGGGGSGGGGSGGGGSSSSSKAP

PPSLPSPSRLPGPSDTPILPQEPKSCDKTHTCPPCPAPEL

LGGPSVFLFPPKPKDTLMISRTPEVTCVVVDVSHEDPEVK

FNWYVDGVEVHNAKTKPREEQYNSTYRVVSVLTVLHQDWL

NGKEYKCKVSNKALPAPIEKTISKAKGQPREPQVYTLPPS

RDELTKNQVSLTCLVKGFYPSDIAVEWESNGQPENNYKTT

PPVLDSDGSFFLYSKLTVDKSRWQQGNVFSCSVMHEALHN

HYTQKSLSLSPG

2) Insulin precursor fusion protein SS302-002
                                        SEQ ID NO: 48
FVNQHLCGSHLVEALYLVCGERGFFYTPKTRREAEDLQVG

QVELGGGPGAGSLQPLALEGSLQKRGIVEQCCTSICSLYQ

LENYCNGSGGGGSGGGGSGGGGSGGGGSGGGGSSSSSKAP

PPSLPSPSRLPGPSDTPILPQVECPPCPAPPVAGPSVFLF

PPKPKDQLMISRTPEVTCVVVDVSHEDPEVQFNWYVDGVE

VHNAKTKPREEQFNSTFRVVSVLTVVHQDWLNGKEYKCKV

SNKGLPASIEKTISKTKGQPREPQVYTLPPSREEMTKNQV

SLTCLVKGFYPSDIAVEWESNGQPENNYKTTPPMLDSDGS

FFLYSKLTVDKSRWQQGNVFSCSVLHEALHNHYTQKSLSL

SPGK

3) Insulin precursor fusion protein SS302-003
                                        SEQ ID NO: 49
FVNQHLCGSHLVEALYLVCGERGFFYTPKTRREAEDLQVG

QVELGGGPGAGSLQPLALEGSLQKRGIVEQCCTSICSLYQ

LENYCNGSGGGGSGGGGSGGGGSGGGGSGGGGSSSSSKAP

PPSLPSPSRLPGPSDTPILPQESKYGPPCPPCPAPEFLGG

PSVFLFPPKPKDTLMISRTPEVTCVVVDVSQEDPEVQFNW

YVDGVEVHNAKTKPREEQFNSTYRVVSVLTVLHQDWLNGK

EYKCKVSNKGLPSSIEKTISKAKGQPREPQVYTLPPSQEE

MTKNQVSLTCLVKGFYPSDIAVEWESNGQPENNYKTTPPV

LDSDGSFFLYSRLTVDKSRWQEGNVFSCSVMHEALHNHYT

QKSLSLSLG
```

-continued

4) Insulin precursor fusion protein SS302-004

SEQ ID NO: 50

FVNQHLCGSHLVEALYLVCGERGFFYTPKTRREAEDLQVG

QVELGGGPGAGSLQPLALEGSLQKRGIVEQCCTSICSLYQ

LENYCNGSGGGGSGGGGSGGGGSGGGGSGGGGSVECPPCP

APPVAGPSVFLFPPKPKDQLMISRTPEVTCVVVDVSHEDP

EVQFNWYVDGVEVHNAKTKPREEQFNSTFRVVSVLTVVHQ

DWLNGKEYKCKVSNKGLPASIEKTISKTKGQPREPQVYTL

PPSREEMTKNQVSLTCLVKGFYPSDIAVEWESNGQPENNY

KTTPPMLDSDGSFFLYSKLTVDKSRWQQGNVFSCSVLHEA

LHNHYTQKSLSLSPGK

5) Insulin precursor fusion protein SS302-005

SEQ ID NO: 51

FVNQHLCGSHLVEALYLVCGERGFFYTPKTRREAEDLQVG

QVELGGGPGAGSLQPLALEGSLQKRGIVEQCCTSICSLYQ

LENYCNGGGGSGGGGSGGGGSGGGGSGGGGSVECPPCPAP

PVAGPSVFLFPPKPKDQLMISRTPEVTCVVVDVSHEDPEV

QFNWYVDGVEVHNAKTKPREEQFASTFRVVSVLTVVHQDW

LNGKEYKCKVSNKGLPASIEKTISKTKGQPREPQVYTLPP

SREEMTKNQVSLTCLVKGFYPSDIAVEWESNGQPENNYKT

TPPMLDSDGSFFLYSKLTVDKSRWQQGNVFSCSVLHEALH

NHYTQKSLSLSPGK

6)
Insulin precursor fusion protein SS302-006

SEQ ID NO: 52

FVNQHLCGSHLVEALYLVCGERGFFYTPKTRREAEDLQVG

QVELGGGPGAGSLQPLALEGSLQKRGIVEQCCTSICSLYQ

LENYCNSASSKAPPPSLPSPSRLPGPSDTPILPQVECPPC

PAPPVAGPSVFLFPPKPKDTLMISRTPEVTCVVVDVSHED

PEVQFNWYVDGVEVHNAKTKPREEQFNSTFRVVSVLTVVH

QDWLNGKEYKCKVSNKGLPAPIEKTISKTKGQPREPQVYT

LPPSREEMTKNQVSLTCLVKGFYPSDIAVEWESNGQPENN

YKTTPPMLDSDGSFFLYSKLTVDKSRWQQGNVFSCSVMHE

ALHNHYTQKSLSLSPGK

7) Insulin precursor fusion protein SS302-007

SEQ ID NO: 53

FVNQHLCGSHLVEALYLVCGERGFFYTPKTRREAEDLQVG

QVELGGGPGAGSLQPLALEGSLQKRGIVEQCCTSICSLYQ

LENYCNSSSSKAPPPSLPSPSRLPGPSDTPILPQVECPPC

PAPPVAGPSVFLFPPKPKDTLMISRTPEVTCVVVDVSHED

PEVQFNWYVDGVEVHNAKTKPREEQFNSTFRVVSVLTVVH

QDWLNGKEYKCKVSNKGLPAPIEKTISKTKGQPREPQVYT

LPPSREEMTKNQVSLTCLVKGFYPSDIAVEWESNGQPENN

YKTTPPMLDSDGSFFLYSKLTVDKSRWQQGNVFSCSVMHE

ALHNHYTQKSLSLSPGK

-continued

8) Insulin precursor fusion protein SS302-008

SEQ ID NO: 54

FVNQHLCGSHLVEALYLVCGERGFFYTPKTRREAEDLQVG

QVELGGGPGAGSLQPLALEGSLQKRGIVEQCCTSICSLYQ

LENYCNSASSKAPPPSLPSPSRLPGPSDTPILPQSSSSKA

PPPSLPSPSRLPGPSDTPILPQVECPPCPAPPVAGPSVFL

FPPKPKDTLMISRTPEVTCVVVDVSHEDPEVQFNWYVDGV

EVHNAKTKPREEQFNSTFRVVSVLTVVHQDWLNGKEYKCK

VSNKGLPAPIEKTISKTKGQPREPQVYTLPPSREEMTKNQ

VSLTCLVKGFYPSDIAVEWESNGQPENNYKTTPPMLDSDG

SFFLYSKLTVDKSRWQQGNVFSCSVMHEALHNHYTQKSLS

LS
PGK

9) Insulin precursor fusion protein SS302-009

SEQ ID NO: 55

FVNQHLCGSHLVEALYLVCGERGFFYTPKTRREAEDLQVG

QVELGGGPGAGSLQPLALEGSLQKRGIVEQCCTSICSLYQ

LENYCNGGGSVAPPPALPAPVRLPGPASSSSKAPPPSLPS

PSRLPGPSDTPILPQVECPPCPAPPVAGPSVFLFPPKPKD

TLMISRTPEVTCVVVDVSHEDPEVQFNWYVDGVEVHNAKT

KPREEQFNSTFRVVSVLTVVHQDWLNGKEYKCKVSNKGLP

APIEKTISKTKGQPREPQVYTLPPSREEMTKNQVSLTCLV

KGFYPSDIAVEWESNGQPENNYKTTPPMLDSDGSFFLYSK

LTVDKSRWQQGNVFSCSVMHEALHNHYTQKSLSLSPGK

10) Insulin precursor fusion protein SS302-011

SEQ ID NO: 56

FVNQHLCGSHLVEALYLVCGERGFFYTPKTRREAEDLQVG

QVELGGGPGAGSLQPLALEGSLQKRGIVEQCCTSICSLYQ

LENYCNGGGSVAPPPALPAVAPPPALPASSSSKAPPPSLP

SPSRLPGPSDTPILPQVECPPCPAPPVAGPSVFLFPPKPK

DTLMISRTPEVTCVVVDVSHEDPEVQFNWYVDGVEVHNAK

TKPREEQFNSTFRVVSVLTVVHQDWLNGKEYKCKVSNKGL

PAPIEKTISKTKGQPREPQVYTLPPSREEMTKNQVSLTCL

VKGFYPSDIAVEWESNGQPENNYKTTPPMLDSDGSFFLYS

KLTVDKSRWQQGNVFSCSVMHEALHNHYTQKSLSLSPGK

11) Insulin precursor fusion protein SS302-012

SEQ ID NO: 57

FVNQHLCGSHLVEALYLVCGERGFFYTPKTRREAEDLQVG

QVELGGGPGAGSLQPLALEGSLQKRGIVEQCCTSICSLYQ

LENYCNGGGSVAPPPALPAPVRLPGPAVAPPPALPAPVRL

PGPAVECPPCPAPPVAGPSVFLFPPKPKDTLMISRTPEVT

CVVVDVSHEDPEVQFNWYVDGVEVHNAKTKPREEQFNSTF

RVVSVLTVVHQDWLNGKEYKCKVSNKGLPAPIEKTISKTK

-continued

GQPREPQVYTLPPSREEMTKNQVSLTCLVKGFYPSDIAVE
WESNGQPENNYKTTPPMLDSDGSFFLYSKLTVDKSRWQQG
NVFSCSVMHEALHNHYTQKSLSLSPGK

12) Insulin precursor fusion protein SS302-013

SEQ ID NO: 58

FVNQHLCGSHLVEALYLVCGERGFFYTPKTRREAEDLQVG
QVELGGGPGAGSLQPLALEGSLQKRGIVEQCCTSICSLYQ
LENYCNGGAAVAPPPALPAPVRLPGPAVAPPPALPAPVRL
PGPAVAPPPALPAPVRLPGPAVECPPCPAPPVAGPSVFLF
PPKPKDTLMISRTPEVTCVVVDVSHEDPEVQFNWYVDGVE
VHNAKTKPREEQFNSTFRVVSVLTVVHQDWLNGKEYKCKV
SNKGLPAPIEKTISKTKGQPREPQVYTLPPSREEMTKNQV
SLTCLVKGFYPSDIAVEWESNGQPENNYKTTPPMLDSDGS
FFLYSKLTVDKSRWQQGNVFSCSVMHEALHNHYTQKSLSL
SPGK

13) Insulin precursor fusion protein SS302-014

SEQ ID NO: 59

FVNQHLCGSHLVEALYLVCGERGFFYTPKTRREAEDLQVG
QVELGGGPGAGSLQPLALEGSLQKRGIVEQCCTSICSLYQ
LENYCNGGAAVAPPPALPAPVRLPGPAVAPPPALPAPVRL
PGPAVAPPPALPAPVRLPGPAVECPPCPAPPVAGPSVFLF
PPKPKDTLYITREPEVTCVVVDVSHEDPEVQFNWYVDGVE
VHNAKTKPREEQFASTFRVVSVLTVVHQDWLNGKEYKCKV
SNKGLPAPIEKTISKTKGQPREPQVYTLPPSREEMTKNQV
SLTCLVKGFYPSDIAVEWESNGQPENNYKTTPPMLDSDGS
FFLYSKLTVDKSRWQQGNVFSCSVMHEALHNHYTQKSLSL
SPGK

14) Insulin precursor fusion protein SS302-015

SEQ ID NO: 60

FVNQHLCGSHLVEALYLVCGERGFFYTPKTRREAEDLQVG
QVELGGGPGAGSLQPLALEGSLQKRGIVEQCCTSICSLYQ
LENYCNGGAAVAPPPALPAPVRLPGPAVAPPPALPAPVRL
PGPAVAPPPALPAPVRLPGPAVECPPCPAPPVAGPSVFLF
PPKPKDTLMISRTPEVTCVVVDVSHEDPEVQFNWYVDGVE
VHNAKTKPREEQFASTFRVVSVLTVVHQDWLNGKEYKCKV
SNKGLPAPIEKTISKTKGQPREPQVYTLPPSREEMTKNQV
SLTCLVKGFYPSDIAVEWESNGQPENNYKTTPPMLDSDGS
FFLYSKLTVDKSRWQQGNVFSCSVLHEALHSHYTQKSLSL
SPGK

15) Insulin precursor fusion protein SS302-016

SEQ ID NO: 61

FVNQHLCGSHLVEALYLVCGERGFFYTPKTRREAEDLQVG
QVELGGGPGAGSLQPLALEGSLQKRGIVEQCCTSICSLYQ
LENYCNGGAAVAPPPALPAPVRLPGPAVAPPPALPAPVRL
PGPAVAPPPALPAPVRLPGPAESKYGPPCPPCPAPEAAGG

-continued

PSVFLFPPKPKDTLMISRTPEVTCVVVDVSQEDPEVQFNW
YVDGVEVHNAKTKPREEQFNSTYRVVSVLTVLHQDWLNGK
EYKCKVSNKGLPSSIEKTISKAKGQPREPQVYTLPPSQEE
MTKNQVSLTCLVKGFYPSDIAVEWESNGQPENNYKTTPPV
LDSDGSFFLYSRLTVDKSRWQEGNVFSCSVMHEALHNHYT
QKSLSLSLG

16) Insulin precursor fusion protein SS302-017

SEQ ID NO: 62

FVNQHLCGSHLVEALYLVCGERGFFYTPKTRREAEDLQVG
QVELGGGPGAGSLQPLALEGSLQKRGIVEQCCTSICSLYQ
LENYCNGGAAVAPPPALPAPVRLPGPAVAPPPALPAPVRL
PGPAVAPPPALPAPVRLPGPAESKYGPPCPPCPAPEFLGG
PSVFLFPPKPKDTLYITREPEVTCVVVDVSQEDPEVQFNW
YVDGVEVHNAKTKPREEQFASTYRVVSVLTVLHQDWLNGK
EYKCKVSNKGLPSSIEKTISKAKGQPREPQVYTLPPSQEE
MTKNQVSLTCLVKGFYPSDIAVEWESNGQPENNYKTTPPV
LDSDGSFFLYSRLTVDKSRWQEGNVFSCSVMHEALHNHYT
QKSLSLSLG

17) Insulin precursor fusion protein SS302-018

SEQ ID NO: 63

FVNQHLCGSHLVEALYLVCGERGFFYTPKTRREAEDLQVG
QVELGGGPGAGSLQPLALEGSLQKRGIVEQCCTSICSLYQ
LENYCNGGAAVAPPPALPAPVRLPGPAVAPPPALPAPVRL
PGPAVAPPPALPAPVRLPGPAESKYGPPCPPCPAPEFLGG
PSVFLFPPKPKDTLMISRTPEVTCVVVDVSQEDPEVQFNW
YVDGVEVHNAKTKPREEQFASTYRVVSVLTVLHQDWLNGK
EYKCKVSNKGLPSSIEKTISKAKGQPREPQVYTLPPSQEE
MTKNQVSLTCLVKGFYPSDIAVEWESNGQPENNYKTTPPV
LDSDGSFFLYSRLTVDKSRWQEGNVFSCSVLHEALHSHYT
QKSLSLSLG

18) Insulin precursor fusion protein SS302-019

SEQ ID NO: 64

FVNQHLCGSHLVEALELVCGERGFHYTPKTRREAEDLQVG
QVELGGGPGAGSLQPLALEGSLQKRGIVEQCCTSICSLEQ
LENYCNGGAAVAPPPALPAPVRLPGPAVAPPPALPAPVRL
PGPAVAPPPALPAPVRLPGPAESKYGPPCPPCPAPEAAGG
PSVFLFPPKPKDTLMISRTPEVTCVVVDVSQEDPEVQFNW
YVDGVEVHNAKTKPREEQFNSTYRVVSVLTVLHQDWLNGK
EYKCKVSNKGLPSSIEKTISKAKGQPREPQVYTLPPSQEE

-continued

MTKNQVSLTCLVKGFYPSDIAVEWESNGQPENNYKTTPPV
LDSDGSFFLYSRLTVDKSRWQEGNVFSCSVMHEALHNHYT
QKSLSLSLG

19) Insulin precursor fusion protein SS302-022

SEQ ID NO: 65

FVNQHLCGSHLVEALYLVCGERGFFYTPKTKRIKREAEDL
QVGQVELGGGPGAGSLQPLALEGSLQKRIKRGIVEQCCTS
ICSLYQLENYCNGGGSVAPPPALPAPVRLPGPAVAPPPAL
PAPVRLPGPAVECPPCPAPPVAGPSVFLFPPKPKDTLMIS
RTPEVTCVVVDVSHEDPEVQFNWYVDGVEVHNAKTKPREE
QFNSTFRVVSVLTVVHQDWLNGKEYKCKVSNKGLPAPIEK
TISKTKGQPREPQVYTLPPSREEMTKNQVSLTCLVKGFYP
SDIAVEWESNGQPENNYKTTPPMLDSDGSFFLYSKLTVDK
SRWQQGNVFSCSVMHEALHNHYTQKSLSLSPGK

20) Insulin precursor fusion protein SS302-023

SEQ ID NO: 66

FVNQHLCGSHLVEALYLVCGERGFFYTPKTDDDDKEAEDL
QVGQVELGGGPGAGSLQPLALEGSLQKRDDDDKGIVEQCC
TSICSLYQLENYCNGGGSVAPPPALPAPVRLPGPAVAPPP
ALPAPVRLPGPAVECPPCPAPPVAGPSVFLFPPKPKDTLM
ISRTPEVTCVVVDVSHEDPEVQFNWYVDGVEVHNAKTKPR
EEQFNSTFRVVSVLTVVHQDWLNGKEYKCKVSNKGLPAPI
EKTISKTKGQPREPQVYTLPPSREEMTKNQVSLTCLVKGF
YPSDIAVEWESNGQPENNYKTTPPMLDSDGSFFLYSKLTV
DKSRWQQGNVFSCSVMHEALHNHYTQKSLSLSPGK

21) Insulin precursor fusion protein SS302-029

SEQ ID NO: 67

FVNQHLCGSHLVEALELVCGERGFHYTPKTRREAEDLQVG
QVELGGGPGAGSLQPLALEGSLQKRGIVEQCCTSICSLEQ
LENYCNGGAAVAPPPALPAPVRLPGPAVAPPPALPAPVRL
PGPAVAPPPALPAPVRLPGPAESKYGPPCPPCPAPEFLGG
PSVFLFPPKPKDTLYITREPEVTCVVVDVSQEDPEVQFNW
YVDGVEVHNAKTKPREEQFASTYRVVSVLTVLHQDWLNGK
EYKCKVSNKGLPSSIEKTISKAKGQPREPQVYTLPPSQEE
MTKNQVSLTCLVKGFYPSDIAVEWESNGQPENNYKTTPPV
LDSDGSFFLYSRLTVDKSRWQEGNVFSCSVMHEALHNHYT
QKSLSLSLG

22) Insulin precursor fusion protein SS302-030

SEQ ID NO: 68

FVNQHLCGSHLVEALELVCGERGFHYTPKTRREAEDLQVG
QVELGGGPGAGSLQPLALEGSLQKRGIVEQCCTSICSLEQ
LENYCNGGAAVAPPPALPAPVRLPGPAVAPPPALPAPVRL
PGPAVAPPPALPAPVRLPGPAESKYGPPCPPCPAPEFLGG
PSVFLFPPKPKDTLMISRTPEVTCVVVDVSQEDPEVQFNW
YVDGVEVHNAKTKPREEQFASTYRVVSVLTVLHQDWLNGK
EYKCKVSNKGLPSSIEKTISKAKGQPREPQVYTLPPSQEE
MTKNQVSLTCLVKGFYPSDIAVEWESNGQPENNYKTTPPV
LDSDGSFFLYSRLTVDKSRWQEGNVFSCSVLHEALHSHYT
QKSLSLSLG

23) Insulin precursor fusion protein SS302-035

SEQ ID NO: 69

FVNQHLCGSHLVEALHLVCGERGFHYTPKREAEDLQVGQV
ELGGGPGAGSLQPLALEGSLQKRGIVEQCCTSICSLEQLE
NYCNGGAAVAPPPALPAPVRLPGPAVAPPPALPAPVRLPG
PAESKYGPPCPPCPAPEAAGGPSVFLFPPKPKDTLMISRT
PEVTCVVVDVSQEDPEVQFNWYVDGVEVHNAKTKPREEQF
NSTYRVVSVLTVLHQDWLNGKEYKCKVSNKGLPSSIEKTI
SKAKGQPREPQVYTLPPSQEEMTKNQVSLTCLVKGFYPSD
IAVEWESNGQPENNYKTTPPVLDSDGSFFLYSRLTVDKSR
WQEGNVFSCSVMHEALHNHYTQKSLSLSLG

24) Insulin precursor fusion protein SS302-036

SEQ ID NO: 70

FVNQHLCGSHLVEALELVCGERGFHYTPKREAEDLQVGQV
ELGGGPGAGSLQPLALEGSLKRGIVEQCCTSICSLEQLEN
YCNGGAAVAPPPALPAPVRLPGPAVAPPPALPAPVRLPGP
AESKYGPPCPPCPAPEAAGGPSVFLFPPKPKDTLMISRTP
EVTCVVVDVSQEDPEVQFNWYVDGVEVHNAKTKPREEQFN
STYRVVSVLTVLHQDWLNGKEYKCKVSNKGLPSSIEKTIS
KAKGQPREPQVYTLPPSQEEMTKNQVSLTCLVKGFYPSDI
AVEWESNGQPENNYKTTPPVLDSDGSFFLYSRLTVDKSRW
QEGNVFSCSVMHEALHNHYTQKSLSLSLG

25) Insulin precursor fusion protein SS302-037

SEQ ID NO: 71

FVNQHLCGSHLVEALYLVCGERGFFYTPKREAEDLQVGQV
ELGGGPGAGSLQPLALEGSLQKRGIVEQCCTSICSLEQLE
NYCNGGAAVAPPPALPAPVRLPGPAVAPPPALPAPVRLPG
PAESKYGPPCPPCPAPEAAGGPSVFLFPPKPKDTLMISRT
PEVTCVVVDVSQEDPEVQFNWYVDGVEVHNAKTKPREEQF
NSTYRVVSVLTVLHQDWLNGKEYKCKVSNKGLPSSIEKTI
SKAKGQPREPQVYTLPPSQEEMTKNQVSLTCLVKGFYPSD
IAVEWESNGQPENNYKTTPPVLDSDGSFFLYSRLTVDKSR
WQEGNVFSCSVMHEALHNHYTQKSLSLSLG

26) Insulin precursor fusion protein SS302-038

SEQ ID NO: 72

FVNQHLCGSHLVEALYLVCGERGFFYTPKTRREAEDLQVG
QVELGGGPGAGSLQPLALEGSLQKRGIVEQCCTSICSLYQ
LENYCNGGAAVAPPPALPAPVRLPGPAVAPPPALPAPVRL
PGPAESKYGPPCPPCPAPEAAGGPSVFLFPPKPKDTLMIS
RTPEVTCVVVDVSQEDPEVQFNWYVDGVEVHNAKTKPREE

-continued

QFNSTYRVVSVLTVLHQDWLNGKEYKCKVSNKGLPSSIEK

TISKAKGQPREPQVYTLPPSQEEMTKNQVSLTCLVKGFYP

-continued

SDIAVEWESNGQPENNYKTTPPVLDSDGSFFLYSRLTVDK

SRWQEGNVFSCSVMHEALHNHYTQKSLSLSLG

The invention claimed is:

1. An insulin-Fc fusion protein with a structure of Ins-L-Fc, wherein

Ins is an insulin moiety providing insulin activity and comprises A and B chains of insulin linked by a covalent bond and located in different peptide chains; the covalent bond is a disulfide bond;

L is a linker linking Ins and Fc, L is a polypeptide fragment, wherein L comprises one or more rigid units selected from the group consisting of

| L | Sequence |
|---|---|
| CA | SASSKAPPPSLPSPSRLPGPSDTPILPQ (SEQ ID NO: 27); |
| CTP | SSSSKAPPPSLPSPSRLPGPSDTPILPQ (SEQ ID NO: 28); |
| 2CTP | SASSKAPPPSLPSPSRLPGPSDTPILPQ SSSSKAPPPSLPSPSRLPGPSDTPI LPQ (SEQ ID NO: 29); |
| C1 | VAPPPALPAPVRLPGPA (SEQ ID NO: 30); |
| C1C | GGGSVAPPPALPAPVRLPGPASSSSKAP PPSLPSPSRLPGPSDTPILPQ (SEQ ID NO: 31); |
| 2C1 | GGGSVAPPPALPAPVRLPGPAVAPPPAL PAPVRLPGPA (SEQ ID NO: 32); |
| C2C | GGGSVAPPPALPAVAPPPALPASSSSKA PPPSLPSPSRLPGPSDTPILPQ (SEQ ID NO: 33); |
| 3C1 | GGAAVAPPPALPAPVRLPGPAVAPPPAL PAPVRLPGPAVAPPPALPAPVRLPGPA (SEQ ID NO: 34); |
| 2C1A | GGAAVAPPPALPAPVRLPGPAVAPPPAL PAPVRLPGPA (SEQ ID NO: 35). |

and

Fc is the Fc region of an immunoglobulin.

2. The fusion protein according to claim 1, wherein the insulin is selected from human insulin, bovine insulin or porcine insulin.

3. A pharmaceutical composition comprising the fusion protein according to claim 1.

4. A method for lowering blood glucose and/or treating diabetes, comprising administering the fusion protein according to claim 1 to a subject in need thereof.

5. The method according to claim 4, wherein the diabetes is type I or type II diabetes.

6. The fusion protein according to claim 1, wherein the Fc region is an Fc region derived from IgG2.

7. The fusion protein according to claim 1, wherein the amino acid sequence of B chain is SEQ ID NO: 87, the amino acid sequence of A chain, L and Fc is SEQ ID NO: 88;

the amino acid sequence of B chain is SEQ ID NO: 93, the amino acid sequence of A chain, L and Fc is SEQ ID NO: 94;

the amino acid sequence of B chain is SEQ ID NO: 97, the amino acid sequence of A chain, L and Fc is SEQ ID NO: 98;

the amino acid sequence of B chain is SEQ ID NO: 99, the amino acid sequence of A chain, L and Fc is SEQ ID NO: 100;

the amino acid sequence of B chain is SEQ ID NO: 107, the amino acid sequence of A chain, L and Fc is SEQ ID NO: 108;

the amino acid sequence of B chain is SEQ ID NO: 113, the amino acid sequence of A chain, L and Fc is SEQ ID NO: 114;

the amino acid sequence of B chain is SEQ ID NO: 115, the amino acid sequence of A chain, L and Fc is SEQ ID NO: 116; or the amino acid sequence of B chain is SEQ ID NO: 117, the amino acid sequence of A chain, L and Fc is SEQ ID NO: 118.

* * * * *